(12) United States Patent
Neumann

(10) Patent No.: US 12,014,252 B2
(45) Date of Patent: Jun. 18, 2024

(54) SYSTEMS AND METHODS FOR IMPLEMENTING GENERATED ALIMENTARY INSTRUCTION SETS BASED ON VIBRANT CONSTITUTIONAL GUIDANCE

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 0 days.

(21) Appl. No.: 17/833,605

(22) Filed: Jun. 6, 2022

(65) Prior Publication Data
US 2022/0309403 A1    Sep. 29, 2022

Related U.S. Application Data

(63) Continuation of application No. 16/397,791, filed on Apr. 29, 2019, now Pat. No. 11,392,854.

(51) Int. Cl.
G06F 16/30     (2019.01)
G06F 9/38      (2018.01)
G06N 5/04      (2023.01)
G06N 20/00     (2019.01)
G16H 20/30     (2018.01)

(52) U.S. Cl.
CPC ........... *G06N 20/00* (2019.01); *G06F 9/3838* (2013.01); *G06N 5/04* (2013.01); *G16H 20/30* (2018.01)

(58) Field of Classification Search
None
See application file for complete search history.

(56) References Cited

U.S. PATENT DOCUMENTS

| | | | |
|---|---|---|---|
| 2009/0259488 A1* | 10/2009 | Gounares | G16H 70/20 705/7.42 |
| 2010/0179930 A1* | 7/2010 | Teller | G06N 20/00 706/12 |
| 2010/0241454 A1* | 9/2010 | Firminger | G16H 50/20 715/833 |
| 2011/0318717 A1* | 12/2011 | Adamowicz | G16H 20/60 434/127 |
| 2013/0304492 A1* | 11/2013 | Hermann | G16H 20/40 705/2 |
| 2014/0019151 A1* | 1/2014 | Adami | G16H 50/20 705/2 |

(Continued)

*Primary Examiner* — Polina G Peach
(74) *Attorney, Agent, or Firm* — Caldwell Intellectual Property Law

(57) ABSTRACT

A system and method for implementing an alimentary instruction set based on vibrant constitutional guidance using artificial intelligence, the system comprising at least a server configured to receive at least a biological extraction from a user and training data, generate a diagnostic output as a function of the at least a biological extraction and training data, generate a comprehensive instruction set associated with the user based on the diagnostic output, transmit the comprehensive instruction set to at least a user client device associated with the user, generate at least an advisory output as a function of the comprehensive instruction set, and transmit the advisory output to at least an advisor client device.

14 Claims, 30 Drawing Sheets

(56) References Cited

U.S. PATENT DOCUMENTS

| | | | |
|---|---|---|---|
| 2015/0294595 A1* | 10/2015 | Hu | G06Q 10/101 |
| | | | 434/236 |
| 2018/0144820 A1* | 5/2018 | Grimmer | G16H 20/60 |
| 2018/0181721 A1* | 6/2018 | Boland | G16H 80/00 |
| 2018/0293638 A1* | 10/2018 | Simpson | G16H 20/60 |
| 2018/0361203 A1* | 12/2018 | Wang | G06N 20/00 |
| 2019/0062813 A1* | 2/2019 | Amin | B01L 3/5635 |
| 2019/0221303 A1* | 7/2019 | Bennett | G16H 10/20 |
| 2019/0304000 A1* | 10/2019 | Simpson | G01N 33/492 |
| 2020/0243199 A1* | 7/2020 | Farley | G16H 70/20 |

\* cited by examiner

Selecting an Optimal Handler as a Function of the Plurality of Constraints
2725

Transmitting a Subset of Data Associated with the User to the Optimal Handler
2730

SYSTEMS AND METHODS FOR IMPLEMENTING GENERATED ALIMENTARY INSTRUCTION SETS BASED ON VIBRANT CONSTITUTIONAL GUIDANCE

CROSS-REFERENCE TO RELATED APPLICATIONS

This application is a continuation of Non-provisional application Ser. No. 16/397,791 filed on Apr. 29, 2019 and entitled "SYSTEMS AND METHODS FOR IMPLEMENTING GENERATED ALIMENTARY INSTRUCTION SETS BASED ON VIBRANT CONSTITUTIONAL GUIDANCE," the entirety of which is incorporated herein by reference.

FIELD OF THE INVENTION

The present invention generally relates to the field of artificial intelligence. In particular, the present invention is directed to systems and methods for implementing generated alimentary instruction sets based on vibrant constitutional guidance using artificial intelligence.

BACKGROUND

Generation of alimentary instructions by deriving prognostic data is a process hampered by the complexity of the relevant data. As biological information becomes increasingly complex, effective analysis of data to produce practical, and practicable, instruction sets is an increasing challenge which results in numerous complexities associated with the execution of the instruction sets. Existing solutions fail to address the volumes of information to be assessed and the multivariate complexity of the required solutions.

SUMMARY OF THE DISCLOSURE

In one aspect, a system for implementing a generated alimentary instruction set based on vibrant constitutional guidance using artificial intelligence is presented, the system comprising at least a server configured to receive, at a diagnostic engine operating on the at least a server, at least a biological extraction from a user and training data, generate, at the diagnostic engine, a diagnostic output as a function of the at least a biological extraction and training data, generate, at a plan generation module operating on the at least a server, a comprehensive instruction set associated with the user based on the diagnostic output, transmit, at a client-interface module operating on the at least a server, the comprehensive instruction set to at least a user client device associated with the user, generate, at an advisory module executing on the at least a server, at least an advisory output as a function of the comprehensive instruction set, and transmit, at the advisory module, the advisory output to at least an advisor client device.

In another aspect, a method for implementing an alimentary instruction set based on vibrant constitutional guidance using artificial intelligence is shown, the method performed by at least a server and comprising receiving, at a diagnostic engine operating on the at least a server, at least a biological extraction from a user and training data, generating, at the diagnostic engine, a diagnostic output as a function of the at least a biological extraction and training data, generating, at a plan generation module operating on the at least a server, a comprehensive instruction set associated with the user based on the diagnostic output, transmitting, at a client-interface module operating on the at least a server, the comprehensive instruction set to at least a user client device associated with the user, generating, at an advisory module executing on the at least a server, at least an advisory output as a function of the comprehensive instruction set, and transmitting, at the advisory module, the advisory output to at least an advisor client device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Systems and methods are provided for implementing alimentary instruction sets generated via machine learning. The alimentary instruction sets are configured to interact with a plurality of applicable processes and performances relating to users within the vibrant constitutional network. The alimentary instruction sets may automatically interact and generate sets of instructions receivable by one or more performances and processes. The one or more performances are associated with one or more physical performance entities configured to receive one or more subsets of data based on the alimentary instruction sets, and the physical performance entities are further configured to execute instructions, orders, and requests associated with the one or more subsets of data.

Systems and methods described herein provide improvements to the execution of alimentary and/or alimentary instruction sets; wherein the alimentary instruction sets comprise a plurality of information derived from one or more analyses performed on collected data associated with a user. By using a rule-based model or a machine-learned model, one or more analyses are performed on the collected data, and outputs of training data are generated based on the one or more analyses on the collected data. The outputs are used to generate instruction sets that are used to generate the alimentary instruction sets that are configured to automatically interact with a plurality of performances and processes.

Figure 1:
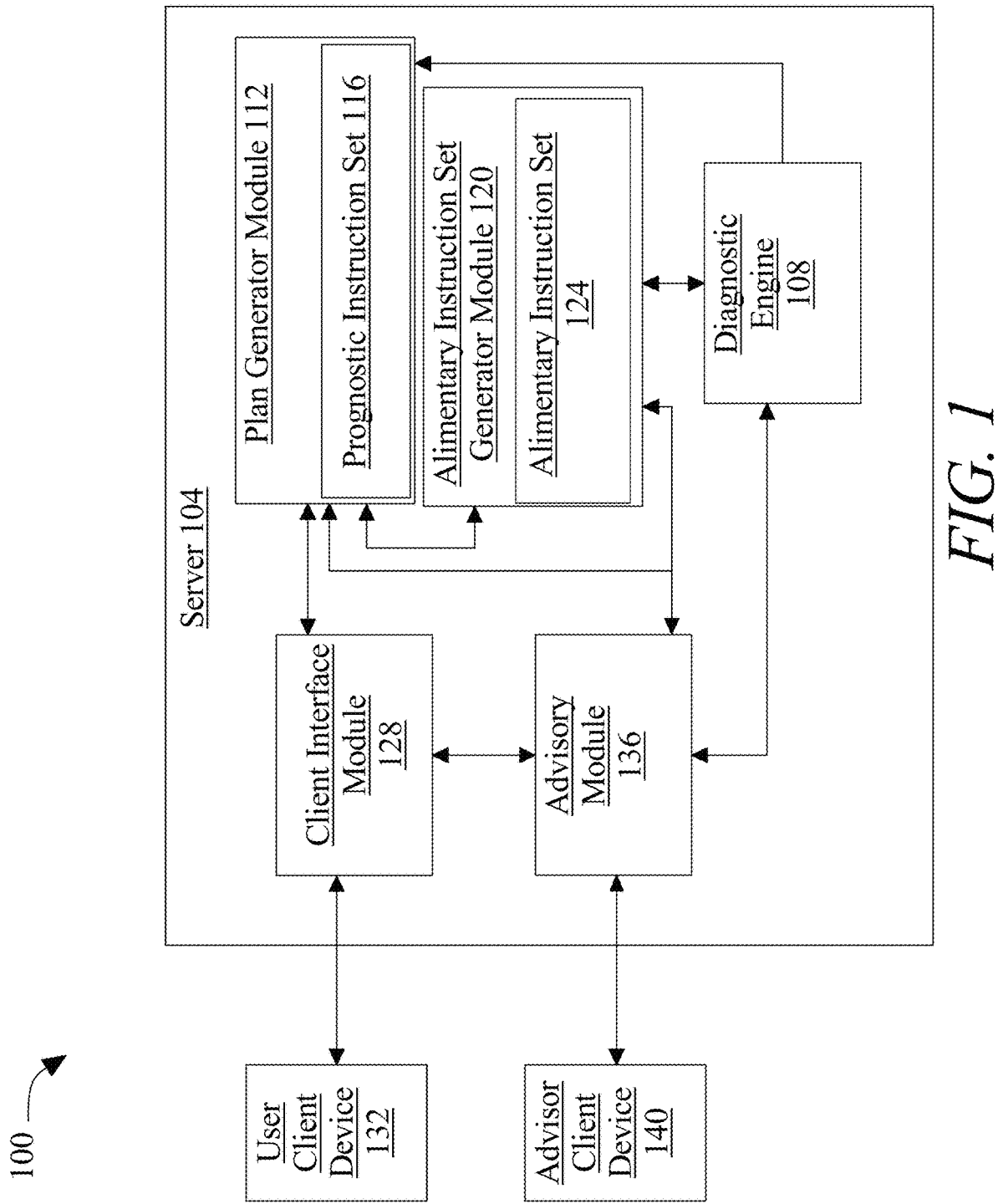
FIG. 1 is a block diagram illustrating an exemplary embodiment of a vibrant constitutional guidance network.

Turning now to FIG. 1, a vibrant constitutional network system 100 is presented. System 100 includes at least a server 104. At least a server 104 may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

Still referring to FIG. 1, system 100 includes a diagnostic engine 108 operating on the at least a server 104, wherein the diagnostic engine 108 configured to receive at least a biological extraction from a user and generate a diagnostic output. At least a server 104, diagnostic engine 108, and/or one or more modules operating thereon may be designed and/or configured to perform any method, method step, or sequence of method steps in any embodiment described in this disclosure, in any order and with any degree of repetition. For instance, at least a server 104 and/or diagnostic engine 108 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 and/or diagnostic engine 108 may be configured to perform any step or sequence of steps as described in this disclosure; steps may be performed in parallel, such as simultaneously and/or substantially simultaneously performing a step two or more times using two or more parallel threads, processor cores, or the like. Division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing. Any module and/or hardware and/or software component as described herein may be created using any combination of hardware and/or software logic commands, and may be physically or conceptually separate from or merged with any other such module, as persons skilled in the art will appreciate upon reviewing the entirety of this disclosure.

Figure 2:
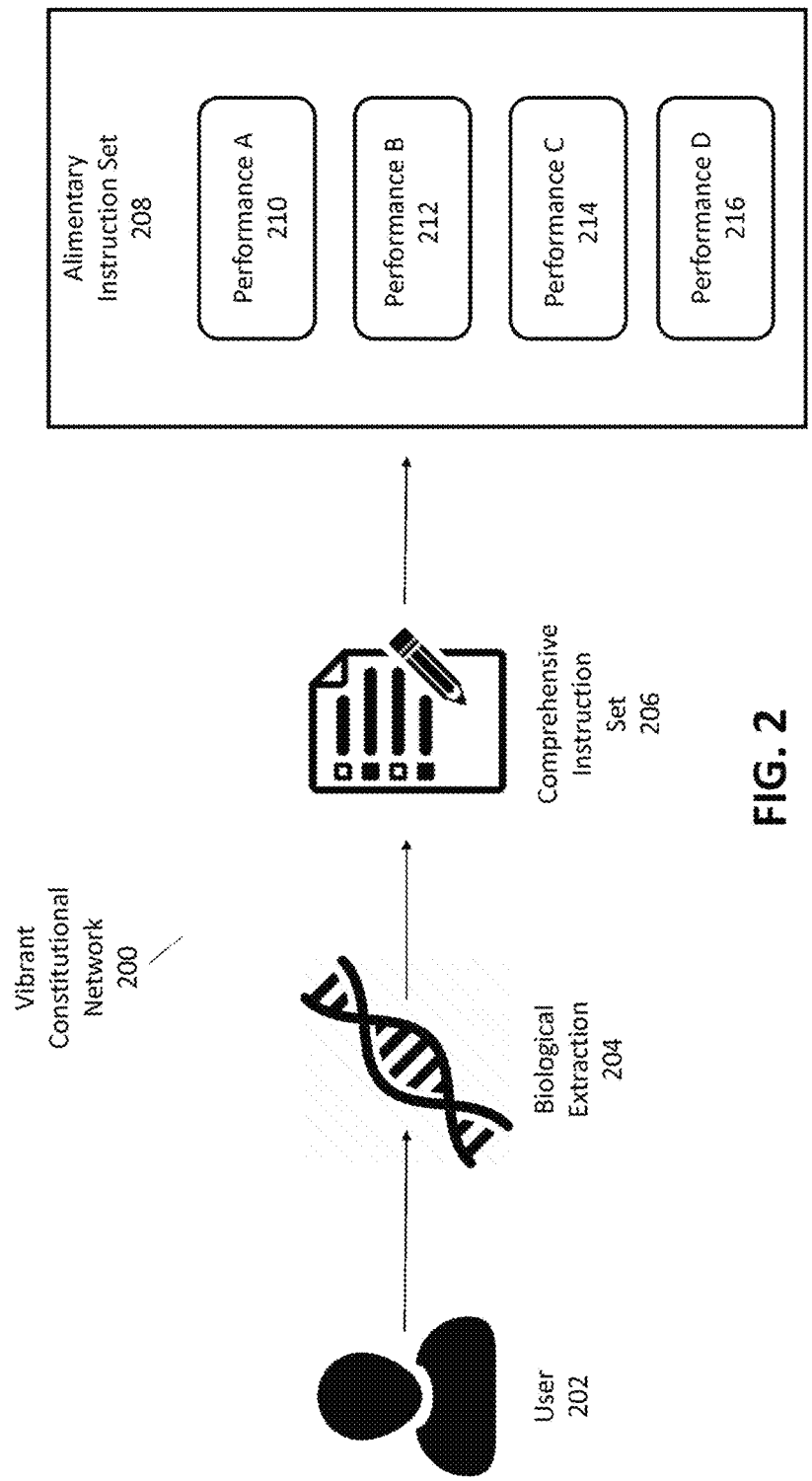
FIG. 2 is a block diagram illustrating an exemplary embodiment of a vibrant constitutional guidance network generating an alimentary instruction set.

Referring now to FIG. 2, a vibrant constitutional network 200 within system 100 is presented. Network 200 may include one or more users 202 who may interact with system 100. In application, a user extraction 204 is collected from user 202 and one or more analyses are performed on the user extraction 204 in order to generate a comprehensive instruction set 206 reflecting analyses and diagnostics associated with user 202. Based on components included within comprehensive instruction set 206, an alimentary instruction set 208 is generated. In one embodiment, alimentary instruction set 208 is generated by an alimentary instruction set generation module configured to receive a plurality of alimentary information relating to user 202 derived from comprehensive instruction set 206. Information contained in the comprehensive instruction set 206 may be supplemented by one or more creditable sources either within or outside of network 200.

In one embodiment, and still viewing FIG. 2, alimentary instruction set 208 may reflect an applicable solution to nourishment requirements, constitutional or chemical deficiencies, and other applicable factors. Alimentary instruction set 208 may include performances 210-216 configured to reflect a plurality of performances triggered by alimentary instruction set 208 within the comprehensive instruction set 206. For example, alimentary instruction set 208 may comprise a component seeking to remedy a vitamin deficiency of user 202 based on information within the comprehensive instruction set 206. Based on this component, alimentary instruction set 208 may automatically communicate with performance A 210 by transmitting a plurality of executable instructions to performance A 210 that result in a request to order vitamins or supplements to remedy the deficiency of user 202. In a particular embodiment of the invention, performances 210-216 may be companies, facilities, organizations, platforms, programs, mobile applications, networks, or any other applicable means configured to receive and process orders, requests, or instructions. As a non-limiting example, performances 210-216 may include enlistment of one or more applicable professionals configured to counsel, support, or mentor user 202 regarding applicable areas.

In one embodiment, and continuing to refer to FIG. 2, alimentary instruction set 208 and/or a user device associated with an alimentary instruction set may be presented to user 202 via a graphical user interface, which may be configured to interact with user 202 allowing user 202 to monitor and amend details associated with alimentary instruction set 208. Furthermore, an alimentary instruction set may be monitored and amended based on input provided by an applicable professional either associated with alimentary instruction set 208 or designated by user 202 to be associated with alimentary instruction set 208.

Still referring to FIG. 2, a vibrant constitutional network 200 within system 100 is presented. Network 200 may include one or more users 202 who may interact with system 100. In application, a user extraction 204 is collected from user 202 and one or more analyses are performed on the user extraction 204 in order to generate a comprehensive instruction set 206 reflecting analyses and diagnostics associated with user 202. Based on components included within comprehensive instruction set 206, an alimentary instruction set 208 is generated. In one embodiment, alimentary instruction set 208 is generated by an alimentary instruction set generation module configured to receive a plurality of alimentary information relating to user 202 derived from comprehensive instruction set 206. Information contained in the comprehensive instruction set 206 may be supplemented by one or more creditable sources either within or outside of network 200.

In one embodiment, and still viewing FIG. 2, alimentary instruction set 208 may reflect an applicable solution to nourishment requirements, deficiencies, and other applicable factors. Alimentary instruction set 208 may include performances 210-216 configured to reflect a plurality of performances triggered by alimentary instruction set 208 within the comprehensive instruction set 206. For example, alimentary instruction set 208 may comprise a component seeking to remedy a vitamin deficiency of user 202 based on information within the comprehensive instruction set 206. Based on this component, alimentary instruction set 208 may automatically communicate with performance A 210 by transmitting a plurality of executable instructions to performance A 210 that result in a request to order vitamins or supplements to remedy the deficiency of user 202. In a particular embodiment of the invention, performances 210-216 may be companies, facilities, organizations, platforms, programs, mobile applications, networks, or any other applicable means configured to receive and process orders, requests, or instructions. As a non-limiting example, performances 210-216 may include enlistment of one or more applicable professionals configured to counsel, support, or mentor user 202 regarding applicable areas.

In one embodiment and continuing to refer to FIG. 2, alimentary instruction set 208 may be presented on a graphical user interface of user client device 132, which may be configured to interact with user 202 allowing user 202 to monitor and amend details associated with alimentary instruction set 208. Furthermore, alimentary instruction set 208 may be configured to be monitored and amended by an applicable professional, via an alternative client device, either associated with generation of alimentary instruction set 208 or designated by user 202 to be associated with alimentary instruction set 208.

Figure 3:
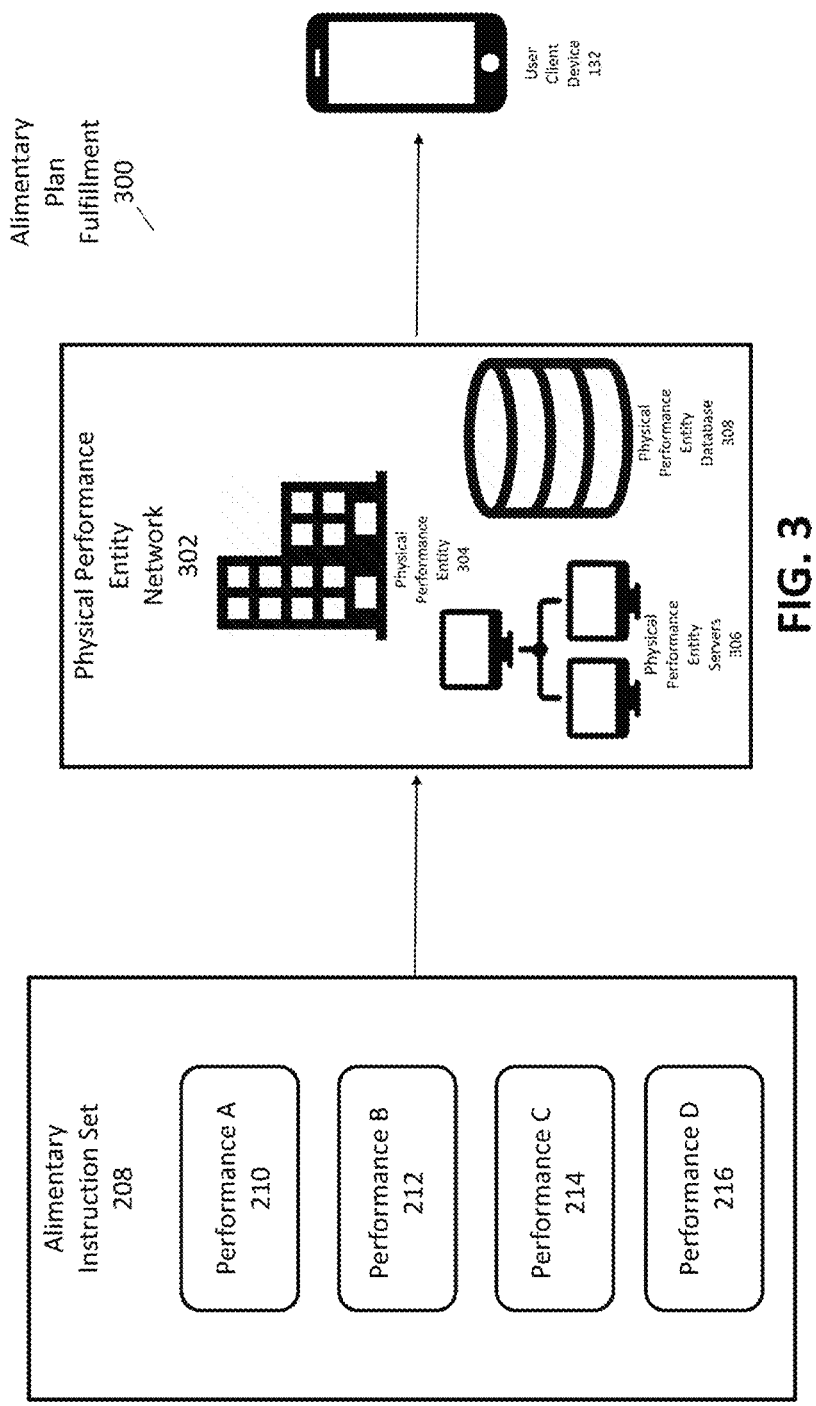
FIG. 3 is a block diagram illustrating an exemplary embodiment of a physical performance entity fulfilling an order of the alimentary instruction set.

Referring now to FIG. 3, an alimentary instruction set fulfillment network 300 within vibrant constitutional network 200 is presented. Fulfillment network 300 is may include performances 210-216 communicatively coupled to a physical performance entity network 302, which is configured to interact with a user client device 310. Physical performance entity network 302 may include at least a physical performance entity 304, which may include any physical performance executor as described in further detail below, a plurality of physical performance entity servers 306, and a physical performance entity database 308. Each server of physical performance entity servers 306 may include any computing device suitable for use as at least a server 104. Physical performance entity database 308 may include any database or datastore as described in this disclosure. Although only a single physical performance entity network 302 is depicted, fulfillment network 300 may be configured to involve multiple physical performance entity networks or various performances within a particular physical performance entity network 302 when applicable. In one embodiment, performances 210-216 may each be communicatively coupled respectively to a different physical performance entity network 302 associated with different physical performance entities 304. For example, performance A 210 may be a component of alimentary instruction set 208 configured to transmit instructions to a first physical performance entity network 302 relating to an order for specific groceries necessary for a proposed meal plan of alimentary instruction set 208, performance B 212 may be a component of alimentary instruction set 208 configured to transmit instructions to a second physical performance entity network 302 relating to an order for specific vitamins based on comprehensive instruction set 206 and alimentary instruction set 208, performance C 214 may be a component of alimentary instruction set 208 configured to transmit instructions to a third physical performance entity network 302 relating to an order for a specific alimentary supplement based on comprehensive instruction set 206 and alimentary instruction set 208, and performance D 216 may be a component of alimentary instruction set 208 configured to transmit instructions to a fourth physical performance entity network 302 relating to an order for a specific food scale.

Figure 4:
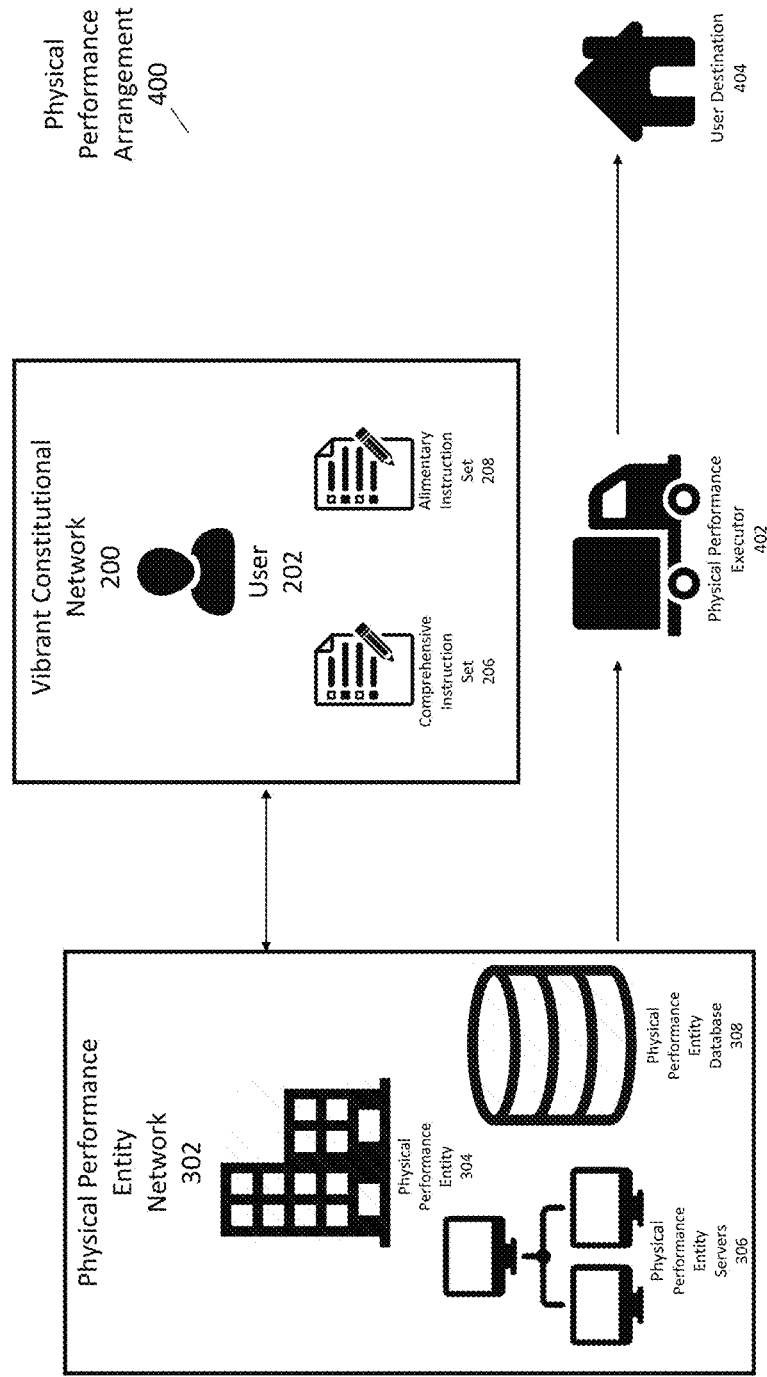
FIG. 4 is a block diagram illustrating an exemplary embodiment of implementation of an alimentary instruction set associated with a user.

Referring now to FIG. 4, a schematic diagram of an implementation arrangement for physical performance arrangement 400 based on the alimentary instruction set 208 within vibrant constitutional network 200 is presented. Physical performance arrangement 400 may be configured and/or arranged to include transmissions and occurrence by and between components of vibrant constitutional network 200 and components of physical performance entity network 302 in order to ensure that physical performance arrangement 400 is successfully implemented. Physical performance arrangement 400 may be further configured to include a physical performance executor 402 that is configured to, either automatically or via election by user 202, deliver or support reception of components of alimentary instruction set 208 via a user destination 404 associated with user 202. In one embodiment, physical performance executor 402 may be a component of physical performance entity network 302 or a third-party provider that is elected by vibrant constitutional network 200, user 202, or physical performance entity 304.

In one embodiment, and still referring to FIG. 4, physical performance executor 402 may be any transportation channel including, but not limited to, Amazon, Grubhub, DoorDash, Postmates, Seamless, Uber, EatStreet, FedEx, UPS, Instacart, or any other channel configured to process and execute requests related to nourishment or supplements. In application, physical performance entity network 302 is configured to receive a physical performance instruction set associated with respective performances 210-216 along with a plurality of information comprised within vibrant constitutional network 200 that may or may not be included in comprehensive instruction set 206 or alimentary instruction set 208. For example, information pertaining to user 202 may include, but is not limited to, remittance information, preferred remittance methods, one or more physical addresses, telephone numbers, e-mail, and any other applicable information relating to user 202. In one embodiment, the plurality of information may be stored and accessed in physical performance entity database 308 based on a previous session or interaction between user 202 and physical performance entity 304. Components of performances 210-216 of alimentary instruction set 208 are configured to be transmitted to one or more physical performance entities 302 resulting in the one or more physical performance entities 302 providing a plurality of constraints. The plurality of constraints may include, but are not limited to, performance limitations associated with physical performance entity 302 based on the performance capacity of physical performance entity 302, available or unavailable resources necessary for physical performance entity 302 to execute components of performances 210-216, scheduling conflicts, proximity of physical performance entity 302 to user destination 404, dietary constraints of user 202 provided by vibrant constitutional network 200, or any other applicable limitations associated with physical performance entity 302. In one embodiment, user 202 may manually perform the physical performance instruction set via picking up components of alimentary instruction set 208 from physical performance entity 304, physical performance executor 402, or any other applicable source.

In one embodiment, and still referring to FIG. 4, the plurality of constraints are received and utilized via at least a server 104 in order to select one or more optimal handlers that are able to execute the physical performance instruction set as a function of the plurality of constraints. As described herein, an optimal handler may include but is not limited to an elected or designated physical performance entity 304 or physical performance executor 402 that is able to most accurately align its own limitations or constraints with those of user 202 in order to efficiently carry out physical performance arrangement 400. For example, if performance A 210 specifies that user 202 requires specific alimentary components within the next hour from a source within 3 miles of a specific zip code, the plurality of constraints associated with each respective physical performance entity 304 are utilized to determine which physical performance entity 304 is an optimal handler based on the plurality of constraints that conform to the specific requirements of performance A 210. Once the optimal handler is selected based on the most conformity between the plurality of constraints and requirements/preferences of user 202, at least a server 104 is configured to transmit a subset of data associated with user 202 to the physical performance entity network 302 associated with the selected optimal handler. In one embodiment, the subset of data may be data comprised within vibrant constitutional network 200 such as preferred options associated with physical performance executor 402, physical address associated with user destination 404, or any other data configured to assist physical performance entity 304 with physical performance arrangement 400.

In one embodiment, and continuing to refer to FIG. 4, the optimal handler may be selected based on one or more preferences associated with user 202 via user input provided to vibrant constitutional network 200 or physical performance entity network 302. The optimal handler may also be designated via a process of elimination based on the availability of physical performance entity 304. For example, if more than one physical performance entity 304 is available to execute the physical performance instruction set, then the physical performance entity 304 comprising the least constraints or conforms the most with the physical performance instruction set is determined the optimal handler. In one embodiment, more than one physical performance entity 304 may be determined as the optimal handler resulting in various components of the physical performance instruction set being allocated accordingly across the selected optimal handlers.

Still referring to FIG. 4, selection of an optimal handler may be performed by reference to geographical constraints. For instance, and without limitation, optimal handler may be selected from among physical performance entities by determining a distance from a user, a travel time to arrive at a user, or the like, for each of a plurality of physical performance entities; plurality may be selected according to any criteria described in this disclosure. Selection of optimal handler may further include selection of a physical performance entity minimizing a travel time, travel distance, delivery time, or the like to user. For instance, and without limitation, a physical performance entity 304 capable of arriving at a user location the soonest may be selected. Travel time, distance, and the like may alternatively or additionally be compared to a threshold amount, such as a maximal travel time and/or distance set by system 100 and/or in user preferences as received and/or recorded according to this disclosure. Travel time and/or distance may be determined by reference to a location of a physical performance entity 304 which may be static, such as a recorded address, and/or dynamic, such as a location of a computing device and/or mobile device operated by physical performance entity 304, a vehicle or employee thereof, or the like via global positioning service (GPS) or other navigation facilities.

With continued reference to FIG. 4, in one embodiment, at least a server 104 may be configured to retrieve data from user client device 132, such as geolocation of user 202, browsing history metadata, and other applicable data comprised on user client device in order to assist with the selection of one or more optimal handlers. At least a server 104 may be configured to establish a communication session between user 202 and physical performance executor 402 via user client device 132, which may be hosted by vibrant constitutional network 200 in order to supplement data associated with user destination 404 to ensure physical performance arrangement 400 is completed. In one embodiment, physical performance entity 304 or physical performance executor 402 may be an entity configured to process and package physical performance instruction sets which are configured to support on-site pick-up of components of alimentary instruction set 208.

In one embodiment, and still referring to FIG. 4, at least a server 104 may be configured to receive, from physical performance entity network 302 or physical performance executor 402, a plurality of data associated with recommendations, specials, suggestions, specials, or general updates pertaining to components of alimentary instruction set 208 to user 202 via vibrant constitutional network 200. For example, if performance B 212 pertains to a plurality of alimentary components configured to lower the blood sugar of user 202, then at least a server 104 may receive suggestions, or competitive alternatives associated with the plurality of alimentary components configured to lower the blood sugar of user 202 from physical performance entity 304, physical performance executory 402, or the optimal handler. At least a server 104 is configured to receive the plurality of data, and user 202 within vibrant constitutional network 200 is presented the plurality of data via user client device 132. In one embodiment, user client device 132, via data received by at least a server 104 within vibrant constitutional network 200, is configured to receive alerts or notifications relating to updates or mishaps relating to physical performance arrangement 400, tracking or status of delivery by physical performance executor 402, or changes and adjustments related to the processing or implementation of physical performance arrangement 400.

Still referring to FIG. 4, in one embodiment, the physical performance instruction set, via the at least a server 104, may be continuously updated or altered based on data included in alimentary instruction set 208 being updated via data collected by at least a server 104 or an external source such as an informed advisor associated with comprehensive instruction set 206, alimentary instruction set 208, or user 202 directly. For example, if performance C 214 of alimentary instruction set 208 was initially intended to lower the blood sugar of user 202 and the physical performance instruction set inspired by performance C 214 comprising a specified amount of an applicable alimentary component results in the blood sugar of user 202 being progressively reduced (discovered by the diagnostic output), then vibrant constitutional network 200, via the at least a server 104, may automatically update either alimentary instruction set 208 or performance C 214 directly resulting in a subsequent physical performance instruction set comprising an order for a reduced amount of the applicable alimentary component.

Figure 5:
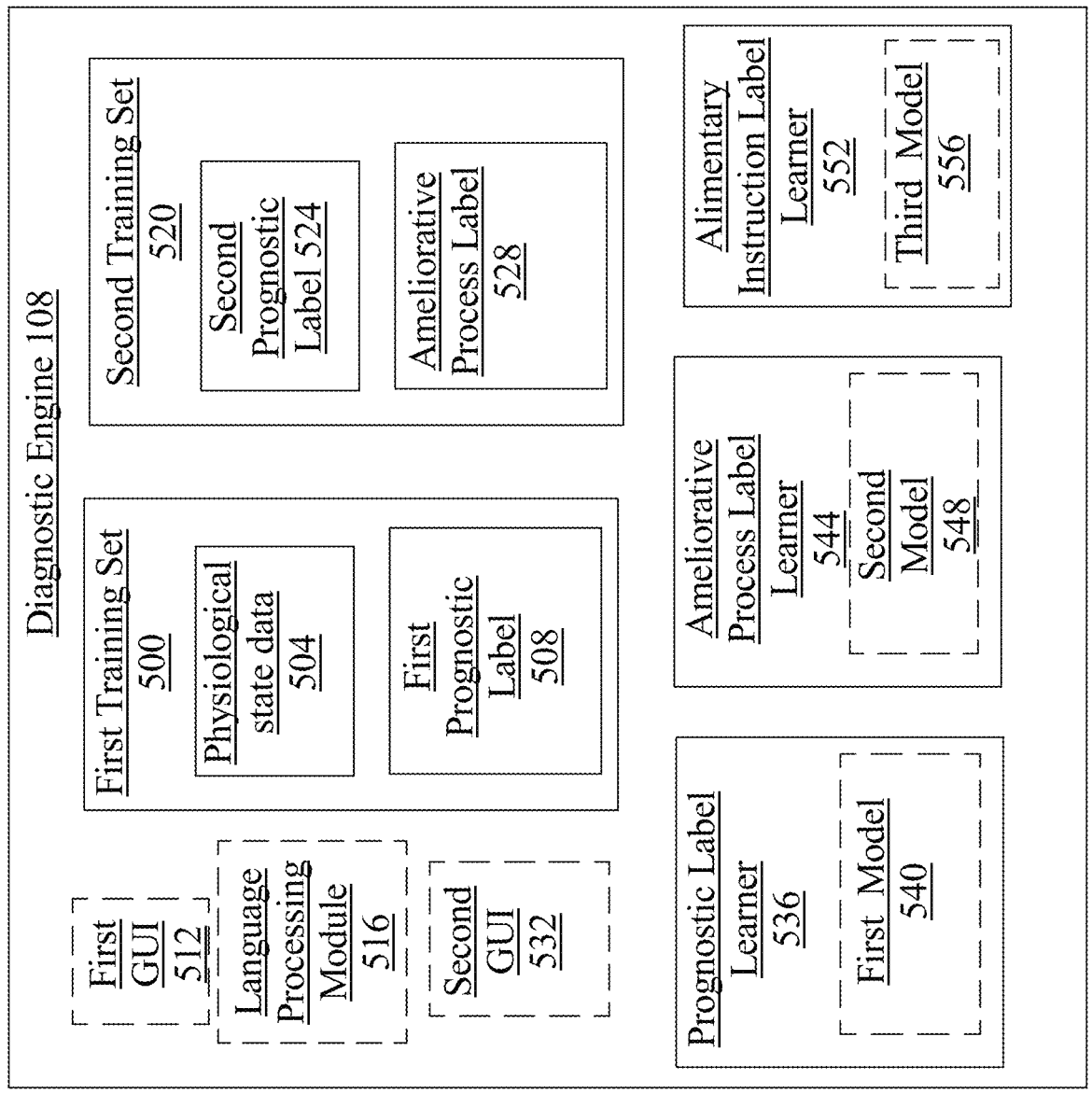
FIG. 5 is a block diagram illustrating an exemplary embodiment of a diagnostic engine.

Referring now to FIG. 5, at least a server 104 and/or diagnostic engine 108 may be designed and configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 5, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like;

categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 5, categorization device may be configured to receive a first training set 500 including a plurality of first data entries, each first data entry of the first training set 500 including at least an element of physiological state data 504 and at least a correlated first prognostic label 508. At least an element of physiological state data 504 may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data 504 may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data 504 may include, without limitation, immune function data such as Interleukine-6 (IL-6), TNF-alpha, systemic inflammatory cytokines, and the like.

With continued reference to FIG. 5, physiological state data 504 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data 504 may include measures of glucose metabolism such as fasting glucose levels and/or hemoglobin A1-C(HbA1c) levels. Physiological state data 504 may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data 504 may include measures of estimated glomerular filtration rate (eGFR). Physiological state data 504 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline photophatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data 504 may include antinuclear antibody levels. Physiological state data 504 may include aluminum levels. Physiological state data 504 may include arsenic levels. Physiological state data 504 may include levels of fibronigen, plasma cystatin C, and/or brain natriuretic peptide.

Continuing to refer to FIG. 5, physiological state data 504 may include measures of lung function such as forced expiratory volume, one second (FEV-1) which measures how much air can be exhaled in one second following a deep inhalation, forced vital capacity (FVC), which measures the volume of air that may be contained in the lungs. Physiological state data 504 may include a measurement blood pressure, including without limitation systolic and diastolic blood pressure. Physiological state data 504 may include a measure of waist circumference. Physiological state data 504 may include body mass index (BMI). Physiological state data 504 may include one or more measures of bone mass and/or density such as dual-energy x-ray absorptiometry. Physiological state data 504 may include one or more measures of muscle mass. Physiological state data 504 may include one or more measures of physical capability such as without limitation measures of grip strength, evaluations of standing balance, evaluations of gait speed, pegboard tests, timed up and go tests, and/or chair rising tests.

Still viewing FIG. 5, physiological state data 504 may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data 504 may include one or more measures of psychological function or state, such as without limitation clinical interviews, assessments of intellectual functioning and/or intelligence quotient (IQ) tests, personality assessments, and/or behavioral assessments. Physiological state data 504 may include one or more psychological self-assessments, which may include any self-administered and/or automatedly computer-administered assessments, whether administered within system 100 and/or via a third-party service or platform.

With continued reference to FIG. 5, physiological state data 504 may include one or more evaluations of sensory ability, including measures of audition, vision, olfaction, gustation, vestibular function and pain. Physiological state data 504 may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data 504 may include proteomic data, which as used herein is data describing all proteins produced and/or modified by an organism, colony of organisms, or system of organisms, and/or a subset thereof. Physiological state data 504 may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data 504 of a person, and/or on prognostic labels and/or alimentary data processes as described in further detail below. Physiological state data 504 may include any physiological state data 504, as described above, describing any multicellular organism living in or on a person including any parasitic and/or symbiotic organisms living in or on the persons; non-limiting examples may include mites, nematodes, flatworms, or the like. Examples of physiological state data 504 described in this disclosure are presented for illustrative purposes only and are not meant to be exhaustive. Persons skilled in the art, upon reviewing the entirety of this disclosure, will be aware of various additional examples of physiological state data 504 that may be used consistently with descriptions of systems and methods as provided in this disclosure.

Continuing to refer to FIG. 5, each element of first training set 500 includes at least a first prognostic label 508. A prognostic label, as described herein, is an element of data identifying and/or describing a current, incipient, or probable future condition affecting a person; condition may include a particular disease, one or more symptoms associated with a syndrome, a syndrome, and/or any other measure of current or future health and/or healthy aging. At least a prognostic label may be associated with a physical and/or somatic condition, a mental condition such as a mental illness, neurosis, or the like, or any other condition affecting human health that may be associated with one or more elements of physiological state data 504 as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrinal disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 5, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

With continued reference to FIG. 5, in each first data element of first training set 500, at least a first prognostic label 508 of the data element is correlated with at least an element of physiological state data 504 of the data element. In an embodiment, an element of physiological data is correlated with a prognostic label where the element of physiological data is located in the same data element and/or portion of data element as the prognostic label; for example, and without limitation, an element of physiological data is correlated with a prognostic element where both element of physiological data and prognostic element are contained within the same first data element of the first training set 500. As a further example, an element of physiological data is correlated with a prognostic element where both share a category label as described in further detail below, where each is within a certain distance of the other within an ordered collection of data in data element, or the like. Still further, an element of physiological data may be correlated with a prognostic label where the element of physiological data and the prognostic label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in first training set 500 and/or first data element consistently with this disclosure.

In an embodiment, and Still referring to FIG. 5, diagnostic engine 108 may be designed and configured to associate at least an element of physiological state data 504 with at least a category from a list of significant categories of physiological state data 504. Significant categories of physiological state data 504 may include labels and/or descriptors describing types of physiological state data 504 that are identified as being of high relevance in identifying prognostic labels. As a non-limiting example, one or more categories may identify significant categories of physiological state data 504 based on degree of diagnostic relevance to one or more impactful conditions and/or within one or more public health fields. For instance, and without limitation, a particular set of biomarkers, test results, and/or biochemical information may be recognized in a given field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 1, diagnostic engine 108 may receive the list of significant categories according to any suitable process; for instance, and without limitation, diagnostic engine 108 may receive the list of significant categories from at least an expert. In an embodiment, diagnostic engine 108 and/or a user device connected to diagnostic engine 108 may provide a graphical user interface, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like.

Figure 6:
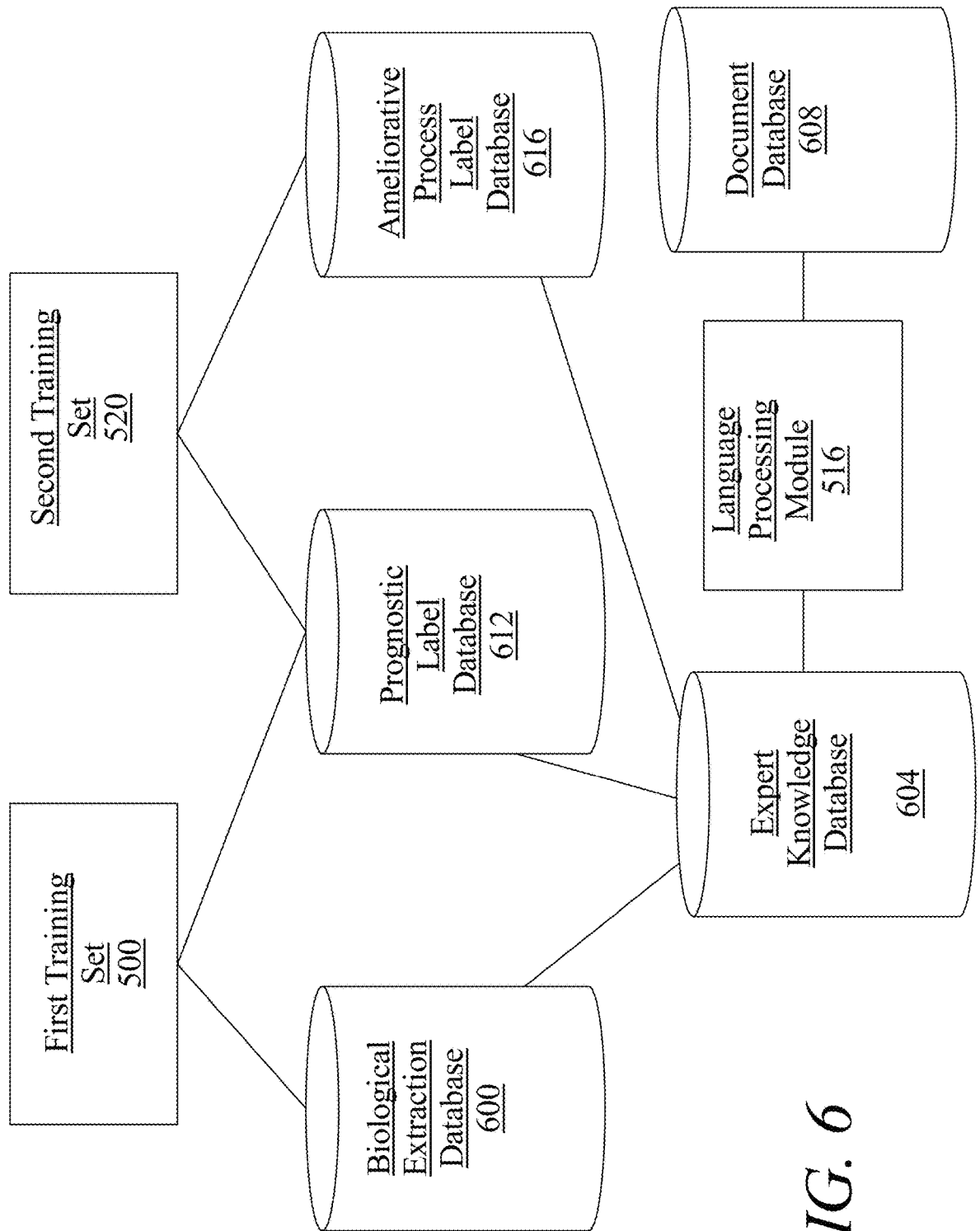
FIG. 6 is a block diagram illustrating embodiments of data storage facilities for use in disclosed systems and methods.

Now referring to FIG. 6, data describing significant categories of physiological data, relationships of such categories to prognostic labels, and/or significant categories of prognostic labels may alternatively or additionally be extracted from one or more documents using a language processing module 516. Language processing module 516 may include any hardware and/or software module. Language processing module 516 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 6, language processing module 516 may compare extracted words to categories of physiological data recorded at diagnostic engine 108, one or more prognostic labels recorded at diagnostic engine 108, and/or one or more categories of prognostic labels recorded at diagnostic engine 108; such data for comparison may be entered on diagnostic engine 108 as described above using expert data inputs or the like. In an embodiment, one or more categories may be enumerated, to find total count of mentions in such documents. Alternatively or additionally, language processing module 516 may operate to produce a language processing model. Language processing model may include a program automatically generated by diagnostic engine 108 and/or language processing module 516 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at diagnostic engine 108, or the like.

Still referring to FIG. 6, language processing module 516 and/or diagnostic engine 108 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 516 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 6, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 6, language processing module 516 may use a corpus of documents to generate associations between language elements in a language processing module 516, and diagnostic engine 108 may then use such associations to analyze words extracted from one or more documents and determine that the one or more documents indicate significance of a category of physiological data, a given relationship of such categories to prognostic labels, and/or a given category of prognostic labels. In an embodiment, diagnostic engine 108 may perform this analysis using a selected set of significant documents, such as documents identified by one or more experts as representing good science, good clinical analysis, or the like; experts may identify or enter such documents via graphical user interface as described or may communicate identities of significant documents according to any other suitable method of electronic communication, or by providing such identity to other persons who may enter such identifications into diagnostic engine 108. Documents may be entered into diagnostic engine 108 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine 108 may automatically obtain the document using such an identifier, for instance by submitting a request to a database or compendium of documents such as JSTOR as provided by Ithaka Harbors, Inc. of New York.

Continuing to refer to FIG. 6, whether an entry indicating significance of a category of physiological data, a given relationship of such categories to prognostic labels, and/or a given category of prognostic labels is entered via graphical user interface, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according to significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of biological extraction, which then may be subjected to ranking, comparison to thresholds and/or elimination as described above.

Still referring to FIG. 6, diagnostic engine 108 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 6, in an embodiment, diagnostic engine 108 may be configured, for instance as part of receiving the first training set 500, to associate at least correlated first prognostic label 508 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result diagnostic engine 108 may modify list of significant categories to reflect this difference.

Still referring to FIG. 5, diagnostic engine 108 is designed and configured to receive a second training set 520 including a plurality of second data entries. Each second data entry of the second training set 520 includes at least a second prognostic label 524; at least a second prognostic label 524 may include any label suitable for use as at least a first prognostic label 508 as described above. Each second data entry of the second training set 520 includes at least an ameliorative process label 528 correlated with the at least a second prognostic label 524, where correlation may include any correlation suitable for correlation of at least a first prognostic label 508 to at least an element of physiological data as described above. As used herein, an ameliorative process label 528 is an identifier, which may include any form of identifier suitable for use as a prognostic label as described above, identifying a process that tends to improve a physical condition of a user, where a physical condition of a user may include, without limitation, any physical condition identifiable using a prognostic label. Ameliorative processes may include, without limitation, exercise programs, including amount, intensity, and/or types of exercise recommended. Ameliorative processes may include, without limitation, dietary or alimentary recommendations based on data including alimentary content, digestibility, or the like. Ameliorative processes may include one or more medical procedures. Ameliorative processes may include one or more physical, psychological, or other therapies. Ameliorative processes may include one or more medications. Alimentary processes may be a form of an ameliorative process and an ameliorative output may include an alimentary process. Persons skilled in the art, upon reviewing the entirety of this disclosure, will be aware of various processes that may be used as ameliorative processes consistently with this disclosure.

Continuing to refer to FIG. 5, in an embodiment diagnostic engine 108 may be configured, for instance as part of receiving second training set 520, to associate the at least second prognostic label 524 with at least a category from a list of significant categories of prognostic labels. This may be performed as described above for use of lists of significant categories with regard to at least a first prognostic label 508. Significance may be determined, and/or association with at least a category, may be performed for prognostic labels in first training set 500 according to a first process as described above and for prognostic labels in second training set 520 according to a second process as described above.

Still referring to FIG. 5, diagnostic engine 108 may be configured, for instance as part of receiving second training set 520, to associate at least a correlated ameliorative process label 528 with at least a category from a list of significant categories of ameliorative process labels 528. In an embodiment, diagnostic engine 108 and/or a user device connected to diagnostic engine 108 may provide a second graphical user interface 532 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to ameliorative labels, where experts may enter data describing ameliorative labels and/or categories of ameliorative labels the experts consider related to entered categories of prognostic labels; for instance, such fields may include drop-down lists or other pre-populated data entry fields listing currently recorded ameliorative labels, and which may be comprehensive, permitting each expert to select an ameliorative label and/or a plurality of ameliorative labels the expert believes to be predicted and/or associated with each category of prognostic labels selected by the expert. Fields for entry of ameliorative labels and/or categories of ameliorative labels may include free-form data entry fields such as text entry fields; as described above, examiners may enter data not presented in pre-populated data fields in the free-form data entry fields. Alternatively or additionally, fields for entry of ameliorative labels may enable an expert to select and/or enter information describing or linked to a category of ameliorative label that the expert considers significant, where significance may indicate likely impact on longevity, mortality, quality of life, or the like as described in further detail below. Graphical user interface may provide an expert with a field in which to indicate a reference to a document describing significant categories of prognostic labels, relationships of such categories to ameliorative labels, and/or significant categories of ameliorative labels. Such information may alternatively be entered according to any other suitable means for entry of expert data as described above. Data concerning significant categories of prognostic labels, relationships of such categories to ameliorative labels, and/or significant categories of ameliorative labels may be entered using analysis of documents using language processing module 516 or the like as described above. In one embodiment, alimentary instruction set 208 may be modified to eliminate categories of ameliorative process labels 528 that are non-alimentary.

Still referring to FIG. 5, diagnostic engine 108 may be configured, for instance as part of receiving second training set 520, to associate at least ameliorative process label 528 with at least a category from a list of significant categories of ameliorative process label 528. In an embodiment, diagnostic engine 108 and/or a user device connected to diagnostic engine 108 may provide a second graphical user interface 532 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to alimentary instruction set labels, where experts may enter data describing alimentary instruction set labels and/or categories of alimentary instruction set labels the experts consider related to entered categories of prognostic labels; for instance, such fields may include drop-down lists or other pre-populated data entry fields listing currently recorded alimentary instruction set labels, and which may be comprehensive, permitting each expert to select an alimentary instruction set label and/or a plurality of alimentary instruction set labels the expert believes to be predicted and/or associated with each category of prognostic labels selected by the expert. Fields for entry of alimentary instruction set labels and/or categories of alimentary instruction set labels may include free-form data entry fields such as text entry fields; as described above, examiners may enter data not presented in pre-populated data fields in the free-form data entry fields. Alternatively or additionally, fields for entry of alimentary instruction set labels may enable an expert to select and/or enter information describing or linked to a category of alimentary instruction set label that the expert considers significant, where significance may indicate likely impact on longevity, mortality, quality of life, or the like as described in further detail below. Graphical user interface may provide an expert with a field in which to indicate a reference to a document describing significant categories of prognostic labels, relationships of such categories to alimentary instruction set labels, and/or significant categories of alimentary instruction set labels. Such information may alternatively be entered according to any other suitable means for entry of expert data as described above. Data concerning significant categories of prognostic labels, relationships of such categories to alimentary instruction set labels, and/or significant categories of alimentary instruction set labels may be entered using analysis of documents using language processing module 516 or the like as described above.

In an embodiment, and Still referring to FIG. 5, diagnostic engine 108 may extract at least a second data entry from one or more documents; extraction may be performed using any language processing method as described above. Diagnostic engine 108 may be configured, for instance as part of receiving second training set 520, to receive at least a document describing at least a medical history and extract at least a second data entry of plurality of second data entries from the at least a document. A history document may include, for instance, a document received from an expert and/or practitioner describing treatment of a patient; document may be anonymized by removal of one or more patient-identifying features from document. A history document may include a case study, such as a case study published in a medical journal or written up by an expert. A history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A history document may contain data describing and/or described by an ameliorative process label 528; for instance, the history document may list a therapy, recommendation, or other alimentary instruction set process that a medical practitioner described or recommended to a patient. A history document may describe an outcome; for instance, medical history document may describe an improvement in a condition describing or described by a prognostic label, and/or may describe that the condition did not improve. Prognostic labels, ameliorative process label 528, and/or efficacy of ameliorative process label 528 may be extracted from and/or determined from one or more medical history documents using any processes for language processing as described above; for instance, language processing module 516 may perform such processes. As a non-limiting example, positive and/or negative indications regarding alimentary instruction set processes identified in medical history documents may be determined in a manner described above for determination of positive and/or negative indications regarding categories of physiological data, relationships of such categories to prognostic labels, and/or categories of prognostic labels.

With continued reference to FIG. 5, diagnostic engine 108 may be configured, for instance as part of receiving second training set 520, to receiving at least a second data entry of the plurality of second data entries from at least an expert. This may be performed, without limitation using second graphical user interface 532 as described above.

Referring again to FIG. 6, data incorporated in first training set 500 and/or second training set 520 may be incorporated in one or more databases. As a non-limiting example, one or elements of physiological state data may be stored in and/or retrieved from a biological extraction database 600. A biological extraction database 600 may include any data structure for ordered storage and retrieval of data, which may be implemented as a hardware or software module. A biological extraction database 600 may be implemented, without limitation, as a relational database, a key-value retrieval datastore such as a NOSQL database, or any other format or structure for use as a datastore that a person skilled in the art would recognize as suitable upon review of the entirety of this disclosure. A biological extraction database 600 may include a plurality of data entries and/or records corresponding to elements of physiological data as described above. Data entries and/or records may describe, without limitation, data concerning particular biological extractions that have been collected; entries may describe reasons for collection of samples, such as without limitation one or more conditions being tested for, which may be listed with related prognostic labels. Data entries may include prognostic labels and/or other descriptive entries describing results of evaluation of past biological extractions, including diagnoses that were associated with such samples, prognoses and/or conclusions regarding likelihood of future diagnoses that were associated with such samples, and/or other medical or diagnostic conclusions that were derived. Such conclusions may have been generated by diagnostic engine 108 in previous iterations of methods, with or without validation of correctness by medical professionals. Data entries in a biological extraction database 600 may be flagged with or linked to one or more additional elements of information, which may be reflected in data entry cells and/or in linked tables such as tables related by one or more indices in a relational database; one or more additional elements of information may include data associating a biological extraction and/or a person from whom a biological extraction was extracted or received with one or more cohorts, including demographic groupings such as ethnicity, sex, age, geographical region, or the like, one or more common diagnoses or physiological attributes shared with other persons having biological extractions reflected in other data entries, or the like. Additional elements of information may include one or more categories of physiological data as described above. Additional elements of information may include descriptions of particular methods used to obtain biological extractions, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a biological extraction database 600 may reflect categories, cohorts, and/or populations of data consistently with this disclosure.

Figure 7:
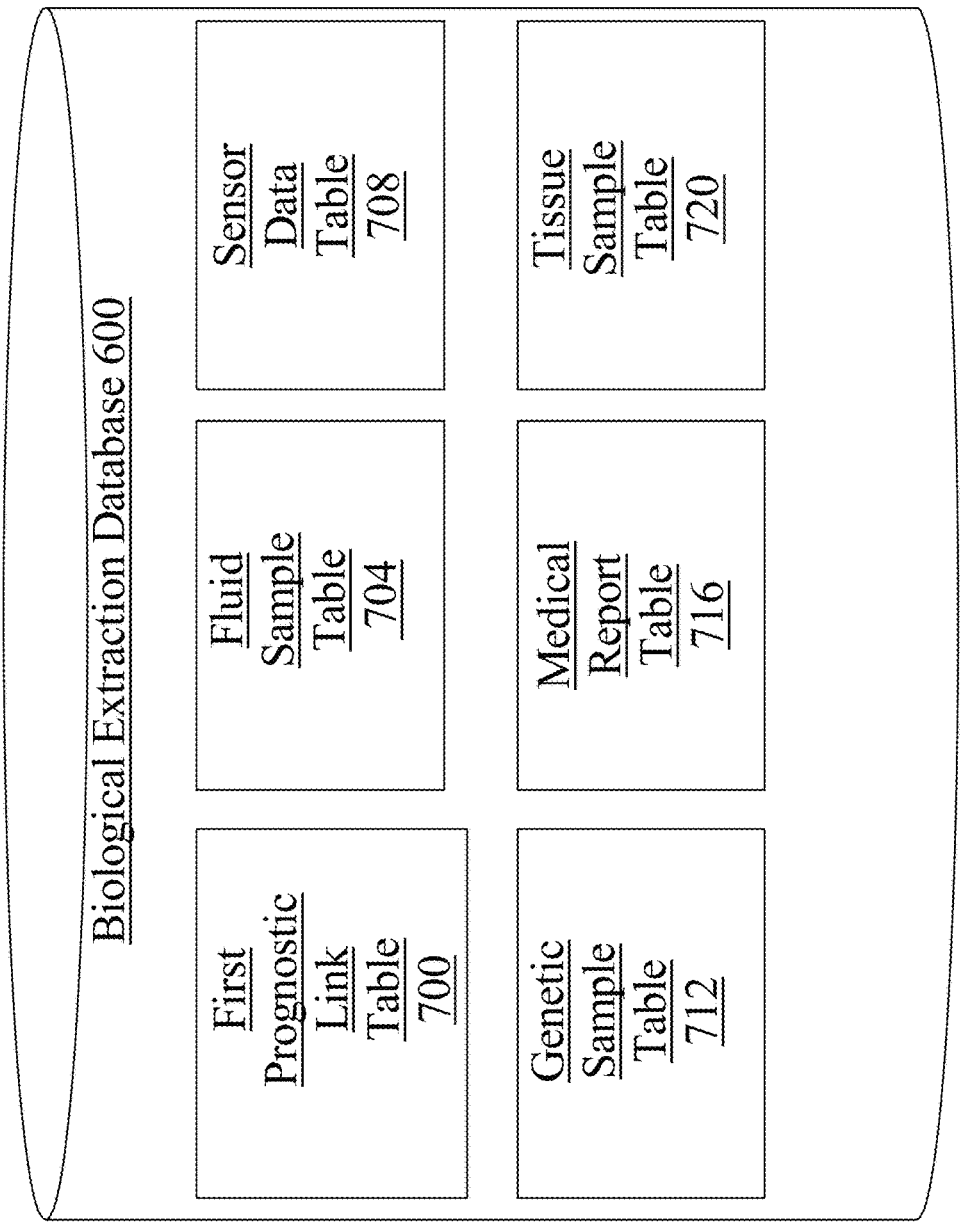
FIG. 7 is a block diagram illustrating an exemplary embodiment of a biological extraction database.

Referring now to FIG. 7, one or more database tables in biological extraction database 600 may include, as a non-limiting example, a first prognostic link table 700. First prognostic link table 700 may be a table relating biological extraction data as described above to prognostic labels; for instance, where an expert has entered data relating a prognostic label to a category of biological extraction data and/or to an element of biological extraction data via first graphical user interface 512 as described above, one or more rows recording such an entry may be inserted in first prognostic link table 700. Alternatively or additionally, linking of prognostic labels to biological extraction data may be performed entirely in a prognostic label database as described below.

With continued reference to FIG. 7, biological extraction database 600 may include tables listing one or more samples and/or biological extractions according to sample source. For instance, and without limitation, biological extraction database 600 may include a fluid sample table 704 listing samples acquired from a person by extraction of fluids, such as without limitation blood, lymph cerebrospinal fluid, or the like. As another non-limiting example, biological extraction database 600 may include a sensor data table 708, which may list samples acquired using one or more sensors, for instance as described in further detail below. As a further non-limiting example, biological extraction database 600 may include a genetic sample table 712, which may list partial or entire sequences of genetic material. Genetic material may be extracted and amplified, as a non-limiting example, using polymerase chain reactions (PCR) or the like. As a further example, also non-limiting, biological extraction database 600 may include a medical report table 716, which may list textual descriptions of medical tests, including without limitation radiological tests or tests of strength and/or dexterity or the like. Data in medical report table may be sorted and/or categorized using a language processing module 516, for instance, translating a textual description into a numerical value and a label corresponding to a category of physiological data; this may be performed using any language processing algorithm or algorithms as referred to in this disclosure. As another non-limiting example, biological extraction database 600 may include a tissue sample table 720, which may record biological extractions obtained using tissue samples. Tables presented above are presented for exemplary purposes only; persons skilled in the art will be aware of various ways in which data may be organized in biological extraction database 600 consistently with this disclosure.

Referring again to FIG. 6, diagnostic engine 108 and/or another device in diagnostic engine 108 may populate one or more fields in biological extraction database 600 using expert information, which may be extracted or retrieved from an expert knowledge database 604. An expert knowledge database 604 may include any data structure and/or data store suitable for use as a biological extraction database 600 as described above. Expert knowledge database 604 may include data entries reflecting one or more expert submissions of data such as may have been submitted according to any process described above, including without limitation by using first graphical user interface 512 and/or second graphical user interface 532. Expert knowledge database may include one or more fields generated by language processing module 516, such as without limitation fields extracted from one or more documents as described above. For instance, and without limitation, one or more categories of physiological data and/or related prognostic labels and/or categories of prognostic labels associated with an element of physiological state data as described above may be stored in generalized from in an expert knowledge database 604 and linked to, entered in, or associated with entries in a biological extraction database 600. Documents may be stored and/or retrieved by diagnostic engine 108 and/or language processing module 516 in and/or from a document database 608; document database 608 may include any data structure and/or data store suitable for use as biological extraction database 600 as described above. Documents in document database 608 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

Figure 8:
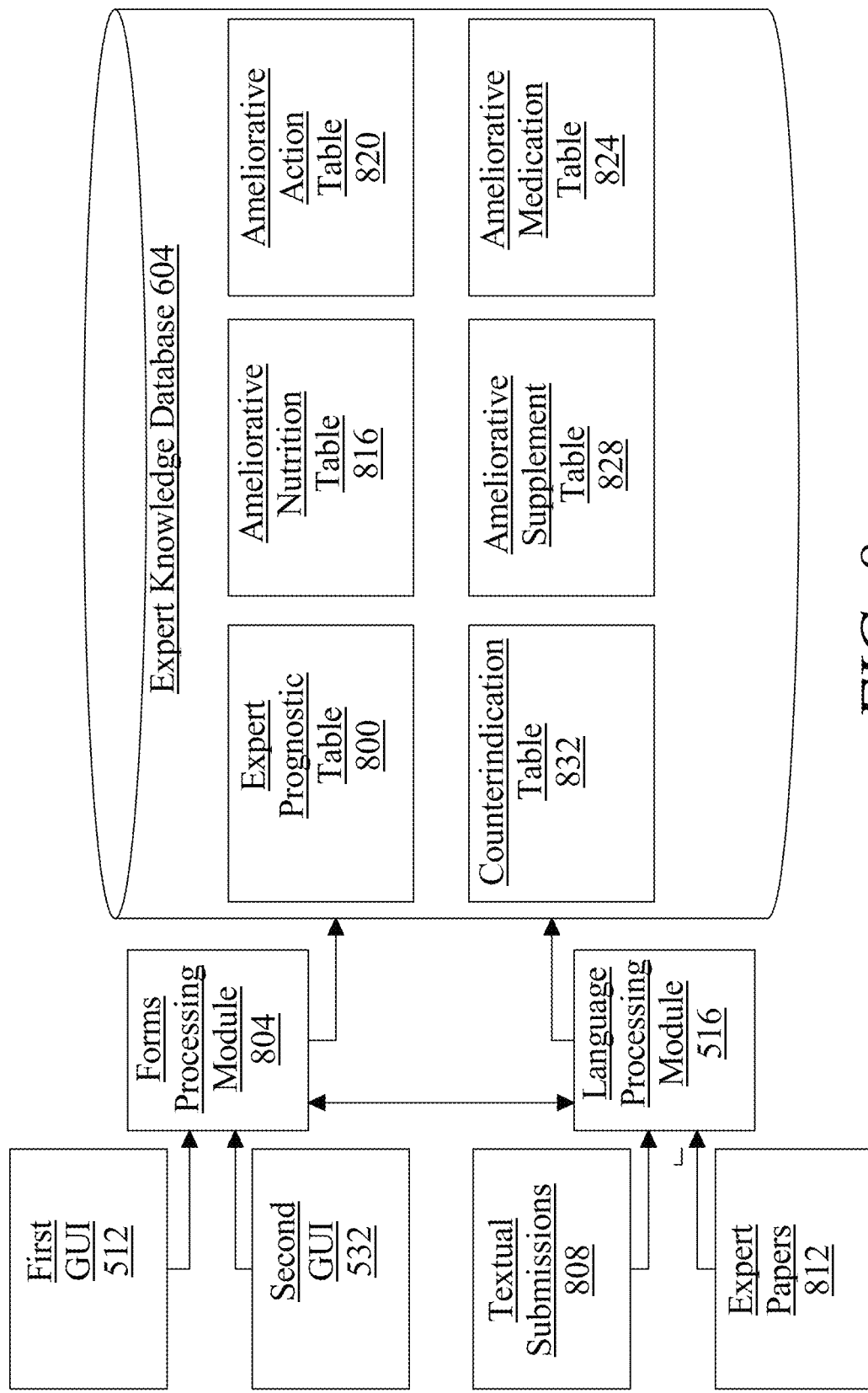
FIG. 8 is a block diagram illustrating an exemplary embodiment of an expert knowledge database.

Referring now to FIG. 8, an exemplary embodiment of an expert knowledge database 604 is illustrated. Expert knowledge database 604 may, as a non-limiting example, organize data stored in the expert knowledge database 604 according to one or more database tables. One or more database tables may be linked to one another by, for instance, common column values. For instance, a common column between two tables of expert knowledge database 604 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 8, one or more database tables in expert knowledge database 604 may include, as a non-limiting example, an expert prognostic table 800. Expert prognostic table 800 may be a table relating biological extraction data as described above to prognostic labels; for instance, where an expert has entered data relating a prognostic label to a category of biological extraction data and/or to an element of biological extraction data via first graphical user interface 512 as described above, one or more rows recording such an entry may be inserted in expert prognostic table 800. In an embodiment, a forms processing module 804 may sort data entered in a submission via first graphical user interface 512 by, for instance, sorting data from entries in the first graphical user interface 512 to related categories of data; for instance, data entered in an entry relating in the first graphical user interface 512 to a prognostic label may be sorted into variables and/or data structures for storage of prognostic labels, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 516 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 808, such as accomplished by filling out a paper or PDF form and/or submitting narrative information, may likewise be processed using language processing module 516. Data may be extracted from expert papers 812, which may include without limitation publications in medical and/or scientific journals, by language processing module 516 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert prognostic table 800 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 8, one or more database tables in expert knowledge database 604 may include, as a further non-limiting example tables listing one or more alimentary instruction set process labels; expert data populating such tables may be provided, without limitation, using any process described above, including entry of data from second graphical user interface 532 via forms processing module 804 and/or language processing module 516, processing of textual submissions 808, or processing of expert papers 812. For instance, and without limitation, an ameliorative alimentary table 816 may list one or more alimentary instruction set processes based on alimentary instructions, and/or links of such one or more alimentary instruction set processes to prognostic labels, as provided by experts according to any method of processing and/or entering expert data as described above. As a further example an ameliorative action table 820 may list one or more alimentary instruction set processes based on instructions for actions a user should take, including without limitation exercise, meditation, and/or cessation of harmful eating, substance abuse, or other habits, and/or links of such one or more alimentary instruction set processes to prognostic labels, as provided by experts according to any method of processing and/or entering expert data as described above. As an additional example, an ameliorative supplement table 828 may list one or more alimentary instruction set processes based on alimentary supplements, such as vitamin pills or the like, and/or links of such one or more alimentary instruction set processes to prognostic labels, as provided by experts according to any method of processing and/or entering expert data as described above. As a further non-limiting example, an ameliorative supplement table 828 may list one or more alimentary instruction set processes based on medications, including without limitation pharmaceutical drugs, and/or links of such one or more alimentary instruction set processes to prognostic labels, as provided by experts according to any method of processing and/or entering expert data as described above. As an additional example, a counterindication table 832 may list one or more counterindications for one or more alimentary instruction set processes; counterindications may include, without limitation allergies to one or more foods, medications, and/or supplements, side-effects of one or more medications and/or supplements, interactions between medications, foods, and/ or supplements, exercises that should not be given one or more medical conditions, injuries, disabilities, and/or demographic categories, or the like. Tables presented above are presented for exemplary purposes only; persons skilled in the art will be aware of various ways in which data may be organized in expert knowledge database 604 consistently with this disclosure.

Referring again to FIG. 6, a prognostic label database 512, which may be implemented in any manner suitable for implementation of biological extraction database 600, may be used to store prognostic labels used in diagnostic engine 108, including any prognostic labels correlated with elements of physiological data in first training set 500 as described above; prognostic labels may be linked to or refer to entries in biological extraction database 600 to which prognostic labels correspond. Linking may be performed by reference to historical data concerning biological extractions, such as diagnoses, prognoses, and/or other medical conclusions derived from biological extractions in the past; alternatively or additionally, a relationship between a prognostic label and a data entry in biological extraction database 600 may be determined by reference to a record in an expert knowledge database 604 linking a given prognostic label to a given category of biological extraction as described above. Entries in prognostic label database 612 may be associated with one or more categories of prognostic labels as described above, for instance using data stored in and/or extracted from an expert knowledge database 604.

Figure 9:
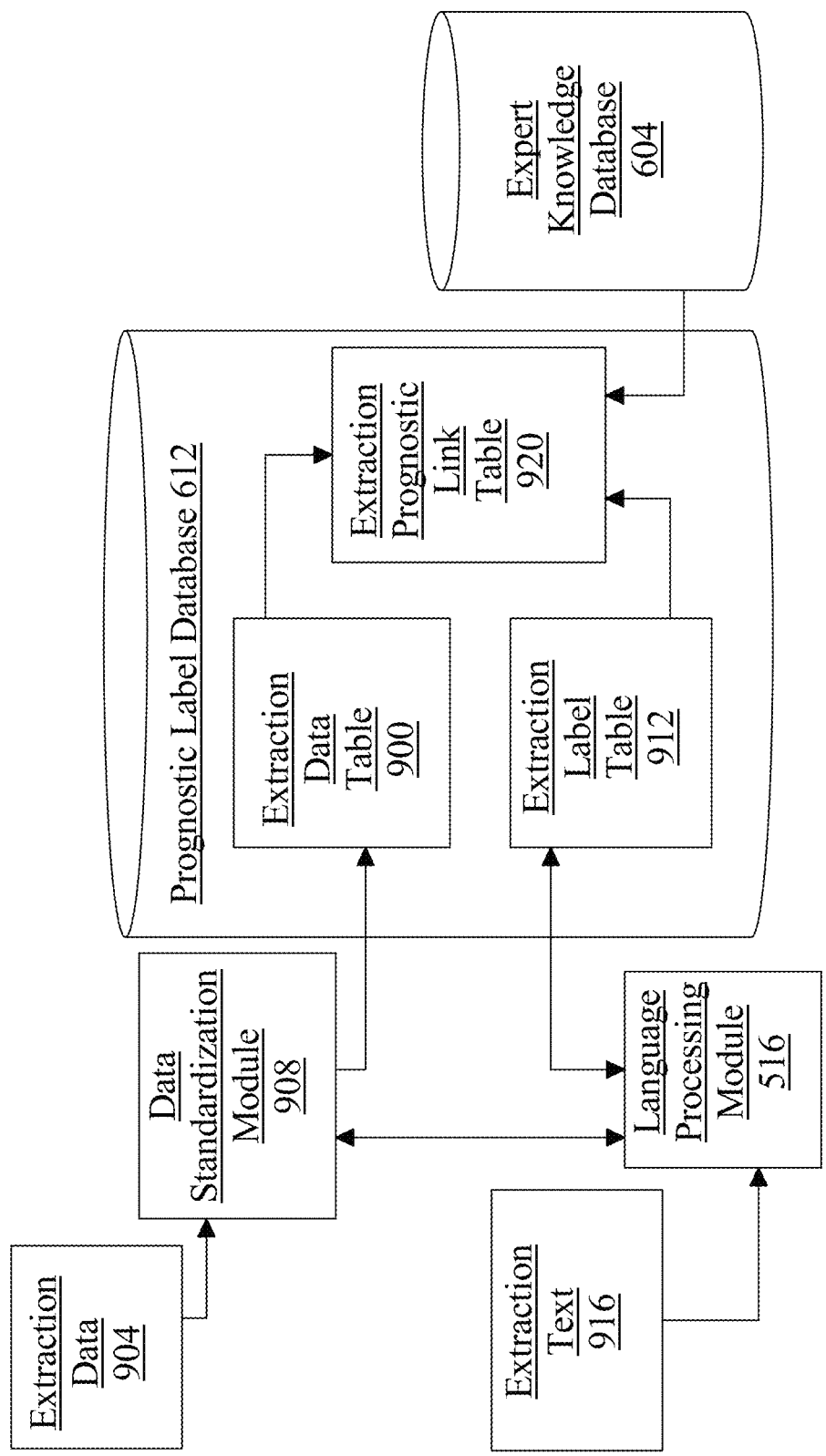
FIG. 9 is a block diagram illustrating an exemplary embodiment of a prognostic label database.

Referring now to FIG. 9, an exemplary embodiment of a prognostic label database 612 is illustrated. Prognostic label database 612 may, as a non-limiting example, organize data stored in the prognostic label database 612 according to one or more database tables. One or more database tables may be linked to one another by, for instance, common column values. For instance, a common column between two tables of prognostic label database 612 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 9, one or more database tables in prognostic label database 612 may include, as a non-limiting example, an extraction data table 900. Extraction data table 900 may be a table listing sample data, along with, for instance, one or more linking columns to link such data to other information stored in prognostic label database 512. In an embodiment, extraction data 804 may be acquired, for instance from biological extraction database 600, in a raw or unsorted form, and may be translated into standard forms, such as standard units of measurement, labels associated with particular physiological data values, or the like; this may be accomplished using a data standardization module 808, which may perform unit conversions. Data standardization module 808 may alternatively or additionally map textual information, such as labels describing values tested for or the like, using language processing module 516 or equivalent components and/or algorithms thereto.

Continuing to refer to FIG. 9, prognostic label database 612 may include an extraction label table 912; extraction label table 912 may list prognostic labels received with and/or extracted from biological extractions, for instance as received in the form of extraction text 916. A language processing module 516 may compare textual information so received to prognostic labels and/or form new prognostic labels according to any suitable process as described above. Extraction prognostic link table 920 may combine extractions with prognostic labels, as acquired from extraction label table and/or expert knowledge database 604; combination may be performed by listing together in rows or by relating indices or common columns of two or more tables to each other. Tables presented above are presented for exemplary purposes only; persons skilled in the art will be aware of various ways in which data may be organized in expert knowledge database 604 consistently with this disclosure.

Referring again to FIG. 6, first training set 500 may be populated by retrieval of one or more records from biological extraction database 600 and/or prognostic label database 512; in an embodiment, entries retrieved from biological extraction database 600 and/or prognostic label database 612 may be filtered and or select via query to match one or more additional elements of information as described above, so as to retrieve a first training set 500 including data belonging to a given cohort, demographic population, or other set, so as to generate outputs as described below that are tailored to a person or persons with regard to whom diagnostic engine 108 classifies biological extractions to prognostic labels as set forth in further detail below. Persons skilled in the art, upon reviewing the entirety of this disclosure, will be aware of various ways in which records may be retrieved from biological extraction database 600 and/or prognostic label database to generate a first training set to reflect individualized group data pertaining to a person of interest in operation of system and/or method, including without limitation a person with regard to whom at least a biological extraction is being evaluated as described in further detail below. Diagnostic engine 108 may alternatively or additionally receive a first training set 500 and store one or more entries in biological extraction database 600 and/or prognostic label database 612 as extracted from elements of first training set 500.

Still referring to FIG. 6, diagnostic engine 108 may include or communicate with an ameliorative process label database 516; an ameliorative process label database 616 may include any data structure and/or datastore suitable for use as a biological extraction database 600 as described above. An ameliorative process label database 616 may include one or more entries listing labels associated with one or more alimentary instruction set processes as described above, including any alimentary instruction set labels correlated with prognostic labels in second training set 520 as described above; alimentary instruction set process labels may be linked to or refer to entries in prognostic label database 612 to which alimentary instruction set process labels correspond. Linking may be performed by reference to historical data concerning prognostic labels, such as therapies, food coaching/nutrition counseling, treatments, and/or lifestyle or dietary choices chosen to alleviate conditions associated with prognostic labels in the past; alternatively or additionally, a relationship between an alimentary instruction set process label and a data entry in prognostic label database 612 may be determined by reference to a record in an expert knowledge database 604 linking a given alimentary instruction set process label to a given category of prognostic label as described above. Entries in prognostic label database 612 may be associated with one or more categories of prognostic labels as described above, for instance using data stored in and/or extracted from an expert knowledge database 604.

Figure 10:
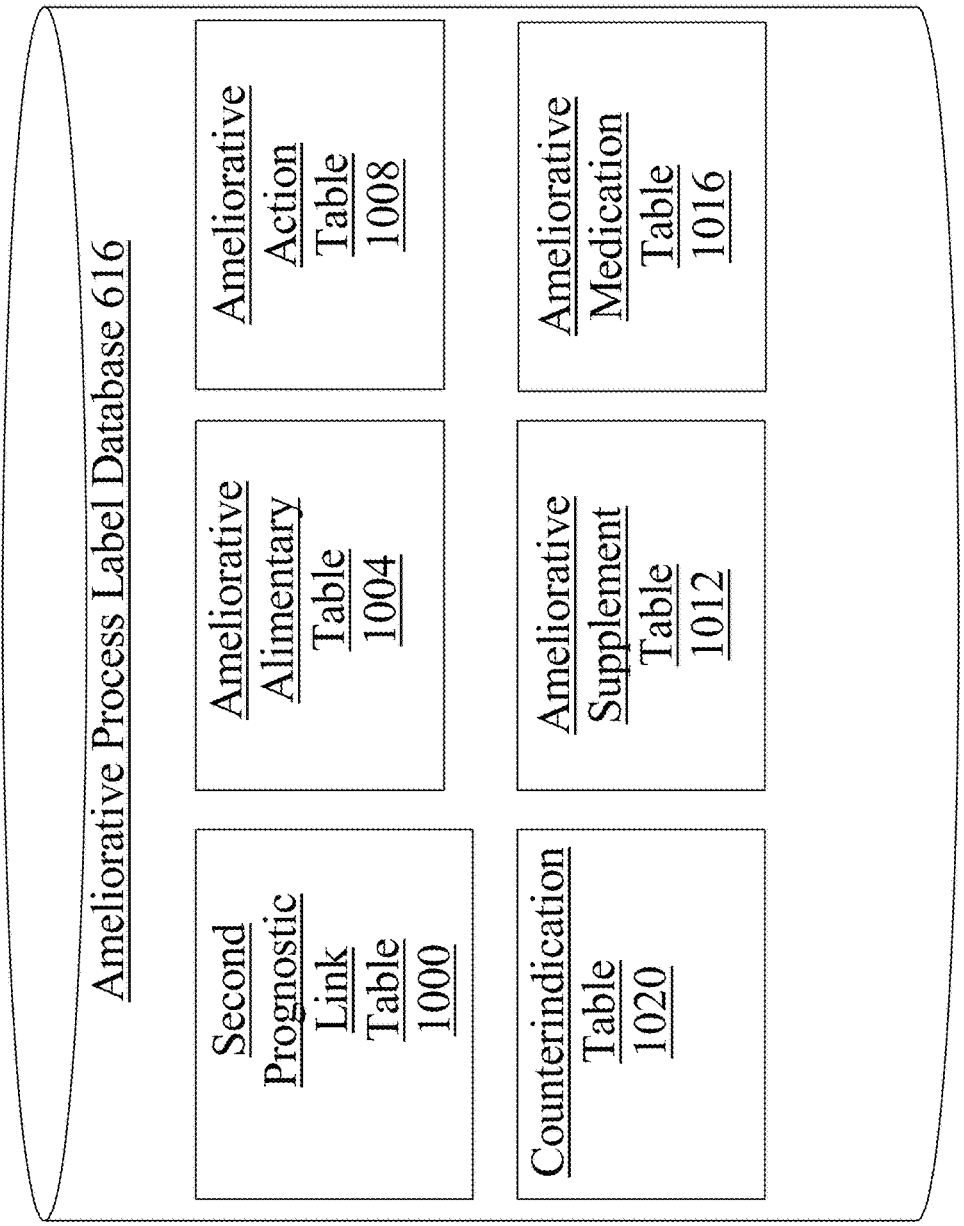
FIG. 10 is a block diagram illustrating an exemplary embodiment of an alimentary instruction set label database.

Referring now to FIG. 10, an exemplary embodiment of an ameliorative process label database 616 is illustrated. Ameliorative process label database 616 may, as a non-limiting example, organize data stored in the ameliorative process label database 616 according to one or more database tables. One or more database tables may be linked to one another by, for instance, common column values. For instance, a common column between two tables of ameliorative process label database 616 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 10, ameliorative process label database 616 may include a second prognostic link table 1000; second prognostic link table 1000 may link ameliorative process data to prognostic label data, using any suitable method for linking data in two or more tables as described above. Ameliorative process label database 616 may include an ameliorative alimentary table 1004, which may list one or more alimentary instruction set processes based on alimentary instructions, and/or links of such one or more alimentary instruction set processes to prognostic labels, for instance as provided by experts according to any method of processing and/or entering expert data as described above, and/or using one or more machine-learning processes as set forth in further detail below. As a further example an ameliorative action table 1008 may list one or more alimentary instruction set processes based on instructions for actions a user should take, including without limitation cessation of harmful eating, substance abuse, or other habits, and/or links of such one or more alimentary instruction set processes to prognostic labels, as provided by experts according to any method of processing and/or entering expert data as described above and/or using one or more machine-learning processes as set forth in further detail below. As an additional example, an ameliorative supplement table 1012 may list one or more alimentary instruction set processes based on alimentary supplements, such as vitamin pills or the like, and/or links of such one or more alimentary instruction set processes to prognostic labels, as provided by experts according to any method of processing and/or entering expert data as described above and/or using one or more machine-learning processes as set forth in further detail below. As a further non-limiting example, an ameliorative medication table 916 may list one or more alimentary instruction set processes based on medications, including without limitation pharmaceutical drugs, and/or links of such one or more alimentary instruction set processes to prognostic labels, as provided by experts according to any method of processing and/or entering expert data as described above and/or using one or more machine-learning processes as set forth in further detail below. As an additional example, a counterindication table 920 may list one or more counter-indications for one or more alimentary instruction set processes; counterindications may include, without limitation allergies to one or more foods, medications, and/or supplements, side-effects of one or more medications and/or supplements, interactions between medications, foods, and/or supplements, or the like; this may be acquired using expert submission as described above and/or using one or more machine-learning processes as set forth in further detail below. Tables presented above are presented for exemplary purposes only; persons skilled in the art will be aware of various ways in which data may be organized in databases of system 100 consistently with this disclosure.

Referring again to FIG. 6, second training set 520 may be populated by retrieval of one or more records from prognostic label database 612 and/or ameliorative process label database 516; in an embodiment, entries retrieved from prognostic label database 612 and/or ameliorative process label database 616 may be filtered and or select via query to match one or more additional elements of information as described above, so as to retrieve a second training set 520 including data belonging to a given cohort, demographic population, or other set, so as to generate outputs as described below that are tailored to a person or persons with regard to whom diagnostic engine 108 classifies prognostic labels to alimentary instruction set process labels as set forth in further detail below. Persons skilled in the art, upon reviewing the entirety of this disclosure, will be aware of various ways in which records may be retrieved from prognostic label database 612 and/or ameliorative process label database 616 to generate a second training set 520 to reflect individualized group data pertaining to a person of interest in operation of system and/or method, including without limitation a person with regard to whom at least a biological extraction is being evaluated as described in further detail below. Diagnostic engine 108 may alternatively or additionally receive a second training set 520 and store one or more entries in prognostic label database 612 and/or ameliorative process label database 616 as extracted from elements of second training set 520.

In an embodiment, and still referring to FIG. 6, diagnostic engine 108 may receive an update to one or more elements of data represented in first training set 500 and/or second training set 520, and may perform one or more modifications to first training set 500 and/or second training set 520, or to biological extraction database 600, expert knowledge database 604, prognostic label database 512, and/or ameliorative process label database 616 as a result. For instance a biological extraction may turn out to have been erroneously recorded; diagnostic engine 108 may remove it from first training set 500, second training set 520, biological extraction database 600, expert knowledge database 604, prognostic label database 512, and/or ameliorative process label database 616 as a result. As a further example, a medical and/or academic paper, or a study on which it was based, may be revoked; diagnostic engine 108 may remove it from first training set 500, second training set 520, biological extraction database 600, expert knowledge database 604, prognostic label database 512, and/or ameliorative process label database 616 as a result. Information provided by an expert may likewise be removed if the expert loses credentials or is revealed to have acted fraudulently.

Continuing to refer to FIG. 7, elements of data first training set 500, second training set 520, biological extraction database 600, expert knowledge database 604, prognostic label database 512, and/or ameliorative process label database 616 may have temporal attributes, such as time-stamps; diagnostic engine 108 may order such elements according to recency, select only elements more recently entered for first training set 500 and/or second training set 520, or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Referring again to FIG. 6, diagnostic engine 108 may be configured to record at least a biological extraction. At least a biological extraction may include a physically extracted sample, which as used herein includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, at least a biological extraction may include a signal from at least a sensor configured to detect physiological data of a user and recording the at least a biological extraction as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of diagnostic engine 108 or may be a separate device in communication with diagnostic engine 108.

Still referring to FIG. 6, at least a biological extraction may include any data suitable for use as physiological state data as described above, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include one or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

Alternatively or additionally, and with continued reference to FIG. 6, at least a biological extraction may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

Still referring to FIG. 6, at least a biological extraction may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a biological extraction consistent with this disclosure. At least a biological extraction may be added to biological extraction database 600.

With continued reference to FIG. 6, diagnostic engine 108 may include a prognostic label learner 536 operating on the diagnostic engine 108, the prognostic label learner 536 designed and configured to generate the at least a prognostic output as a function of the first training set 500 and the at least a biological extraction. Prognostic label learner 536 may include any hardware and/or software module. Prognostic label learner 536 is designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Figure 11:
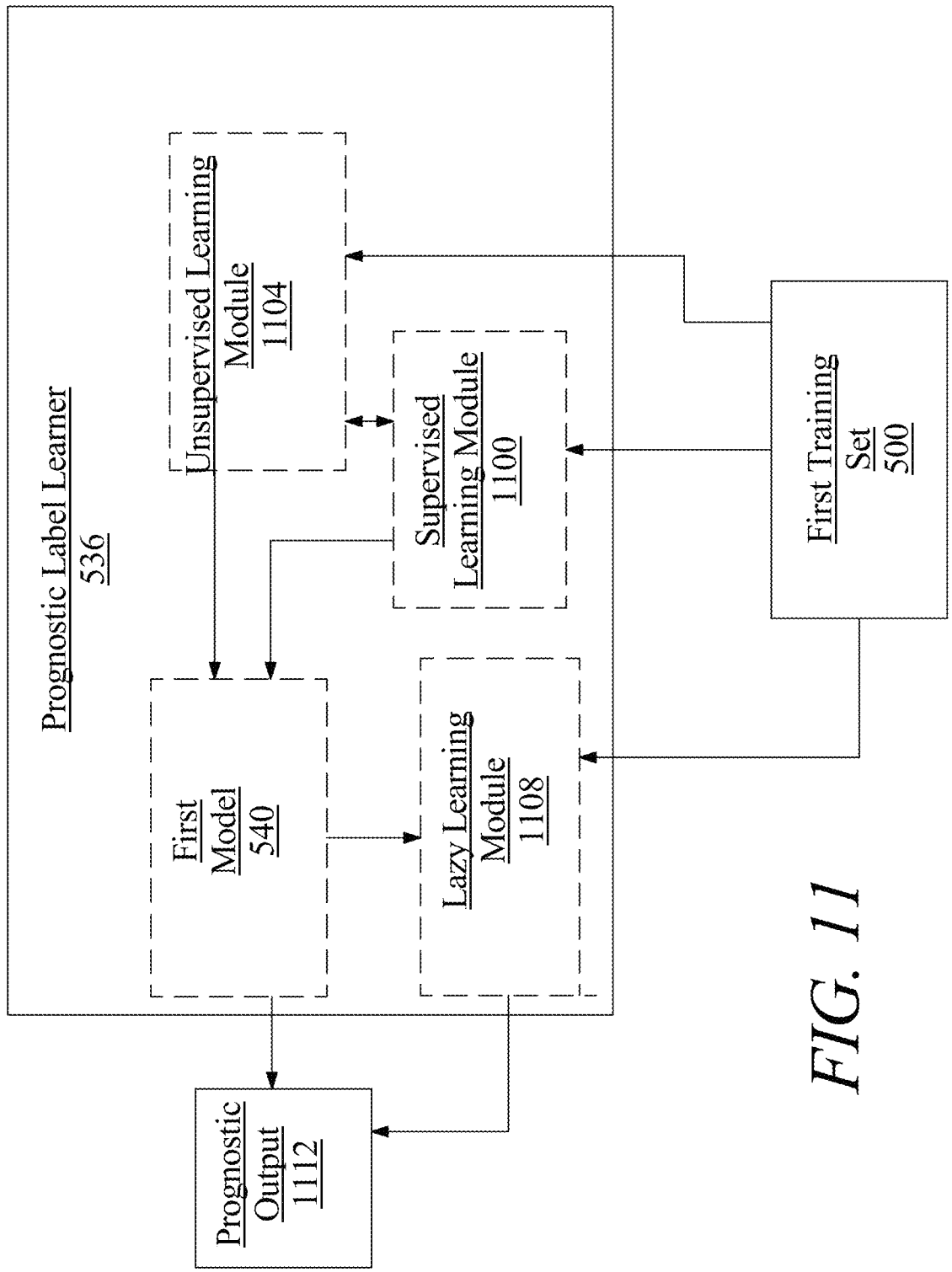
FIG. 11 is a block diagram illustrating an exemplary embodiment of a prognostic label learner and associated system elements.

Referring now to FIG. 11, prognostic label learner 536 may be designed and configured to generate at least a prognostic output by creating at least a first machine-learning model 540 relating physiological state data 504 to prognostic labels using the first training set 500 and generating the at least a prognostic output using the first machine-learning model 540; at least a first machine-learning model 540 may include one or more models that determine a mathematical relationship between physiological state data 504 and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 11, machine-learning algorithm used to generate first machine-learning model 540 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 11, prognostic label learner 536 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set 500; the trained network may then be used to apply detected relationships between elements of physiological state data 504 and prognostic labels.

Still referring to FIG. 11, machine-learning algorithms used by prognostic label learner 536 may include supervised machine-learning algorithms, which may, as a non-limiting example be executed using a supervised learning module 1100 executing on diagnostic engine 108 and/or on another computing device in communication with diagnostic engine 108, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological data as inputs, prognostic labels as outputs, and a scoring function representing a desired form of relationship to be detected between elements of physiological data and prognostic labels; scoring function may, for instance, seek to maximize the probability that a given element of physiological state data 504 and/or combination of elements of physiological data is associated with a given prognostic label and/or combination of prognostic labels to minimize the probability that a given element of physiological state data 504 and/or combination of elements of physiological state data 504 is not associated with a given prognostic label and/or combination of prognostic labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 500. Persons skilled in the art, upon reviewing the entirety of this disclosure, will be aware of various possible variations of supervised machine learning algorithms that may be used to determine relation between elements of physiological data and prognostic labels. In an embodiment, one or more supervised machine-learning algorithms may be restricted to a particular domain for instance, a supervised machine-learning process may be performed with respect to a given set of parameters and/or categories of parameters that have been suspected to be related to a given set of prognostic labels, and/or are specified as linked to a medical specialty and/or field of medicine covering a particular set of prognostic labels. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate prognostic labels. Additional supervised learning processes may be performed without domain restrictions to detect, for instance, previously unknown and/or unsuspected relationships between physiological data and prognostic labels.

Still referring to FIG. 11, machine-learning algorithms may include unsupervised processes; unsupervised processes may, as a non-limiting example, be executed by an unsupervised learning module 1104 executing on diagnostic engine 108 and/or on another computing device in communication with diagnostic engine 108, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, prognostic label learner 536 and/or diagnostic engine 108 may perform an unsupervised machine learning process on first training set 500, which may cluster data of first training set 500 according to detected relationships between elements of the first training set 500, including without limitation correlations of elements of physiological state data 504 to each other and correlations of prognostic labels to each other; such relations may then be combined with supervised machine learning results to add new criteria for prognostic label learner 536 to apply in relating physiological state data 504 to prognostic labels. As a non-limiting, illustrative example, an unsupervised process may determine that a first element of physiological data acquired in a blood test correlates closely with a second element of physiological data, where the first element has been linked via supervised learning processes to a given prognostic label, but the second has not; for instance, the second element may not have been defined as an input for the supervised learning process, or may pertain to a domain outside of a domain limitation for the supervised learning process. Continuing the example a close correlation between first element of physiological state data 504 and second element of physiological state data 504 may indicate that the second element is also a good predictor for the prognostic label; second element may be included in a new supervised process to derive a relationship or may be used as a synonym or proxy for the first physiological element by prognostic label learner 536.

Still referring to FIG. 11, diagnostic engine 108 and/or prognostic label learner 536 may detect further significant categories of physiological data, relationships of such categories to prognostic labels, and/or categories of prognostic labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to diagnostic engine 108, prognostic label learner 536 and/or diagnostic engine 108 may continuously or iteratively perform unsupervised machine-learning processes to detect relationships between different elements of the added and/or overall data; in an embodiment, this may enable diagnostic engine 108 to use detected relationships to discover new correlations between known biomarkers, prognostic labels, and/or alimentary instruction set labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular prognostic labels and/or suitable alimentary instruction set labels. Use of unsupervised learning may greatly enhance the accuracy and detail with which system may detect prognostic labels and/or alimentary instruction set labels.

With continued reference to FIG. 11, unsupervised processes may be subjected to domain limitations. For instance, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of prognostic label, and/or a group of people having a shared value and/or category of alimentary instruction set label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 11, prognostic label learner 536 may alternatively or additionally be designed and configured to generate at least a prognostic output by executing a lazy learning process as a function of the first training set 500 and the at least a biological extraction; lazy learning processes may be performed by a lazy learning module 1108 executing on diagnostic engine 108 and/or on another computing device in communication with diagnostic engine 108, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a prognostic label associated with biological extraction, using first training set 500. As a non-limiting example, an initial heuristic may include a ranking of prognostic labels according to relation to a test type of at least a biological extraction, one or more categories of physiological data identified in test type of at least a biological extraction, and/or one or more values detected in at least a biological extraction; ranking may include, without limitation, ranking according to significance scores of associations between elements of physiological data and prognostic labels, for instance as calculated as described above. Heuristic may include selecting some number of highest-ranking associations and/or prognostic labels. Prognostic label learner 536 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate prognostic outputs as described in this disclosure, including without limitation lazy learning applications of machine-learning algorithms as described in further detail below.

In an embodiment, and continuing to refer to FIG. 11, prognostic label learner 536 may generate a plurality of prognostic labels having different implications for a particular person. For instance, where the at least a biological extraction includes a result of a dexterity test, a low score may be consistent with amyotrophic lateral sclerosis, Parkinson's disease, multiple sclerosis, and/or any number of less sever disorders or tendencies associated with lower levels of dexterity. In such a situation, prognostic label learner 536 and/or diagnostic engine 108 may perform additional processes to resolve ambiguity. Processes may include presenting multiple possible results to a medical practitioner, informing the medical practitioner that one or more follow-up tests and/or biological extractions are needed to further determine a more definite prognostic label. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, prognostic label learner 536 and/or diagnostic engine 108 may operate a further algorithm to determine which of the multiple outputs is most likely to be correct; algorithm may include use of an additional supervised and/or unsupervised model. Alternatively or additionally, prognostic label learner 536 may perform one or more lazy learning processes using a more comprehensive set of user data to identify a more probably correct result of the multiple results. Results may be presented and/or retained with rankings, for instance to advise a medical professional of the relative probabilities of various prognostic labels being correct; alternatively or additionally, prognostic labels associated with a probability of correctness below a given threshold and/or prognostic labels contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of prognostic labels associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of prognostic labels on a list of multiple prognostic labels, and/or to eliminate some labels from such a list. Prognostic output 1112 may be provided to user output device as described in further detail below.

Figure 12:
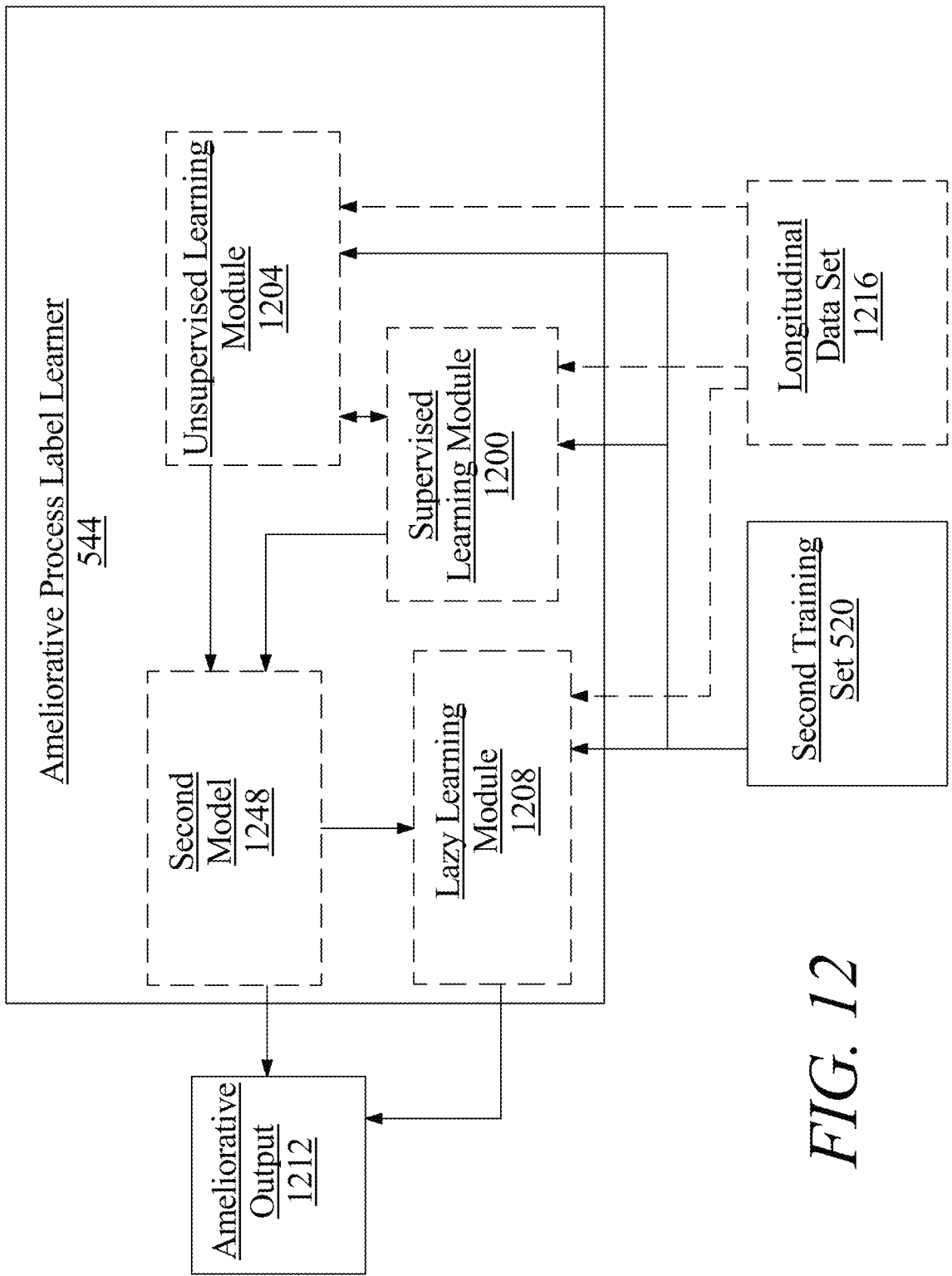
FIG. 12 is a block diagram illustrating an exemplary embodiment of an ameliorative process label learner and associated system elements.

Referring now to FIG. 12, diagnostic engine 108 includes an ameliorative process label learner 544 operating on the diagnostic engine 108, the ameliorative process label learner 544 designed and Referring again to FIG. 5, diagnostic engine 108 may include an ameliorative process label learner 544 operating on the diagnostic engine 108, the ameliorative process label learner 544 designed and configured to generate the at least an ameliorative output as a function of the second training set 520 and the at least a prognostic output. Ameliorative process label learner 544 may include any hardware or software module suitable for use as a prognostic label learner 536 as described above. Ameliorative process label learner 544 is a machine-learning module as described above; ameliorative process label learner 544 may perform any machine-learning process or combination of processes suitable for use by a prognostic label learner 536 as described above. For instance, and without limitation, and ameliorative process label learner 544 may be configured to create a second machine-learning model 548 relating prognostic labels to ameliorative labels using the second training set 520 and generate the at least an ameliorative output using the second machine-learning model 548; second machine-learning model 548 may be generated according to any process, process steps, or combination of processes and/or process steps suitable for creation of first machine learning model. In an embodiment, ameliorative process label learner 544 may use data from first training set 500 as well as data from second training set 520; for instance, ameliorative process label learner 544 may use lazy learning and/or model generation to determine relationships between elements of physiological data, in combination with or instead of prognostic labels, and ameliorative labels. Where ameliorative process label learner 544 determines relationships between elements of physiological data and ameliorative labels directly, this may determine relationships between prognostic labels and ameliorative labels as well owing to the existence of relationships determined by prognostic label learner 536.

Referring again to FIG. 12, ameliorative process label learner 544 may be configured to perform one or more supervised learning processes, as described above; supervised learning processes may be performed by a supervised learning module 1200 executing on diagnostic engine 108 and/or on another computing device in communication with diagnostic engine 108, which may include any hardware or software module. For instance, a supervised learning algorithm may use prognostic labels as inputs, ameliorative labels as outputs, and a scoring function representing a desired form of relationship to be detected between prognostic labels and ameliorative labels; scoring function may, for instance, seek to maximize the probability that a given prognostic label and/or combination of prognostic labels is associated with a given ameliorative label and/or combination of ameliorative labels to minimize the probability that a given prognostic label and/or combination of prognostic labels is not associated with a given ameliorative label and/or combination of ameliorative labels. In an embodiment, one or more supervised machine-learning algorithms may be restricted to a particular domain; for instance, a supervised machine-learning process may be performed with respect to a given set of parameters and/or categories of prognostic labels that have been suspected to be related to a given set of ameliorative labels, for instance because the ameliorative processes corresponding to the set of ameliorative labels are hypothesized or suspected to have an ameliorative effect on conditions represented by the prognostic labels, and/or are specified as linked to a medical specialty and/or field of medicine covering a particular set of prognostic labels and/or ameliorative labels. As a nonlimiting example, a particular set prognostic labels corresponding to a set of cardiovascular conditions may be typically treated by cardiologists, and a supervised machine-learning process may be performed to relate those prognostic labels to ameliorative labels associated with various treatment options, medications, and/or lifestyle changes.

With continued reference to FIG. 12, ameliorative process label learner 544 may perform one or more unsupervised machine-learning processes as described above; unsupervised processes may be performed by an unsupervised learning module 1204 executing on diagnostic engine 108 and/or on another computing device in communication with diagnostic engine 108, which may include any hardware or software module. For instance, and without limitation, ameliorative process label learner 544 and/or diagnostic engine 108 may perform an unsupervised machine learning process on second training set 520, which may cluster data of second training set 520 according to detected relationships between elements of the second training set 520, including without limitation correlations of prognostic labels to each other and correlations of ameliorative labels to each other; such relations may then be combined with supervised machine learning results to add new criteria for ameliorative process label learner 544 to apply in relating prognostic labels to ameliorative labels. As a non-limiting, illustrative example, an unsupervised process may determine that a first prognostic label 508 correlates closely with a second prognostic label 524, where the first prognostic label 508 has been linked via supervised learning processes to a given ameliorative label, but the second has not; for instance, the second prognostic label 524 may not have been defined as an input for the supervised learning process, or may pertain to a domain outside of a domain limitation for the supervised learning process. Continuing the example, a close correlation between first prognostic label 508 and second prognostic label 524 may indicate that the second prognostic label 524 is also a good match for the ameliorative label; second prognostic label 524 may be included in a new supervised process to derive a relationship or may be used as a synonym or proxy for the first prognostic label 508 by ameliorative process label learner 544. Unsupervised processes performed by ameliorative process label learner 544 may be subjected to any domain limitations suitable for unsupervised processes performed by prognostic label learner 536 as described above.

Still referring to FIG. 12, diagnostic engine 108 and/or ameliorative process label learner 544 may detect further significant categories of prognostic labels, relationships of such categories to ameliorative labels, and/or categories of ameliorative labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to diagnostic engine 108, ameliorative process label learner 544 and/or diagnostic engine 108 may continuously or iteratively perform unsupervised machine-learning processes to detect relationships between different elements of the added and/or overall data; in an embodiment, this may enable diagnostic engine 108 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

Continuing to view FIG. 12, ameliorative process label learner 544 may be configured to perform a lazy learning process as a function of the second training set 520 and the at least a prognostic output to produce the at least an ameliorative output; a lazy learning process may include any lazy learning process as described above regarding prognostic label learner 436. Lazy learning processes may be performed by a lazy learning module 1208 executing on diagnostic engine 108 and/or on another computing device in communication with diagnostic engine 108, which may include any hardware or software module. Ameliorative output 1212 may be provided to a user output device as described in further detail below.

In an embodiment, and still referring to FIG. 12, ameliorative process label learner 544 may generate a plurality of ameliorative labels having different implications for a particular person. For instance, where a prognostic label indicates that a person has a magnesium deficiency, various dietary choices may be generated as ameliorative labels associated with correcting the deficiency, such as ameliorative labels associated with consumption of almonds, spinach, and/or dark chocolate, as well as ameliorative labels associated with consumption of magnesium supplements. In such a situation, ameliorative process label learner 544 and/or diagnostic engine 108 may perform additional processes to resolve ambiguity. Processes may include presenting multiple possible results to a medical practitioner, informing the medical practitioner of various options that may be available, and/or that follow-up tests, procedures, or counseling may be required to select an appropriate choice. Alternatively or additionally, processes may include additional machine learning steps. For instance, ameliorative process label learner 544 may perform one or more lazy learning processes using a more comprehensive set of user data to identify a more probably correct result of the multiple results. Results may be presented and/or retained with rankings, for instance to advise a medical professional of the relative probabilities of various ameliorative labels being correct or ideal choices for a given person; alternatively or additionally, ameliorative labels associated with a probability of success or suitability below a given threshold and/or ameliorative labels contradicting results of the additional process, may be eliminated. As a non-limiting example, an additional process may reveal that a person is allergic to tree nuts, and consumption of almonds may be eliminated as an ameliorative label to be presented.

Continuing to refer to FIG. 12, ameliorative process label learner 544 may be designed and configured to generate further training data and/or to generate outputs using longitudinal data 1216. As used herein, longitudinal data 1216 may include a temporally ordered series of data concerning the same person, or the same cohort of persons; for instance, longitudinal data 1216 may describe a series of blood samples taken one day or one month apart over the course of a year. Longitudinal data 1216 may related to a series of samples tracking response of one or more elements of physiological data recorded regarding a person undergoing one or more ameliorative processes linked to one or more ameliorative process labels. Ameliorative process label learner 544 may track one or more elements of physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given ameliorative process over time on a physiological parameter. Functions may be compared to each other to rank ameliorative processes; for instance, an ameliorative process associated with a steeper slope in curve representing improvement in a physiological data element, and/or a shallower slope in a curve representing a slower decline, may be ranked higher than an ameliorative process associated with a less steep slope for an improvement curve or a steeper slope for a curve marking a decline. Ameliorative processes associated with a curve and/or terminal data point representing a value that does not associate with a previously detected prognostic label may be ranked higher than one that is not so associated. Information obtained by analysis of longitudinal data 1216 may be added to ameliorative process database and/or second training set.

Referring again to FIG. 6, diagnostic engine 108 may include an alimentary instruction label learner 552 operating on the diagnostic engine 108, the alimentary instruction label learner 552 designed and configured to generate at least an alimentary data output as a function of the second training set 520 and the at least a prognostic output. Alimentary instruction label learner 552 may include any hardware or software module suitable for use as a prognostic label learner 536 as described above. Alimentary instruction label learner 552 may include a machine-learning module as described above; alimentary instruction label learner 552 may perform any machine-learning process or combination of processes suitable for use by a prognostic label learner 536 as described above. For instance, and without limitation, and alimentary instruction label learner 552 may be configured to create a third machine-learning model 556 relating prognostic labels to alimentary labels using the second training set 520 and generate the at least an alimentary data output using the third machine-learning model 456; third machine-learning model 556 may be generated according to any process, process steps, or combination of processes and/or process steps suitable for creation of first machine learning model. In an embodiment, alimentary instruction label learner 552 may use data from first training set 500 as well as data from second training set 520; for instance, alimentary instruction label learner 552 may use lazy learning and/or model generation to determine relationships between elements of physiological data, in combination with or instead of prognostic labels, and alimentary labels, which may include, without limitation, a subset of ameliorative labels corresponding to alimentary processes. Where alimentary instruction label learner 552 determines relationships between elements of physiological data and alimentary labels directly, this may determine relationships between prognostic labels and alimentary labels as well owing to the existence of relationships determined by prognostic label learner 536.

Figure 13:
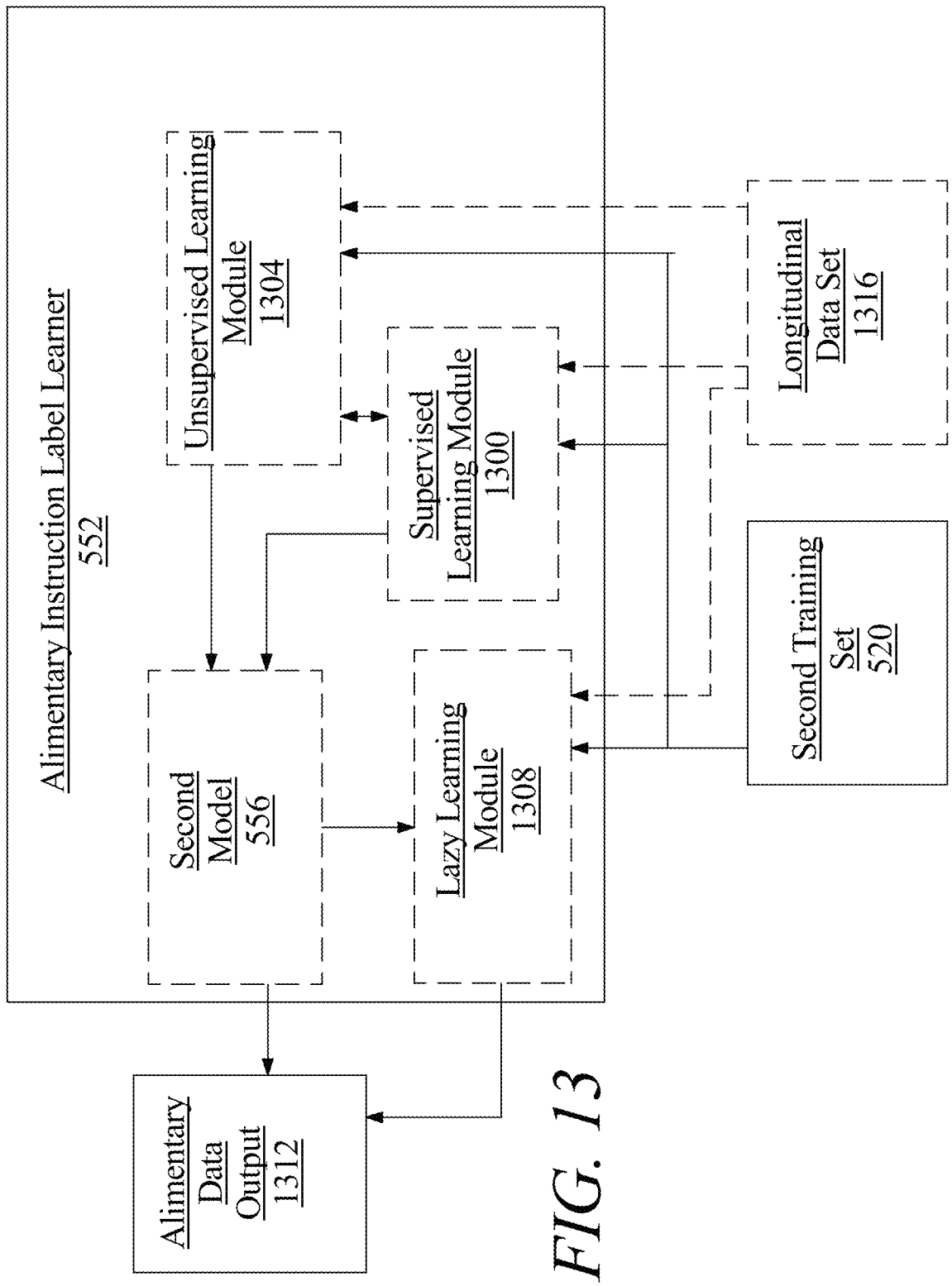
FIG. 13 is a block diagram illustrating an exemplary embodiment of an alimentary instruction label learner and associated system elements.

Referring now to FIG. 13, alimentary instruction label learner 552 may be configured to perform one or more supervised learning processes, as described above; supervised learning processes may be performed by a supervised learning module 1300 executing on diagnostic engine 108 and/or on another computing device in communication with diagnostic engine 108, which may include any hardware or software module. For instance, a supervised learning algorithm may use prognostic labels as inputs, alimentary labels as outputs, and a scoring function representing a desired form of relationship to be detected between prognostic labels and alimentary labels; scoring function may, for instance, seek to maximize the probability that a given prognostic label and/or combination of prognostic labels is associated with a given alimentary label and/or combination of alimentary labels to minimize the probability that a given prognostic label and/or combination of prognostic labels is not associated with a given alimentary label and/or combination of alimentary labels. In an embodiment, one or more supervised machine-learning algorithms may be restricted to a particular domain; for instance, a supervised machine-learning process may be performed with respect to a given set of parameters and/or categories of prognostic labels that have been suspected to be related to a given set of alimentary labels, for instance because the alimentary processes corresponding to the set of alimentary labels are hypothesized or suspected to have an ameliorative effect on conditions represented by the prognostic labels, and/or are specified as linked to a medical specialty and/or field of medicine covering a particular set of prognostic labels and/or alimentary labels. As a non-limiting example, a particular set prognostic labels corresponding to a set of cardiovascular conditions may be typically treated by cardiologists, and a supervised machine-learning process may be performed to relate those prognostic labels to alimentary labels associated with various alimentary options.

With continued reference to FIG. 13, alimentary instruction label learner 552 may perform one or more unsupervised machine-learning processes as described above; unsupervised processes may be performed by an unsupervised learning module 1304 executing on diagnostic engine 108 and/or on another computing device in communication with diagnostic engine 108, which may include any hardware or software module. For instance, and without limitation, alimentary instruction label learner 552 and/or diagnostic engine 108 may perform an unsupervised machine learning process on second training set 520, which may cluster data of second training set 520 according to detected relationships between elements of the second training set 520, including without limitation correlations of prognostic labels to each other and correlations of alimentary labels to each other; such relations may then be combined with supervised machine learning results to add new criteria for alimentary instruction label learner 552 to apply in relating prognostic labels to alimentary labels. As a non-limiting, illustrative example, an unsupervised process may determine that a first prognostic label 508 correlates closely with a second prognostic label 524, where the first prognostic label 508 has been linked via supervised learning processes to a given alimentary label, but the second has not; for instance, the second prognostic label 524 may not have been defined as an input for the supervised learning process, or may pertain to a domain outside of a domain limitation for the supervised learning process. Continuing the example, a close correlation between first prognostic label 508 and second prognostic label 524 may indicate that the second prognostic label 524 is also a good match for the alimentary label; second prognostic label 524 may be included in a new supervised process to derive a relationship or may be used as a synonym or proxy for the first prognostic label 508 by alimentary instruction label learner 552. Unsupervised processes performed by alimentary instruction label learner 552 may be subjected to any domain limitations suitable for unsupervised processes performed by prognostic label learner 536 as described above.

Still referring to FIG. 13, diagnostic engine 108 and/or alimentary instruction label learner 552 may detect further significant categories of prognostic labels, relationships of such categories to alimentary labels, and/or categories of alimentary labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to diagnostic engine 108, alimentary instruction label learner 552 and/or diagnostic engine 108 may continuously or iteratively perform unsupervised machine-learning processes to detect relationships between different elements of the added and/or overall data; in an embodiment, this may enable diagnostic engine 108 to use detected relationships to discover new correlations between known biomarkers, prognostic labels, and/or alimentary labels and one or more elements of data in large bodies of data, such as genomic, proteomic, and/or microbiome-related data, enabling future supervised learning and/or lazy learning processes to identify relationships between, e.g., particular clusters of genetic alleles and particular prognostic labels and/or suitable alimentary labels. Use of unsupervised learning may greatly enhance the accuracy and detail with which system may detect prognostic labels and/or alimentary labels.

Continuing to view FIG. 13, alimentary instruction label learner 552 may be configured to perform a lazy learning process as a function of the second training set 520 and the at least a prognostic output to produce the at least an alimentary output; a lazy learning process may include any lazy learning process as described above regarding prognostic label learner 536. Lazy learning processes may be performed by a lazy learning module 1308 executing on diagnostic engine 108 and/or on another computing device in communication with diagnostic engine 108, which may include any hardware or software module. Alimentary data output 1312 may be provided to a user output device as described in further detail below.

In an embodiment, and still referring to FIG. 13, alimentary instruction label learner 552 may generate a plurality of alimentary labels having different implications for a particular person. For instance, where a prognostic label indicates that a person has a magnesium deficiency, various dietary choices may be generated as alimentary labels associated with correcting the deficiency, such as alimentary labels associated with consumption of almonds, spinach, and/or dark chocolate, as well as alimentary labels associated with consumption of magnesium supplements. In such a situation, alimentary instruction label learner 552 and/or diagnostic engine 108 may perform additional processes to resolve ambiguity. Processes may include presenting multiple possible results to a medical practitioner, informing the medical practitioner of various options that may be available, and/or that follow-up tests, procedures, or counseling may be required to select an appropriate choice. Alternatively or additionally, processes may include additional machine learning steps. For instance, alimentary instruction label learner 552 may perform one or more lazy learning processes using a more comprehensive set of user data to identify a more probably correct result of the multiple results. Results may be presented and/or retained with rankings, for instance to advise a medical professional of the relative probabilities of various alimentary labels being correct or ideal choices for a given person; alternatively or additionally, alimentary labels associated with a probability of success or suitability below a given threshold and/or alimentary labels contradicting results of the additional process, may be eliminated. As a non-limiting example, an additional process may reveal that a person is allergic to tree nuts, and consumption of almonds may be eliminated as an alimentary label to be presented.

Continuing to refer to FIG. 13, alimentary instruction label learner 552 may be designed and configured to generate further training data and/or to generate outputs using longitudinal data 1316. As used herein, longitudinal data 1316 may include a temporally ordered series of data concerning the same person, or the same cohort of persons; for instance, longitudinal data 1316 may describe a series of blood samples taken one day or one month apart over the course of a year. Longitudinal data 1316 may relate to a series of samples tracking response of one or more elements of physiological data recorded regarding a person undergoing one or more alimentary processes linked to one or more alimentary process labels. Alimentary instruction label learner 552 may track one or more elements of physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given alimentary process over time on a physiological parameter. Functions may be compared to each other to rank alimentary processes; for instance, an alimentary process associated with a steeper slope in curve representing improvement in a physiological data element, and/or a shallower slope in a curve representing a slower decline, may be ranked higher than an alimentary process associated with a less steep slope for an improvement curve or a steeper slope for a curve marking a decline. Alimentary processes associated with a curve and/or terminal data point representing a value that does not associate with a previously detected prognostic label may be ranked higher than one that is not so associated. Information obtained by analysis of longitudinal data 1316 may be added to alimentary process database and/or second training set.

Embodiments of diagnostic engine 108 may furnish augmented intelligence systems that facilitate diagnostic, prognostic, curative, and/or therapeutic decisions by nutrition, diet, and wellness professionals such as nutritionists, dieticians, or applicable trainers/coaches/mentors. Diagnostic engine 108 may provide fully automated tools and resources for each applicable professional to handle, process, diagnosis, develop alimentary, diet, or wellness plans, facilitate and monitor all patient implementation, and record each patient status. Provision of expert system elements via expert inputs and document-driven language analysis may ensure that recommendations generated by diagnostic engine 108 are backed by the very best medical and alimentary knowledge and practices in the world. Models and/or learners with access to data in depth may enable generation of recommendations that are directly personalized for each patient, providing complete confidence, mitigated risk, and complete transparency. Access to well-organized and personalized knowledge in depth may greatly enhance efficiency of nutrition consultations; in embodiments, a comprehensive session may be completed in as little as 10 minutes. Recommendations may further suggest follow up testing, therapy, and/or delivery of substances, ensuring an effective ongoing treatment and prognostic plan.

Referring again to FIG. 1, vibrant constitutional network system 100 includes a plan generation module 112 operating on the at least a server 104. Plan generation module 112 may include any suitable hardware or hardware module. In an embodiment, plan generation module 112 is designed and configured to generate a comprehensive instruction set 206 associated with the user based on the diagnostic output. In an embodiment, comprehensive instruction set 206 is a data structure containing instructions to be provided to the user to explain the user's current prognostic status, as reflected by one or more prognostic outputs and provide the user with a plan based on the at least an alimentary instruction set output, to achieve that. Comprehensive instruction set 206 may include but is not limited to a program, strategy, summary, recommendation, or any other type of interactive platform that may be configured to comprise information associated with the user, an applicable verified external source, and one or more outputs derived from the analyses performed on the extraction from the user. Comprehensive instruction set 206 may describe to a user a future prognostic status to aspire to.

Figure 14:
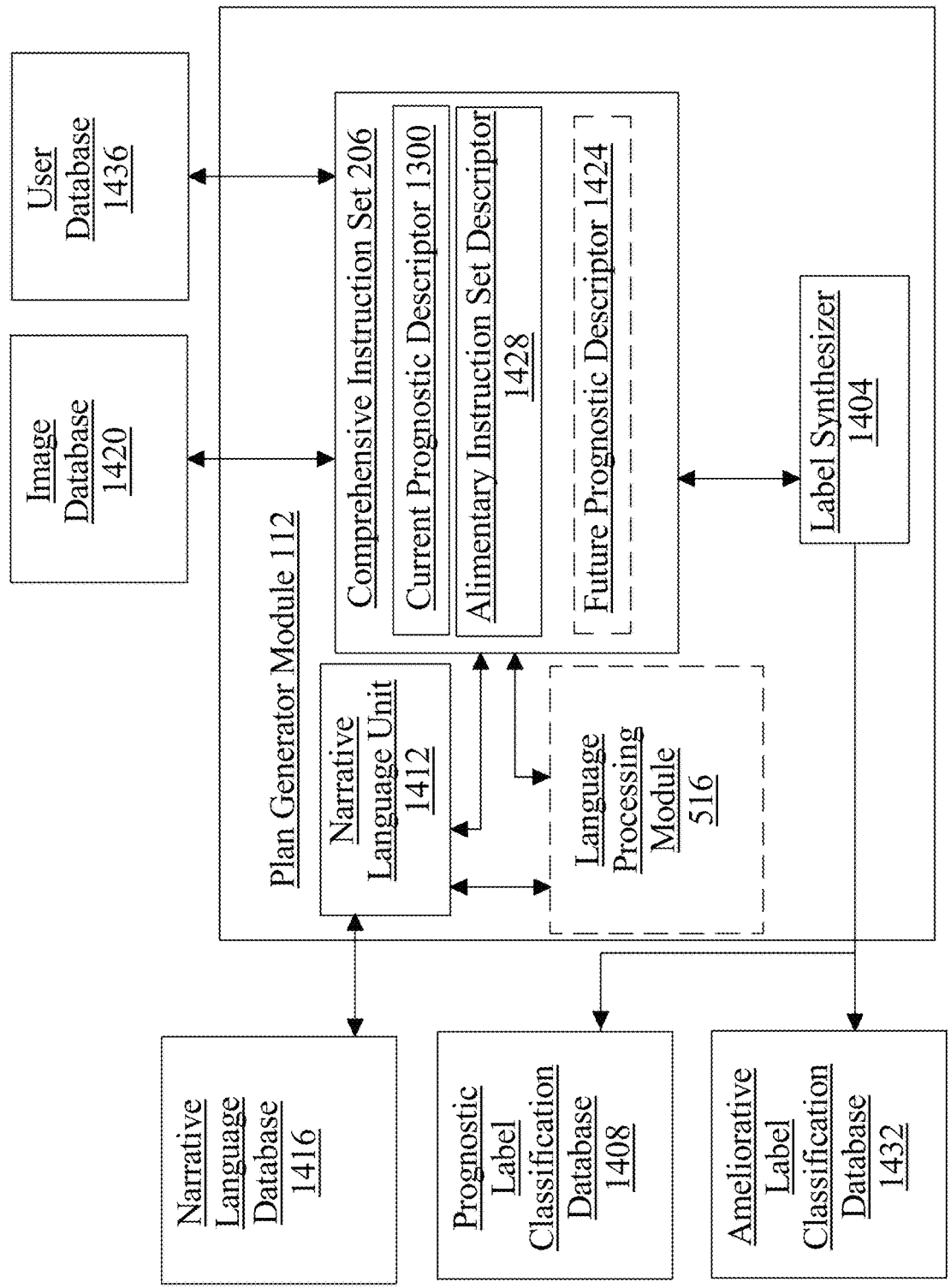
FIG. 14 is a block diagram illustrating an exemplary embodiment of a plan generator module and associated system elements.

Referring now to FIG. 14, an exemplary embodiment of a plan generation module 112 is illustrated. Comprehensive instruction set 206 includes at least a current prognostic descriptor 1400 which as used in this disclosure is an element of data describing a current prognostic status based on at least one prognostic output. Plan generation module 112 may produce at least a current prognostic descriptor 1400 using at least a prognostic output. In an embodiment, plan generation module 112 may include a label synthesizer 1404. Label synthesizer 1404 may include any suitable software or hardware module. In an embodiment, label synthesizer 1404 may be designed and configured to combine a plurality of labels in at least a prognostic output together to provide maximally efficient data presentation. Combination of labels together may include elimination of duplicate information. For instance, label synthesizer 1404 and/or at least a server 104 may be designed and configure to determine a first prognostic label of the at least a prognostic label is a duplicate of a second prognostic label of the at least a prognostic label and eliminate the first prognostic label. Determination that a first prognostic label is a duplicate of a second prognostic label may include determining that the first prognostic label is identical to the second prognostic label; for instance, a prognostic label generated from test data presented in one biological extraction of at least a biological extraction may be the same as a prognostic label generated from test data presented in a second biological extraction of at least a biological extraction. As a further non-limiting example, a first prognostic label may be synonymous with a second prognostic label, where detection of synonymous labels may be performed, without limitation, by a language processing module 516 as described above.

Continuing to refer to FIG. 13, label synthesizer 1404 may group prognostic labels according to one or more classification systems relating the prognostic labels to each other. For instance, plan generation module 112 and/or label synthesizer 1404 may be configured to determine that a first prognostic label of the at least a prognostic label and a second prognostic label of the at least a prognostic label belong to a shared category. A shared category may be a category of conditions or tendencies toward a future condition to which each of first prognostic label and second prognostic label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with prognostic labels as well. A given prognostic label may belong to a plurality of overlapping categories. Plan generation module 112 may be configured to add a category label associated with a shared category to comprehensive instruction set 206, where addition of the label may include addition of the label and/or a datum linked to the label, such as a textual or narrative description. In an embodiment, relationships between prognostic labels and categories may be retrieved from a prognostic label classification database 1408, for instance by generating a query using one or more prognostic labels of at least a prognostic output, entering the query, and receiving one or more categories matching the query from the prognostic label classification database 1408.

Figure 15:
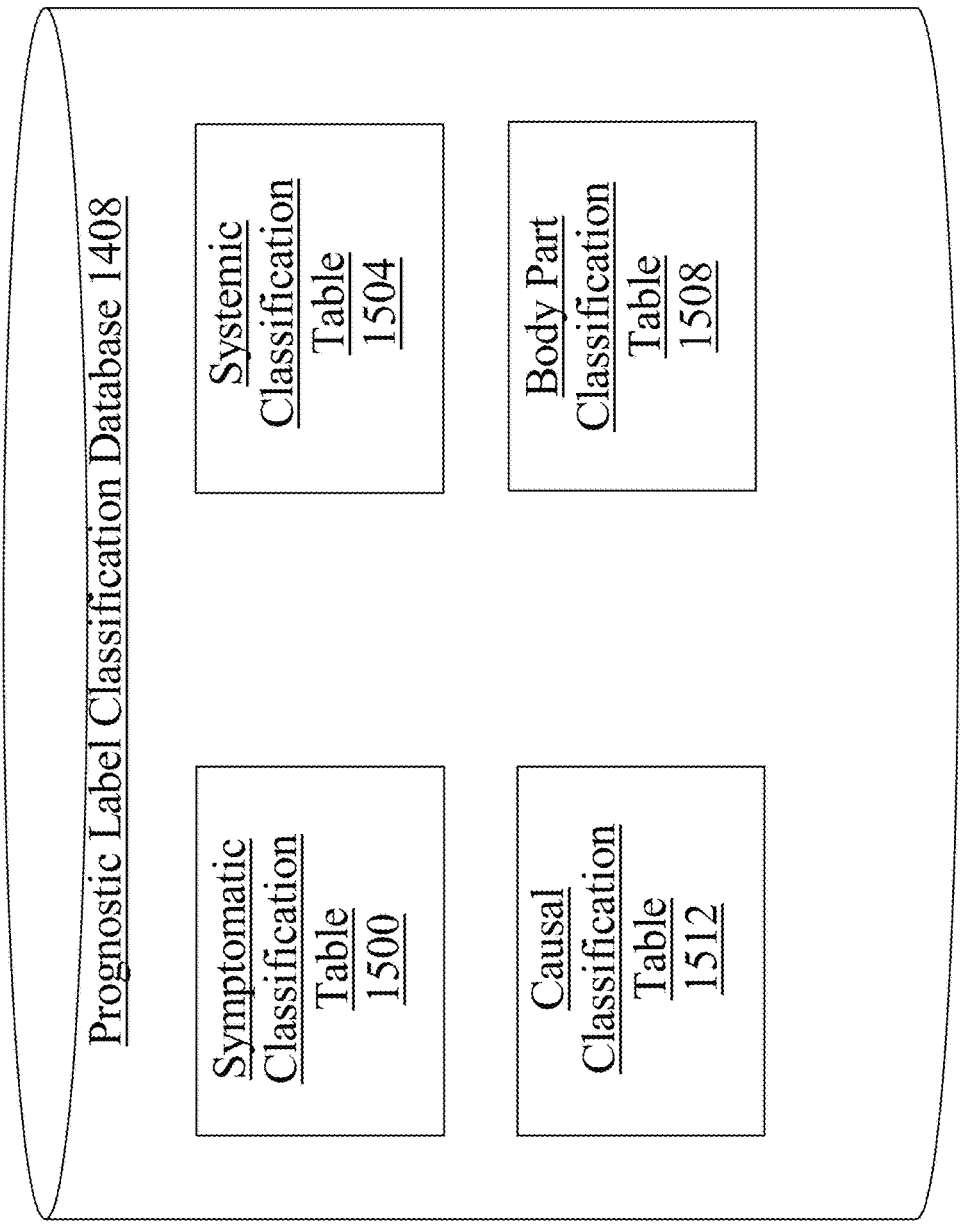
FIG. 15 is a block diagram illustrating an exemplary embodiment of a prognostic label classification database.

Referring now to FIG. 15, an exemplary embodiment of a prognostic label classification database 1408 is illustrated. Prognostic label classification database 1408 may be implemented as any database and/or datastore suitable for use as biological extraction database 600 as described above. One or more database tables in prognostic label classification database 1408 may include, without limitation, a symptomatic classification table 1500; symptomatic classification table 1500 may relate each prognostic label to one or more categories of symptoms associated with that prognostic label. As a non-limiting example, symptomatic classification table 1500 may include records indicating that each of lactose intolerance and gluten sensitivity results in symptoms including gas buildup, bloating, and abdominal pain. One or more database tables in prognostic label classification database 1408 may include, without limitation, a systemic classification table 1204; systemic classification table 1504 may relate each prognostic label to one or more systems associated with that prognostic label. As a non-limiting example, systemic classification table 1504 may include records indicating each of lactose intolerance and gluten sensitivity affects the digestive system; two digestive sensitivities linked to allergic or other immune responses may additionally be linked in systemic classification table 1504 to the immune system. One or more database tables in prognostic label classification database 1408 may include, without limitation, a body part classification table 1508; body part classification table 1508 may relate each prognostic label to one or more body parts associated with that prognostic label. As a non-limiting example, body part classification table 1508 may include records indicating each of psoriasis and rosacea affects the skin of a person. One or more database tables in prognostic label classification database 1408 may include, without limitation, a causal classification table 1512; causal classification table 1512 may relate each prognostic label to one or more causes associated with that prognostic label. As a non-limiting example, causal classification table 1512 may include records indicating each of type 2 diabetes and hypertension may have obesity as a cause. The above-described tables, and entries therein, are provided solely for exemplary purposes. Persons skilled in the art, upon reviewing the entirety of this disclosure, will be aware of various additional examples for tables and/or relationships that may be included or recorded in prognostic classification table consistently with this disclosure.

Referring again to FIG. 14, plan generation module 112 may be configured to generate current prognostic descriptor 1400 by converting one or more prognostic labels into narrative language. As a non-limiting example, plan generation module 112 may include a narrative language unit 1412, which may be configured to determine an element of narrative language associated with at least a prognostic label and include the element of narrative language in current prognostic label descriptor. Narrative language unit 1412 may implement this, without limitation, by using a language processing module 516 to detect one or more associations between prognostic labels, or lists of prognostic labels, and phrases and/or statements of narrative language. Alternatively or additionally, Narrative language unit 1412 may retrieve one or more elements of narrative language from a narrative language database 1416, which may contain one or more tables associating prognostic labels and/or groups of prognostic labels with words, sentences, and/or phrases of narrative language. One or more elements of narrative language may be included in comprehensive instruction set 206, for instance for display to a user as text describing a current prognostic status of the user. Current prognostic descriptor 1400 may further include one or more images; one or more images may be retrieved by plan generation module 112 from an image database 1420, which may contain one or more tables associating prognostic labels, groups of prognostic labels, current prognostic descriptors 1400, or the like with one or more images.

With continued reference to FIG. 14, comprehensive instruction set 206 may include one or more follow-up suggestions, which may include, without limitation, suggestions for acquisition of an additional biological extraction; in an embodiment, additional biological extraction may be provided to diagnostic engine 108, which may trigger repetition of one or more processes as described above, including without limitation generation of prognostic output, refinement or elimination of ambiguous prognostic labels of prognostic output, generation of alimentary instruction set output, and/or refinement or elimination of ambiguous alimentary instruction set labels of alimentary instruction set output. For instance, where a pegboard test result suggests possible diagnoses of Parkinson's disease, Huntington's disease, ALS, and MS as described above, follow-up suggestions may include suggestions to perform endocrinal tests, genetic tests, and/or electromyographic tests; results of such tests may eliminate one or more of the possible diagnoses, such that a subsequently displayed output only lists conditions that have not been eliminated by the follow-up test. Follow-up tests may include any receipt of any biological extraction as described above.

With continued reference to FIG. 14, comprehensive instruction set may include one or more elements of contextual information, including without limitation any patient history such as current lab results, a current reason for visiting a professional, current status of one or more currently implemented treatment plans, biographical information concerning the patient, and the like. One or more elements of contextual information may include goals a patient wishes to achieve with a medical visit or session, and/or as result of interaction with diagnostic engine 108. Contextual information may include one or more questions a patient wishes to have answered in a visit and/or session, and/or as a result of interaction with diagnostic engine 108. Contextual information may include one or more questions to ask a patient. Persons skilled in the art, upon reviewing the entirety of this disclosure, will be aware of various forms of contextual information that may be included, consistently with this disclosure.

With continued reference to FIG. 14, comprehensive instruction set 206 may include at least a future prognostic descriptor 1424. As used herein, a future prognostic descriptor 1424 is an element of data describing a future prognostic status based on at least one prognostic output, which may include without limitation a desired further prognostic status. In an embodiment, future prognostic descriptor 1424 may include any element suitable for inclusion in current prognostic descriptor 1400. Future prognostic descriptor 1424 may be generated using any processes, modules, and/or components suitable for generation of current prognostic descriptor 1400 as described above.

Still referring to FIG. 14, comprehensive instruction set 206 includes at least an alimentary plan descriptor 1428, which as defined in this disclosure an element of data describing one or more alimentary instruction set processes to be followed based on at least one alimentary instruction set output; at least an alimentary instruction set process descriptor 1428 may include descriptors for alimentary instruction set processes usable to achieve future prognostic descriptor 1424. Plan generation module 112 may receive at least an alimentary plan descriptor 1428 from alimentary instruction set generator module 120.

Continuing to refer to FIG. 14, plan generation module 112 may be configured to receive at least an element of user data and filter diagnostic output using the at least an element of user data. At least an element of user data, as used herein, is any element of data describing the user, user needs, and/or user preferences. At least an element of user data may include a constitutional restriction. At least a constitutional restriction may include any constitutional reason that a user may be unable to engage in a given alimentary instruction set process; at least a constitutional restriction may include any counter-indication as described above, including an injury, a diagnosis of something preventing use of one or more alimentary instruction set processes, an allergy or food-sensitivity issue, a medication that is counter-indicated, or the like. At least an element of user data may include at least a user preference. At least a user preference may include, without limitation, any preference to engage in or eschew any alimentary instruction set process and/or other potential elements of a comprehensive instruction set 206, including religious preferences such as forbidden foods, medical interventions, exercise routines, or the like.

Still referring to FIG. 14, comprehensive instruction set 206 includes at least an ameliorative process descriptor, which as defined in this disclosure an element of data describing one or more ameliorative processes to be followed based on at least one ameliorative output; at least an ameliorative process descriptor may include descriptors for ameliorative processes usable to achieve future prognostic descriptor 1424. Plan generation module 112 may produce at least an ameliorative process descriptor using at least a prognostic output. In an embodiment, label synthesizer 1404 may be designed and configured to combine a plurality of labels in at least an ameliorative output together to provide maximally efficient data presentation. Combination of labels together may include elimination of duplicate information. For instance, label synthesizer 1404 and/or at least a server 104 may be designed and configure to determine a first ameliorative label of the at least an ameliorative label is a duplicate of a second ameliorative label of the at least an ameliorative label and eliminate the first ameliorative label. Determination that a first ameliorative label is a duplicate of a second ameliorative label may include determining that the first ameliorative label is identical to the second ameliorative label; for instance, a ameliorative label generated from test data presented in one biological extraction of at least a biological extraction may be the same as a ameliorative label generated from test data presented in a second biological extraction of at least a biological extraction. As a further non-limiting example, a first ameliorative label may be synonymous with a second ameliorative label, where detection of synonymous labels may be performed, without limitation, by a language processing module 516 as described above.

Continuing to refer to FIG. 11, label synthesizer 1404 may group ameliorative labels according to one or more classification systems relating the ameliorative labels to each other. For instance, plan generation module 112 and/or label synthesizer 1404 may be configured to determine that a first ameliorative label of the at least an ameliorative label and a second ameliorative label of the at least an ameliorative label belong to a shared category. A shared category may be a category of conditions or tendencies toward a future condition to which each of first ameliorative label and second ameliorative label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with ameliorative labels as well. A given ameliorative label may belong to a plurality of overlapping categories. Plan generation module 112 may be configured to add a category label associated with a shared category to comprehensive instruction set 206, where addition of the label may include addition of the label and/or a datum linked to the label, such as a textual or narrative description. In an embodiment, relationships between ameliorative labels and categories may be retrieved from an ameliorative label classification database 1432, for instance by generating a query using one or more ameliorative labels of at least an ameliorative output, entering the query, and receiving one or more categories matching the query from the ameliorative label classification database 1432.

Figure 16:
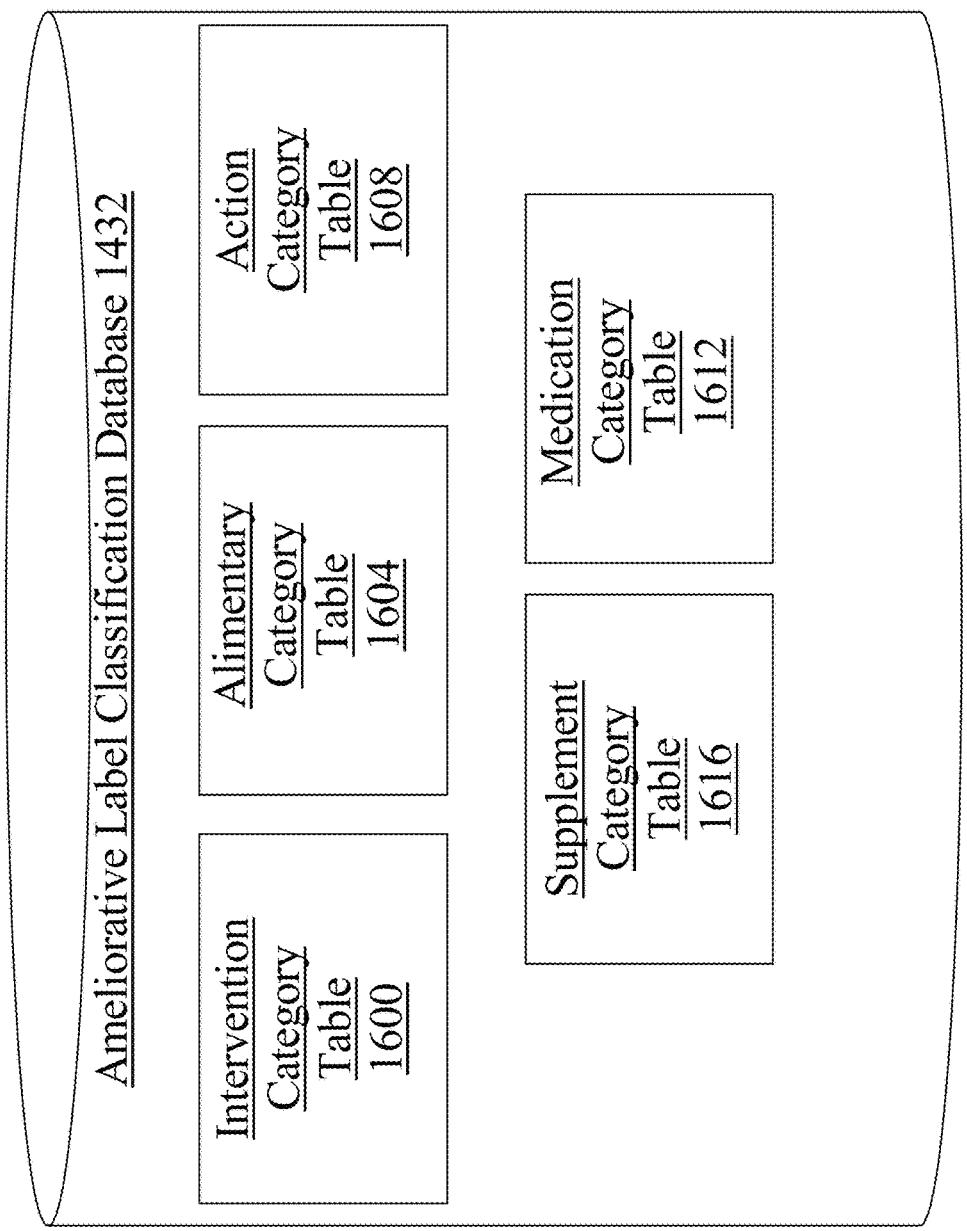
FIG. 16 is a block diagram illustrating an exemplary embodiment of an ameliorative label classification database.

Referring now to FIG. 16, an exemplary embodiment of an ameliorative label classification database 1432 is illustrated. Ameliorative label classification database 1432 may be implemented as any database and/or datastore suitable for use as biological extraction database 600 as described above. One or more database tables in ameliorative label classification database 1432 may include, without limitation, an intervention category table 1600; an intervention may relate each ameliorative label to one or more categories associated with that ameliorative label. As a non-limiting example, intervention category table 1600 may include records indicating that each of a plan to consume a given quantity of almonds and a plan to consume less meat maps to a category of nutritional instruction, while a plan to jog for 30 minutes per day maps to a category of activity. One or more database tables in ameliorative label classification database 1432 may include, without limitation, an alimentary category table 1604; alimentary category table 1604 may relate each ameliorative label pertaining to nutrition to one or more categories associated with that ameliorative label. As a non-limiting example, alimentary category table 1604 may include records indicating that each of a plan to consume more almonds and a plan to consume more walnuts qualifies as a plan to consume more nuts, as well as a plan to consume more protein. One or more database tables in ameliorative label classification database 1432 may include, without limitation, an action category table 1208; action category table 1608 may relate each ameliorative label pertaining to an action to one or more categories associated with that ameliorative label. As a non-limiting example, action category table 1608 may include records indicating that each of a plan jog for 30 minutes a day and a plan to perform a certain number of sit-ups per day qualifies as an exercise plan. One or more database tables in ameliorative label classification database 1432 may include, without limitation, a medication category table 1612; medication category table 1612 may relate each ameliorative label associated with a medication to one or more categories associated with that ameliorative label. As a non-limiting example, medication category table 1612 may include records indicating that each of a plan to take an antihistamine and a plan to take an anti-inflammatory steroid belongs to a category of allergy medications. One or more database tables in ameliorative label classification database 1432 may include, without limitation, a supplement category table 1616; supplement category table 1616 may relate each ameliorative label pertaining to a supplement to one or more categories associated with that ameliorative label. As a non-limiting example, supplement category table 1616 may include records indicating that each of a plan to consume a calcium supplement and a plan to consume a vitamin D supplement corresponds to a category of supplements to aid in bone density. Ameliorative labels may be mapped to each of alimentary category table 1604, action category table 1508, supplement category table 1616, and medication category table 1612 using intervention category table 1600. The above-described tables, and entries therein, are provided solely for exemplary purposes. Persons skilled in the art, upon reviewing the entirety of this disclosure, will be aware of various additional examples for tables and/or relationships that may be included or recorded in ameliorative classification table consistently with this disclosure.

Referring again to FIG. 1, system 100 includes an alimentary instruction set generator module 120 operating on at least a server 104. Alimentary instruction set generator module 120 may include any hardware or software module suitable for use as a plan generator module 112. Alimentary instruction set generator module may interact with plan generator module 112. For instance, and without limitation, alimentary instruction set generator module 120 may be configured to generate, based on comprehensive instruction set 206, an alimentary instruction set 208 associated with the user.

In one embodiment, comprehensive instruction set 206 includes at least one or more elements of contextual information, including without limitation any patient medical history such as current lab results, a current reason for visiting a medical professional, current status of one or more currently implemented treatment plans, biographical information concerning the patient, and the like. One or more elements of contextual information may include goals a patient wishes to achieve with a medical visit or session, and/or as result of interaction with diagnostic engine 108. Contextual information may include one or more questions a patient wishes to have answered in a medical visit and/or session, and/or as a result of interaction with diagnostic engine 108. Contextual information may include one or more questions to ask a patient. Persons skilled in the art, upon reviewing the entirety of this disclosure, will be aware of various forms of contextual information that may be included, consistently with this disclosure.

Figure 17:
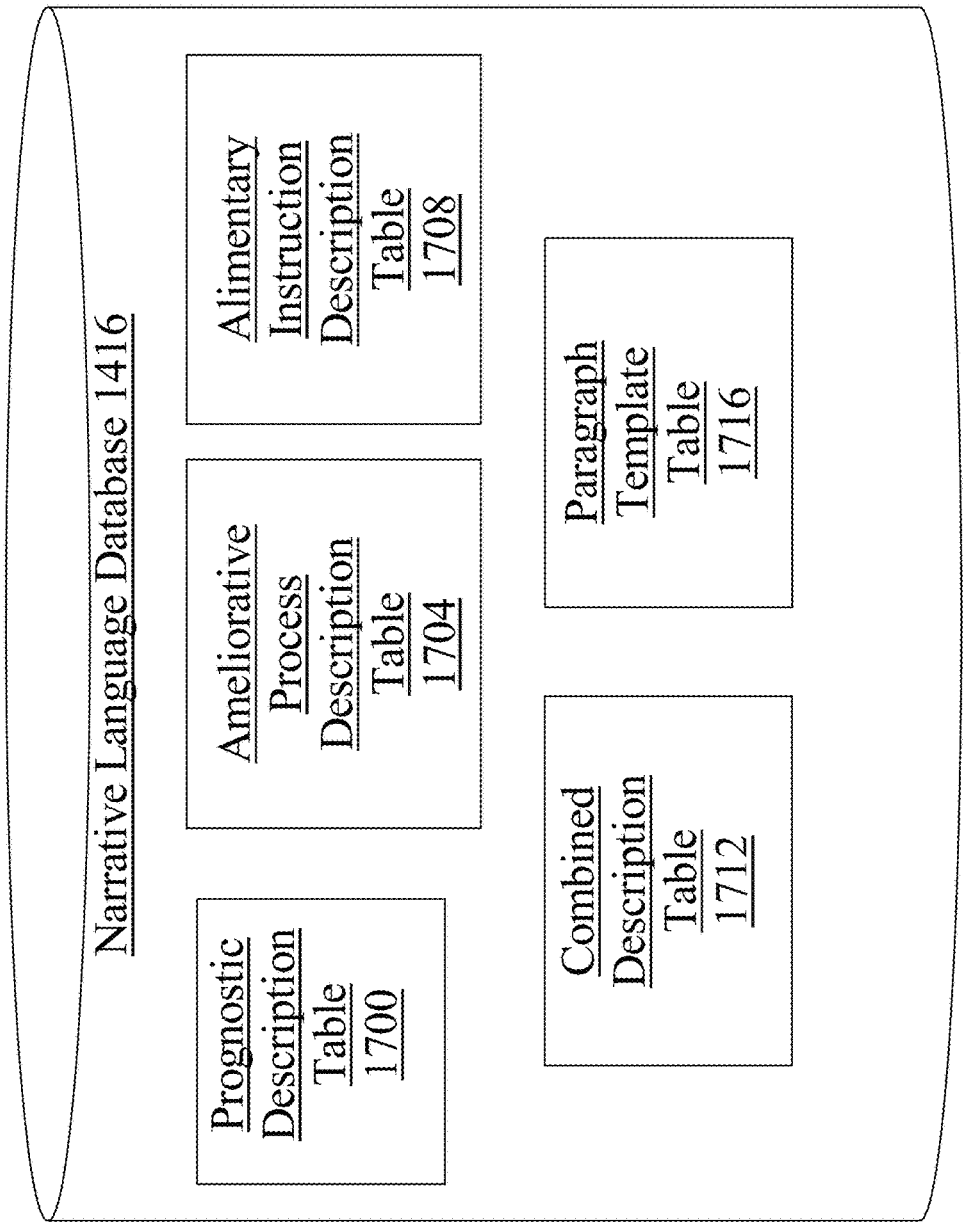
FIG. 17 is a block diagram illustrating an exemplary embodiment of a narrative language database.

Referring now to FIG. 17, an exemplary embodiment of a narrative language database 1416 is illustrated. Narrative language database 1416 may be implemented as any database and/or datastore suitable for use as biological extraction database 600 as described above. One or more database tables in narrative language database 1416 may include, without limitation, a prognostic description table 1700, which may link prognostic labels to narrative descriptions associated with prognostic labels. One or more database tables in narrative language database 1416 may include, without limitation, an alimentary instruction set description table 1708, which may link alimentary instruction set process labels to narrative descriptions associated with alimentary instruction set process labels. One or more database tables in narrative language database 1416 may include, without limitation, a combined description table 1712, which may link combinations of prognostic labels and alimentary instruction set labels to narrative descriptions associated with the combinations. One or more database tables in narrative language database 1416 may include, without limitation, a paragraph template table 1716, which may contain one or more templates of paragraphs, pages, reports, or the like into which images and text, such as images obtained from Image database 1420 and text obtained from prognostic description table 1300, alimentary instruction set description table 1708, and combined description table 1712 may be inserted. Tables in narrative language database 1416 may be populated, as a non-limiting example, using submissions from experts, which may be collected according to any processes described above. Persons skilled in the art, upon reviewing the entirety of this disclosure, will be aware of various way sin which entries in narrative language database 1416 may be categorized and/or organized.

Figure 18:
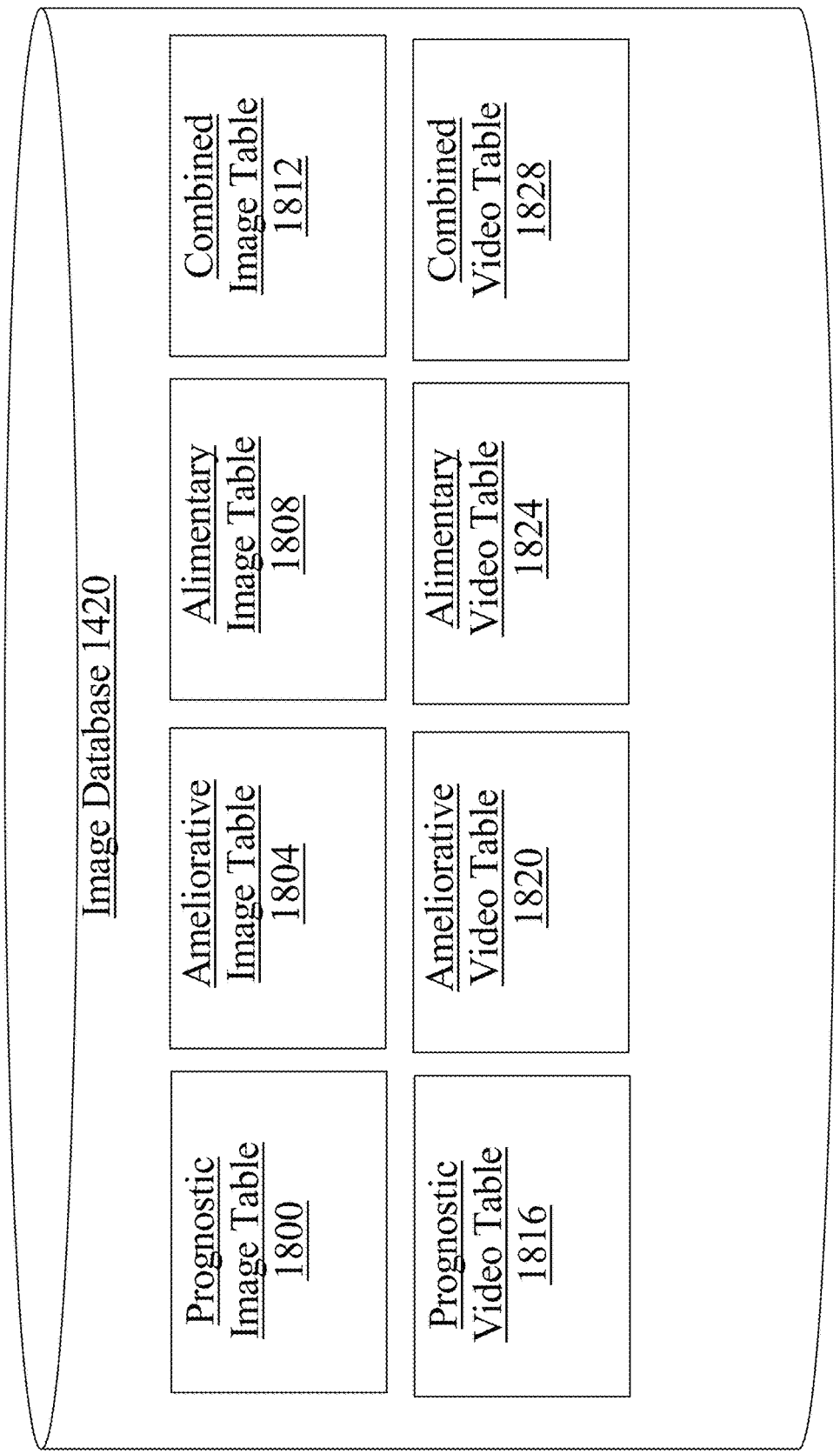
FIG. 18 is a block diagram illustrating an exemplary embodiment of an image database.

Referring now to FIG. 18, an exemplary embodiment of an Image database 1420 is illustrated. Image database 1420 may be implemented as any database and/or datastore suitable for use as biological extraction database 600 as described above. One or more database tables in image database 1420 may include, without limitation, a prognostic image table 1800, which may link prognostic labels to images associated with prognostic labels. One or more database tables in Image database 1420 may include, without limitation, an ameliorative image table 1804, which may link alimentary instruction set process labels to images associated with alimentary instruction set process labels. One or more database tables in Image database 1420 may include, without limitation, a combined image table 1812, which may link combinations of prognostic labels and alimentary instruction set labels to images associated with the combinations. One or more database tables in image database 1420 may include, without limitation, a prognostic video table 1816, which may link prognostic labels to videos associated with prognostic labels. One or more database tables in Image database 1420 may include, without limitation, an alimentary instruction set video table 1824, which may link alimentary instruction set process labels to videos associated with alimentary instruction set process labels. One or more database tables in Image database 1420 may include, without limitation, a combined video table 1812, which may link combinations of prognostic labels and alimentary instruction set labels to videos associated with the combinations. Tables in Image database 1420 may be populated, without limitation, by submissions by experts, which may be provided according to any process or process steps described in this disclosure for collection of expert submissions.

Figure 19:
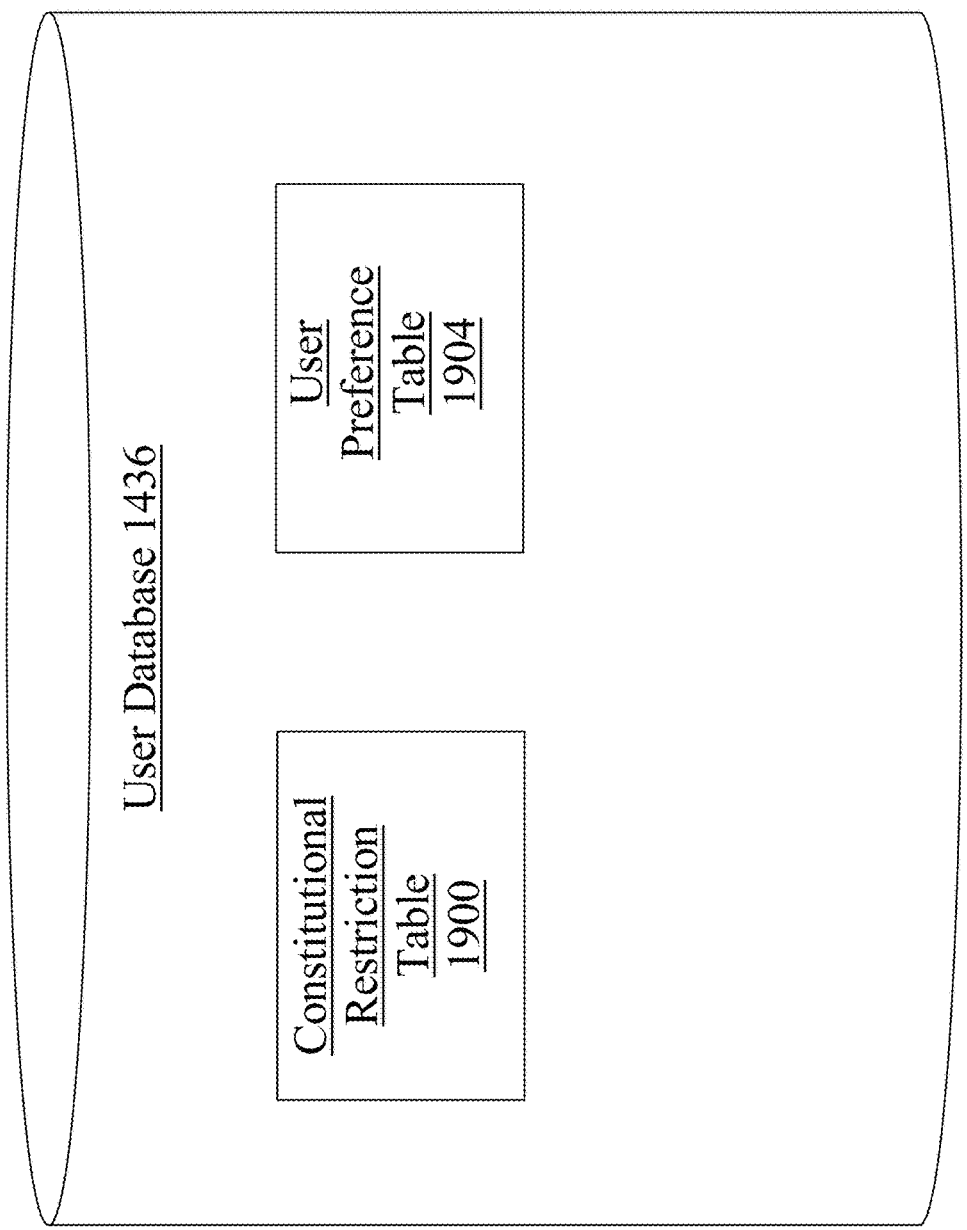
FIG. 19 is a block diagram illustrating an exemplary embodiment of user database.

Referring to FIG. 19, an exemplary embodiment of a user database 1436 is illustrated. User database 1436 may be implemented as any database and/or datastore suitable for use as biological extraction database 600 as described above. One or more database tables in user database 1436 may include, without limitation, a constitution restriction table 1900; at least a constitutional restriction may be linked to a given user and/or user identifier in a constitutional restriction table 1800. One or more database tables in user database 1436 may include, without limitation, a user preference table 1904; at least a user preference may be linked to a given user and/or user identifier in a user preference table 1904.

Referring again to FIG. 1, system 100 includes an alimentary instruction set generator module 120 operating on at least a server 104. Alimentary instruction set generator module 120 may include any hardware or software module suitable for use as a plan generator module 112. Alimentary instruction set generator module may interact with plan generator module 112. For instance, and without limitation, alimentary instruction set generator module 120 may be configured to generate, based on comprehensive instruction set 206, an alimentary instruction set 208 associated with the user.

Figure 20:
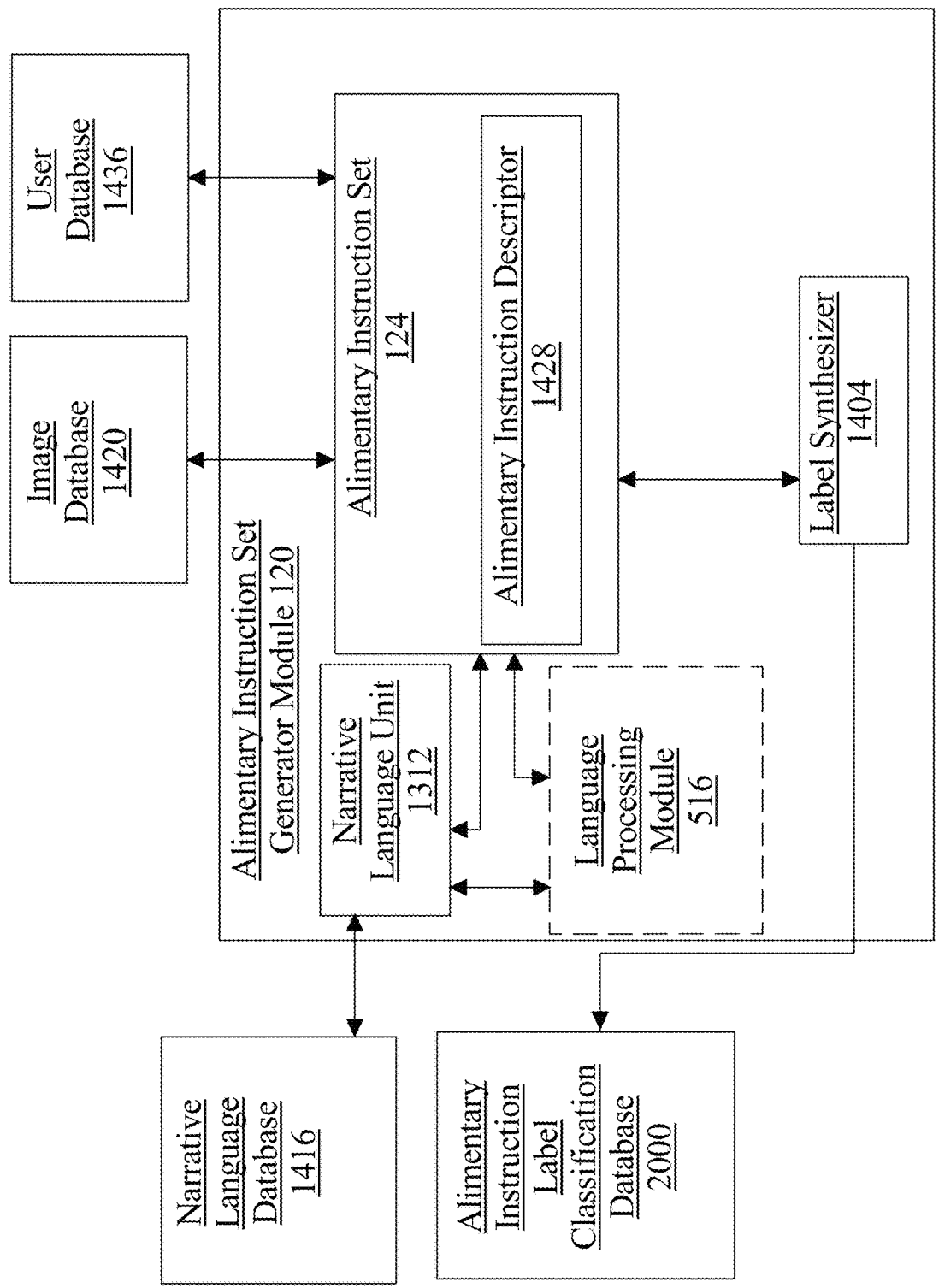
FIG. 20 is a block diagram illustrating an exemplary embodiment of an alimentary instruction set generator module.

Referring now to FIG. 20, an exemplary embodiment of an alimentary instruction set generation module 120 is illustrated. In one embodiment, the alimentary instruction set generation module 120 may be configured to generate an alimentary instruction set comprising a plurality of information reflecting a comprehensive list of meals, supplements, and processes aimed towards resolving any identified issues, suggestions, or deficiencies discoverable via the comprehensive instruction set 206. Alimentary instruction set generation module 120 may be configured to generate an alimentary instruction set associated with user 202 that automatically interacts with a plurality of performances and processes (as illustrated in FIG. 2 via Performances 210-216) and generates a set of orders or instructions configured to be processed by Performances 210-216. Alimentary instruction set generation module 120 may produce at least an alimentary instruction set process descriptor 1428 using at least an alimentary instruction set output. In an embodiment, Alimentary instruction set generation module may include a label synthesizer 1404 as described above.

In one embodiment, and still referring to FIG. 20, the alimentary instruction set may be presented to user 202 via a graphical user interface coupled to user client device 132 associated with user 202 operating in or subscribing to network 200. Alimentary instruction set 208 is further configured to export data to external destinations based on the categorization of components of alimentary instruction set 208 within performances 210-216. Alimentary instruction set 208 is configured to interact with one or more servers associated with performances 210-216 by vibrant constitutional network 200 establishing a communicatively coupling relationship between the alimentary instruction set and respective physical performance entity servers 306 configured to execute the physical performance instruction set associated with respective performances 210-216. Performances 210-216 may be but are not limited to any food preparation performances, food delivery performances, vitamin/supplement coaching service, constitutional supplement delivery service, grocery delivery service, or any other applicable platform configured for preparation and delivery of items relating to food/nutrition, constitutional benefit, or the like.

Continuing to refer to FIG. 20, alimentary instruction set generator module 120 is designed and configured to an alimentary instruction set 208 based on comprehensive instruction set 206. In an embodiment, alimentary instruction set generator module 120 may generate alimentary instruction set 208 based on the integration of data associated with comprehensive instruction set 206, any applicable external sources, and any applicable database within system 100 or physical performance entity network 302. Generation of alimentary instruction set 208 may include identification of one or more alimentary instructions in comprehensive instruction set, and insertion of the one or more alimentary instructions in the alimentary instruction set 208; for instance, alimentary instruction set 208 may be formed, wholly or partially, by aggregating alimentary instructions from comprehensive instruction set 206 and combining the aggregated alimentary instructions using narrative language module, narrative language database, image database, or the like, according to any process suitable for generation of comprehensive instruction set as described above.

In one embodiment, and with continued reference to FIG. 20, alimentary instruction set generator module 120 may generate alimentary instruction set 208 based on alimentary data and non-alimentary data in order to facilitate both medicinal and holistic components in alimentary instruction set 208 specific to user 202. In one embodiment, alimentary data may be identified and aggregated into a subset of applicable alimentary data based on at least a biological extraction 204 and comprehensive instruction set 206. In application, alimentary instruction set 208 may comprise a plurality of alimentary data specific to user 202 that is able to be used by machine learning and artificial intelligence systems in order to continuously update or modify training sets, and ultimately comprehensive instruction set 206 and alimentary instruction set 208 based on updated or progressions associated with implementation of alimentary instruction set 208 by user 202. Alimentary data and non-alimentary data may include compilations of instruction sets received over a period of time, the compilations may account for improvements or modifications associated with user 202. Alimentary instruction set 208 may further include instructions over time, in which the alimentary instructions may change in response to changes in a user's data and/or prognosis. Alternatively or additionally, system 100 may periodically iterate through one or more processes as described in this disclosure, such that repeated reevaluations may modify alimentary instruction set 208 as information concerning user and/or biological extractions obtained from the user change over time.

In one embodiment, and still referring to FIG. 20, alimentary instruction set generation module 120 may identify a non-alimentary instruction within comprehensive instruction set 206, determine an alimentary analog to the non-alimentary instruction and introduce the alimentary analog into the alimentary instruction set and/or use the alimentary analog to update the physical performance instruction set. An alimentary analog, as used herein, is an alimentary process or instruction that achieves a similar purpose to a non-alimentary process and/or instruction. As a non-limiting example, certain foods such as grapefruit may act to lower blood sugar; where the impact of consuming a particular quantity of such foods is similar to or the same as an impact of consuming a blood sugar medication, the former may be an alimentary analog of the latter. In one embodiment, non-alimentary data within comprehensive instruction set 206 may be subsequently substituted in alimentary instruction set 208 with alimentary data configured to provide user 202 with holistic solutions to issues that were initially treated with non-holistic approaches. For example, if initially diagnostic output indicates that the blood sugar of user 202 is abnormally high then comprehensive instruction set 206 may recommend that user 202 take applicable medications classified as non-alimentary in order to lower the blood sugar immediately. The process of user 202 receiving the applicable medications may be based on execution of one of performances 210-216 by physical performance entity 304. However, alimentary instruction set 208 may subsequently or concurrently provide one or more sets of instructions to remedy the improved blood sugar of user 202 via an alimentary solution such as increased consumption of grapefruits, configured to be executed by a physical performance instruction set based on an updated comprehensive instruction set 206 and/or by following alimentary instruction set 208 in lieu of that portion of comprehensive instruction set 206. As a further example, a supplement initially presented in comprehensive instruction set 206 may be subsequently replaced, in alimentary instruction set 208, by a specific food categorized as alimentary in order to remedy the issues in which the initial supplement sought to address. In another example, alimentary data and alimentary solutions may be incorporated into alimentary instruction set 208 upon one or more determinations that the alimentary data and implementations of the alimentary solution are more efficient than non-alimentary solutions initially included in alimentary instruction set 208. Alimentary data and alimentary solutions may also be substituted for less efficient alimentary solutions. For example, if user 202, based on comprehensive instruction set 206, is deemed to need a boost in HDL, then a secondary alimentary solution of eating certain foods may be determined more efficient than a primary alimentary solution of increasing cardio activity.

Still referring to FIG. 20, alimentary instruction set generation module 120 may generate alimentary instruction set 208, at least in part, by identifying at least a negative effect associated with an ameliorative instruction of comprehensive instruction set 206; at least a negative effect may include a "side-effect" of an ameliorative process, such as a side effect of a medication, an increase risk of a type of injury associated with an exercise program, or the like. Alimentary instruction set generation module 120 may determine an alimentary instruction that alleviates the at least a negative effect; for instance, a side-effect of a medication may be alleviated and/or prevented by consumption of an alimentary element tending to alleviate the side-effect. As a non-limiting example, a medication that may cause fluid retention and edema may be provided in comprehensive instruction set 206; alimentary instruction set generation module 120 may determine that consumption of an alimentary element having a diuretic effect, such as a food or drink containing caffeine, may act to prevent or alleviate fluid retention. As a further non-limiting example, comprehensive instruction set 206 may include an instruction for a user to increase his or her exercise regimen, or to begin a new regimen of regular exercise; a counterindication and/or other element of data may indicate an elevated risk of joint injury and/or inflammation as a result of the increased exercise, which may be alleviated or prevented by a lower-calorie diet, consumption of foods containing glucosamine or some other ingredient associated with a reduced risk of joint pain.

Continuing to refer to FIG. 20, alimentary instruction set generation module 120 may determine an alimentary instruction that alleviates the at least a negative effect using machine-learning processes and/or modules as described above; for instance, and without limitation, alimentary instruction set generation module 120 may provide at least a negative effect to ameliorative process label learner and/or alimentary instruction set label leaner in the form of at least a prognostic label; ameliorative process label learner and/or alimentary instruction set label leaner may generate one or more ameliorative labels associated with an alimentary process for alleviating the at least a negative effect.

Continuing to refer to FIG. 20, label synthesizer 1404 may group alimentary labels according to one or more classification systems relating the alimentary labels to each other. For instance, plan generation module 112 and/or label synthesizer 1404 may be configured to determine that a first alimentary label of the at least an alimentary label and a second alimentary label of the at least an alimentary label belong to a shared category. A shared category may be a category of alimentary elements to which each of first alimentary label and second alimentary label belongs; for instance, a first alimentary label associated with tofu and a second alimentary label associated with nuts may each be grouped as a protein source. A given ameliorative label may belong to a plurality of overlapping categories. Plan generation module 112 may be configured to add a category label associated with a shared category to alimentary instruction set 208, where addition of the label may include addition of the label and/or a datum linked to the label, such as a textual or narrative description.

With continued reference to FIG. 20, label synthesizer 1404 may be designed and configured to combine a plurality of labels in at least the alimentary instruction set output together to provide maximally efficient data presentation. Combination of labels together may include elimination of duplicate information. For instance, label synthesizer 1404 and/or at least a server 104 may be designed and configure to determine a first alimentary instruction set label of the at least an alimentary instruction set label is a duplicate of a second alimentary instruction set label of the at least a alimentary instruction set label and eliminate the first alimentary instruction set label. Determination that a first alimentary instruction set label is a duplicate of a second alimentary instruction set label may include determining that the first alimentary instruction set label is identical to the second alimentary instruction set label; for instance, a alimentary instruction set label generated from test data presented in one biological extraction of at least a biological extraction may be the same as a alimentary instruction set label generated from test data presented in a second biological extraction of at least a biological extraction. As a further non-limiting example, a first alimentary instruction set label may be synonymous with a second alimentary instruction set label, where detection of synonymous labels may be performed, without limitation, by a language processing module 516 as described above.

In one embodiment, and still referring to FIG. 20, label synthesizer 1404 may group alimentary instruction set labels according to one or more classification systems relating the alimentary instruction set labels to each other. For instance, plan generation module 112 and/or label synthesizer 1404 may be configured to determine that a first alimentary instruction set label of the at least an alimentary instruction set label and a second alimentary instruction set label of the at least a alimentary instruction set label belong to a shared category. A shared category may be a category of conditions or tendencies toward a future condition to which each of first alimentary instruction set label and second alimentary instruction set label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with alimentary instruction set labels as well. A given alimentary instruction set label may belong to a plurality of overlapping categories. Plan generation module 112 may be configured to add a category label associated with a shared category to comprehensive instruction set 206, where addition of the label may include addition of the label and/or a datum linked to the label, such as a textual or narrative description. In an embodiment, relationships between alimentary instruction set labels and categories may be retrieved from a alimentary instruction set label classification database 1600, for instance by generating a query using one or more alimentary instruction set labels of at least a alimentary instruction set output, entering the query, and receiving one or more categories matching the query from the alimentary instruction set label classification database 1600. In one embodiment, the alimentary instruction set label classification database 1600 is configured to generate queries based on preferences of user 202. Preferences may be based upon religious, dietary (vegan/gluten-free), lifestyle, or any other applicable factor associated with user 202 that is able to be manifested in the alimentary instruction set.

In one embodiment, alimentary instruction set generation module 120 may be configured to generate alimentary instruction set process descriptor 1428 by converting one or more alimentary instruction set labels into narrative language. As a non-limiting example, nutrition plan generation module 120 may include and/or communicate with narrative language unit 1312, which may be configured to determine an element of narrative language associated with at least an alimentary instruction set label and include the element of narrative language in current alimentary instruction set label descriptor. Narrative language unit 1412 may implement this, without limitation, by using a language processing module 516 to detect one or more associations between alimentary instruction set labels, or lists of alimentary instruction set labels, and phrases and/or statements of narrative language. Alternatively or additionally, Narrative language unit 1412 may retrieve one or more elements of narrative language from narrative language database 1416, which may contain one or more tables associating alimentary instruction set labels and/or groups of alimentary instruction set labels with words, sentences, and/or phrases of narrative language. One or more elements of narrative language may be included in alimentary instruction set, for instance for display to a user as text describing a current alimentary instruction set status of the user. Alimentary instruction set process descriptor 1428 may further include one or more images; one or more images may be retrieved by nutrition plan generation module 120 from an image database 1420, which may contain one or more tables associating alimentary instruction set labels, groups of alimentary instruction set labels, alimentary instruction set process descriptors 1028, or the like with one or more images.

In an embodiment, relationships between alimentary labels and categories may be retrieved from an alimentary instruction label classification database 2000, for instance by generating a query using one or more alimentary labels of at least an alimentary output, entering the query, and receiving one or more categories matching the query from the alimentary instruction label classification database 2000.

Figure 21:
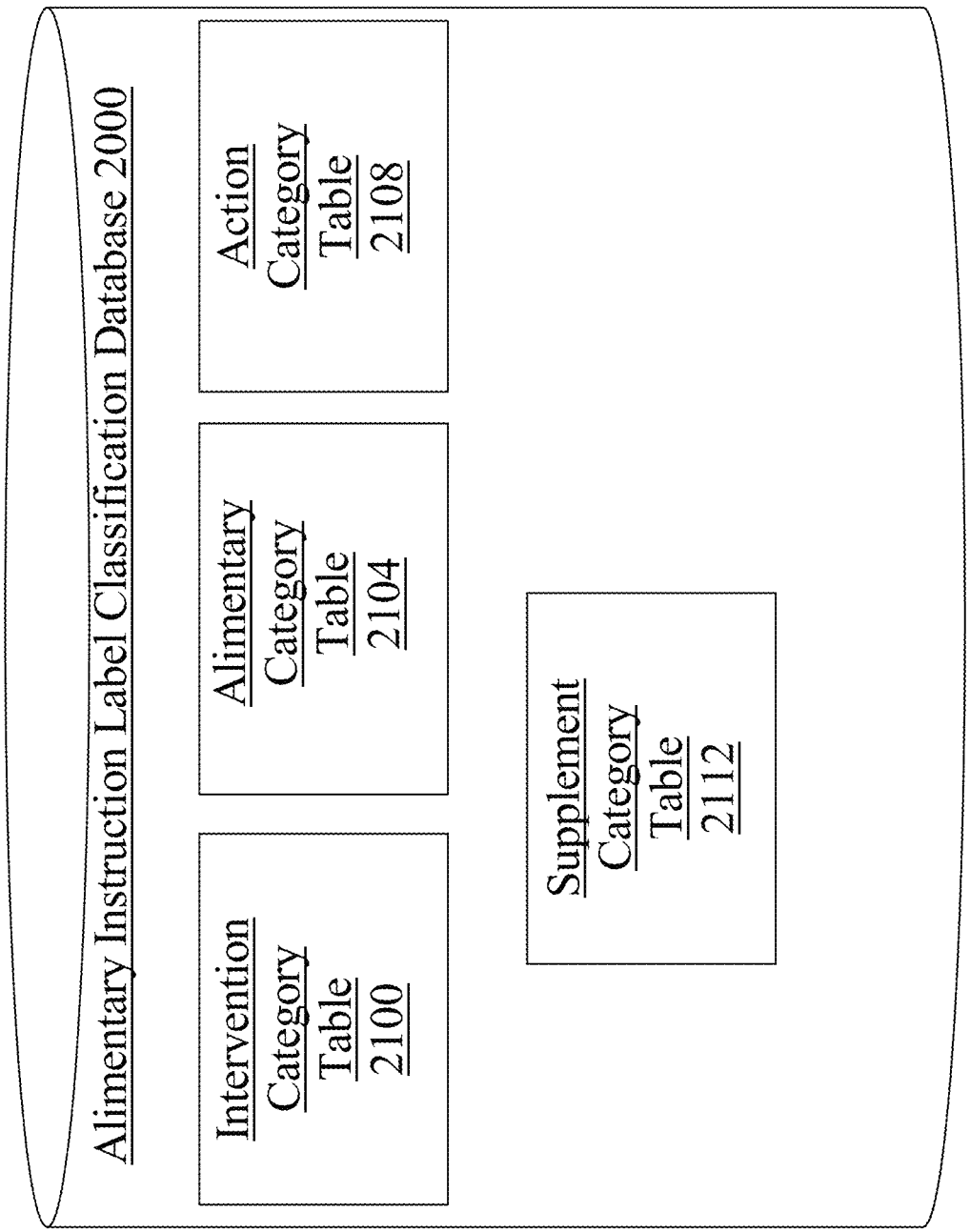
FIG. 21 is a block diagram illustrating an exemplary embodiment of an alimentary instruction label classification database.

Referring now to FIG. 21, an exemplary embodiment of an alimentary instruction label classification database 2000 is illustrated. Alimentary instruction label classification database 2000 may operate on the diagnostic engine 108. Alimentary instruction label classification database 2000 may be implemented as any database and/or datastore suitable for use as biological extraction database 600 as described above. One or more database tables in alimentary instruction label classification database 2000 may include, without limitation, an intervention category table 2100; an intervention may relate each alimentary label to one or more categories of conditions to be addressed by an alimentary instruction associated with that alimentary label, such as a nutritional imbalance to be corrected or the like. One or more database tables in alimentary instruction label classification database 2000 may include, without limitation, an alimentary category table 2004; which may associate an alimentary instruction label with one or more categories of nutritional properties, foodstuffs, or the like. One or more database tables in alimentary instruction label classification database 2000 may include, without limitation, an action category table 2108, which may describe one or more categories of actions, such as calorie reduction, sugar intake reduction, or the like, to which a given alimentary instruction may belong. One or more database tables in alimentary instruction label classification database 2000 may include, without limitation, a supplement table 2112, which may describe a supplement that relates to a nutritional need filled by an alimentary instruction.

Figure 22:
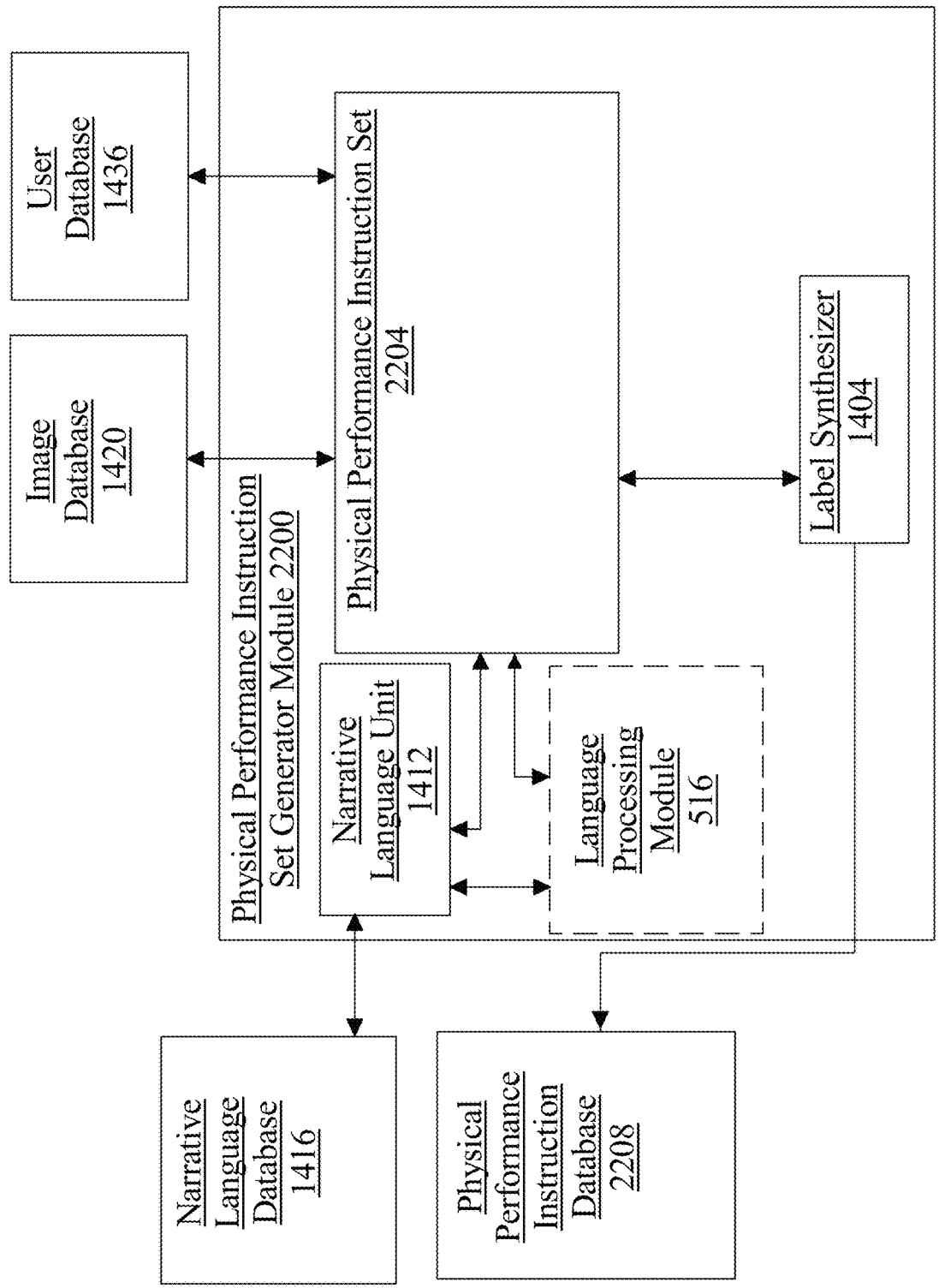
FIG. 22 is a block diagram illustrating an exemplary embodiment of a physical performance instruction set generation module.

Referring now to FIG. 22, a physical performance instruction set generator module 2200 is illustrated. Physical performance instruction set generator module 2200 may include any hardware or software module as described above; physical performance instruction set generation module 2200 may execute on at least a server. Physical performance instruction set generator module 2200 is configured to generate a physical performance instruction set 2204 based on components of alimentary instruction set 208. In one embodiment, physical performance instruction set 2204 is received by physical performance entity network 302 in order to be performed by physical performance entity 304 or an applicable third-party entity. In the case that physical performance entity 304 is not able to accomplish alimentary plan fulfillment network 300, physical performance entity 304 or vibrant constitutional network 200 may automatically reroute physical performance instruction set 2204 to an alternative physical performance entity capable of accomplishing alimentary plan fulfillment based on performances 210-216. In one embodiment, the rerouting of physical performance instruction set 2204 may be performed by physical performance instruction set generator module 2200.

In one exemplary use case, and with continued reference to FIG. 22, user 202 may manually select one or more of performances 210-216 from alimentary instruction set 208, and the applicable physical performance entity may be selected for execution of one of performances 210-216 based on a query of one or more of the databases of system 100 which is subsequently fulfilled. For example, user 202 may desire to order only a specific food provided within alimentary instruction set 208, in which upon a query tailored towards the specific food a database within system 100 comprising the applicable data associated with physical performance entity 308 configured to satisfy alimentary plan fulfillment network 300 provides the relevant data that allows performance instruction set generator module 2200 to generate physical performance instruction set 2204. Physical performance instruction set 2204 may performed by a physical performance device associated with a physical performance entity profile. The physical performance entity profile may be network hosted or a compilation of attributes for a connection to physical performance entity 304. The physical performance entity profile may also be an account associated with a third-party entity that specializes in one or more particular performances that may rendered for alimentary instruction set 208. In one embodiment, queries of the databases in system 100 may be administered based on the preferences of user 202 in which applicable data is extracted from the source that is capable of fulfilling the query and the applicable data is integrated with Physical performance instruction set 2204 by physical performance instruction set generator module 2200. In an embodiment, physical performance instruction set generator 2200 may return more than one physical performance entity 308 matching user requirements and/or requirements of physical performance instruction set 2204; physical performance instruction set generator 2200 may, in such a situation, present a user with a list of physical performance entities, enabling user to select one or more entities. Alternatively or additionally, where more than one entity is returned, user may be prompted or permitted to enter one or more user instructions specifying user preferences and/or criteria; one or more entities may then be filtered accordingly to generate a smaller list. The above-described process may be performed iteratively, permitting a user to continue narrowing a list of entities down by entering instructions that increasingly optimize the choice presented for final selection. Physical performance instruction set generator 2200 may then generate a set of instructions for a selected physical performance entity to perform. Instructions may include, without limitation, specification of ingredients, style of preparation, degree of preparation, seasoning, quantity, address information for physical movement of an alimentary preparation to a location specified by user and/or retrieved from user database 1436. As a non-limiting example, a user may be presented in alimentary instruction set 208 with a list of a number of potential meals, having particular quantities of required alimentary elements such as nutrients determined to have an ameliorative effect as described above; user may specify a desired meal from such a list, which may then trigger the above-described process, wherein the user's preferences regarding particular seasoning, degree of doneness, and the like may be collected initially, stored beforehand in user database 1436, and/or provided by the user at other stages in the above-described process.

Alternatively or additionally, and still referring to FIG. 22, physical performance entity may include a user for whom alimentary instruction set 208 was generated; in this case, Physical performance instruction set 2204 may include one or more user-performance instructions. User performance instructions may include any instructions that inform a user how to consume an alimentary element according to alimentary instruction set 208; for instance, and without limitation, physical performance instruction set may provide user with a set of ingredients needed to prepare a meal selected by the user from the alimentary instruction set 208. As a further non-limiting example, physical performance instruction set may provide one or more instructions informing a user of at least a physical performance entity whereby user may acquire ingredients, such as without limitation a grocery store, grocery delivery service, premade meal delivery service, or the like; instruction describing at least a physical performance entity may be generated according to any means or method as described above, including identification of one or more entities, filtered according to user preferences.

Still referring to FIG. 22, physical performance instruction set may include one or more navigation instructions, informing a user how to arrive at an institution associated with a physical performance entity. Physical performance instruction set may include one or more preparation instructions informing a user how to prepare an alimentary item, including cooking, storage, or other instructions. Physical performance instruction set may provide recommendations based on alimentary instruction set 208; for instance, physical performance instruction set generator 2200 may identify one or more alimentary needs based on alimentary instruction set 208, compare the one or more alimentary needs to one or more recent meals consumed by the user, identify one or more alimentary needs not addressed by the one or more recent meals, and provide a list of one or more meals and/or meal components to furnish the unmet needs. For instance, if alimentary instruction set 208 calls for user to consume a certain quantity of a given nutriment per day, and user has selected a first meal that does not provide the required quantity, physical performance instruction set generator 2200 may generate one or more meal proposals to provide the required quantity in remaining meals.

Continuing to refer to FIG. 22, physical performance instruction set generator 2200 may utilize any component or components as described above in generating physical performance instruction set 2204. For instance, and without limitation, narrative language database 1416 and/or Image database 1420 may contain narrative description, images, and/or videos; physical performance instruction set generator 2200 may retrieve one or more such elements of description, images, and/or videos, for instance using narrative language unit 1412, label synthesizer 1404, and/or language processing module 516, according to any process or process steps described above. In an embodiment, one or more physical instructions may be generated using information retrieved from a physical instruction database 2208, for instance by generating a query using one or more alimentary labels of at least an alimentary output, entering the query, and receiving one or more instructions matching the query from the physical instruction database 2208.

Figure 23:
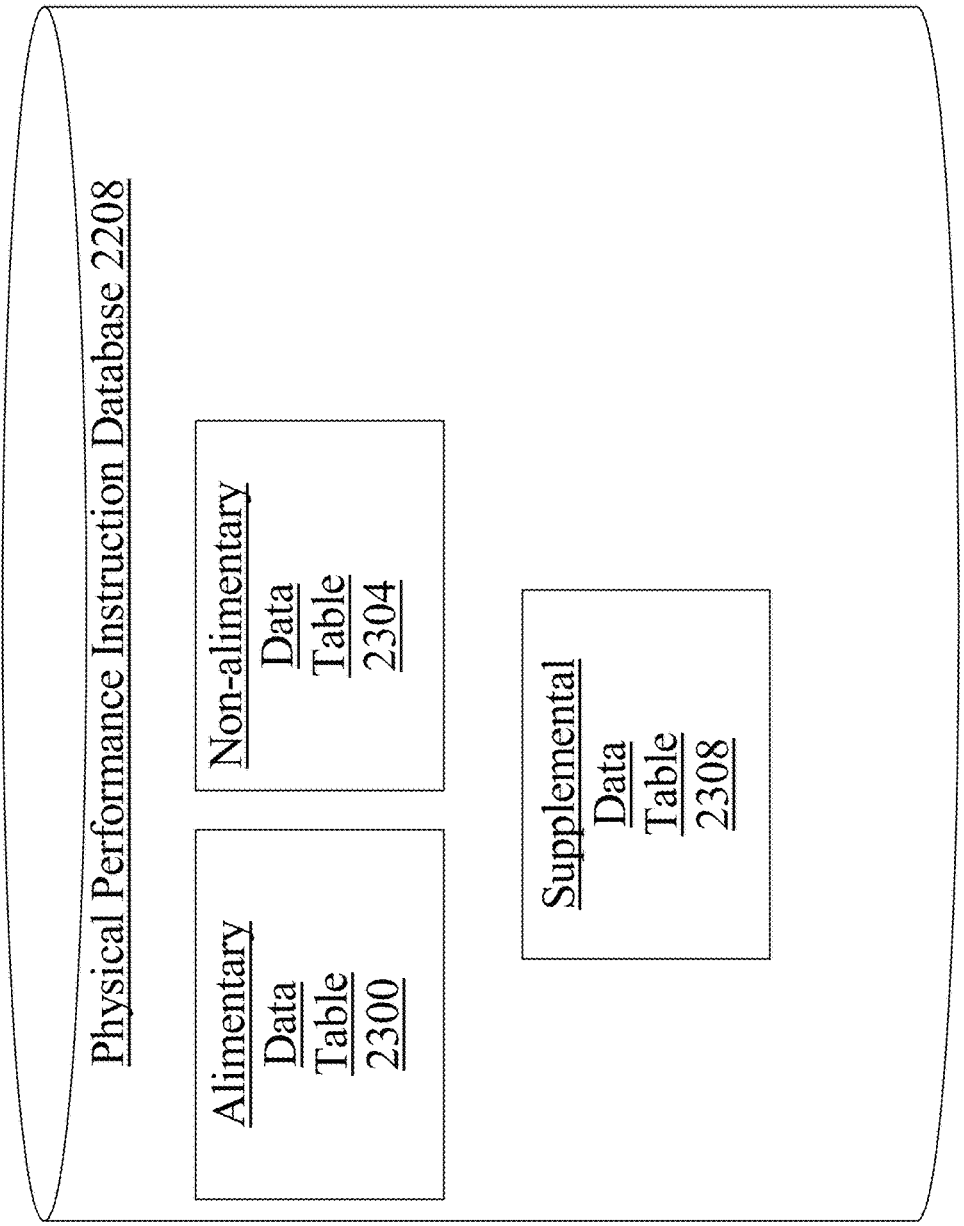
FIG. 23 is a block diagram illustrating an exemplary embodiment of a physical performance instruction database.

Referring now to FIG. 23, an exemplary embodiment of a physical performance instruction database 2208 is illustrated. Physical performance instruction database 2208 may operate on the at least a server 104. Physical performance instruction database 2208 may be implemented as any database and/or datastore suitable for use as biological extraction database 600 as described above. Physical performance instruction database 2208 may be configured to be utilized by physical performance instruction set generator module 2200 in assisting with the generation of Physical performance instruction set 2204 based on alimentary instruction set 208. Alternatively or additionally, physical performance instruction database 2208 may retrieve one or more elements from any database within system 100. In another embodiment, data utilized to generate Physical performance instruction set 2204 may be sourced from any applicable database including data that may be integrated with specific data associated with user 202. Physical performance instruction database 2208 may be configured to be communicatively coupled to physical performance entity database 308 and/or any database within system 100. Physical performance instruction database 2208 may be configured to integrate data sourced from any database within system 100 with data associated with physical performance entity database 308. Physical performance instruction set database 2108 may comprise an alimentary data table 2300, a non-alimentary data table 2304, and supplemental data table 2308 intended for storing data associated with a third-party entity, which may be necessary to process or perform one or more components of physical performance instruction set 2204. In application, physical performance database 2208 is configured to be utilized by at least a server 104 in order for alimentary instruction set generation module 120 to generate one or more physical performance instructions sets configured to be executed by a physical performance device associated with physical performance entity network 302 or the third-party entity if applicable.

In one embodiment, and still referring to FIG. 23, physical performance instruction database 2208 may be configured to include a plurality of data associated with comprehensive instruction set 2108 and alimentary instruction set 208. Physical performance instruction database 2208 may include data associated with physical performance entity 304 configured to be utilized in the generation of one or more physical performance instruction sets. One or more physical performance instruction sets are configured to be sets of instructions reflecting an integration of orders/requests associated with performances 210-216 along with data associated with physical performance entity 304. In application, performances 210-216 are established by components of comprehensive instruction set 206 and alimentary instruction set 208. For example, performances 210-216 may be actions established by a meal plan for user 202 based off an objective of alimentary instruction set 208 to lower the sugar intake of user 202 where performance 210 is an order for a specific item. Based on performance 210, physical performance entity 304 receives one or more physical performance instruction sets, via a physical performance device associated with physical performance entity 304, that may comprise a plurality of data associated with comprehensive instruction set 206, alimentary instruction set 208, and physical performance entity network 302. In this example, the order for the specific item may be automatically processed by physical performance entity 304 by collecting relevant data from physical performance database 2108 and vibrant constitutional network 200.

Referring again to FIG. 1, vibrant constitutional network system may include a client-interface module 128. Client-interface module 128 may include any suitable hardware or software module. Client-interface module 128 is designed and configured to transmit comprehensive instruction set 206 to at least a user client device 132 associated with the user. A user client device 132 may include, without limitation, a display in communication with diagnostic engine 108; display may include any display as described in this disclosure. A user client device 132 may include an addition computing device, such as a mobile device, laptop, desktop computer, or the like; as a non-limiting example, the user client device 132 may be a computer and/or workstation operated by a medical professional. Output may be displayed on at least a user client device 132 using an output graphical user interface; output graphical user interface may display at least a current prognostic descriptor 1400, at least a future prognostic descriptor 1424, and/or at least an alimentary instruction set process descriptor 1428.

With continued reference to FIG. 1, vibrant constitutional network system may include at least an advisory module 132 executing on the at least a server 104. At least an advisory module may include any suitable hardware or software module. In an embodiment, at least an advisory module is designed and configured to generate at least an advisory output as a function of the comprehensive instruction set 206 and/or alimentary instruction set 208 and transmit the advisory output to at least an advisor client device 140. At least an advisor client device 140 may include any device suitable for use as a user client device 132 as described above. At least an advisor client device 140 may be a user client device 132 as described above; that is, at least an advisory output may be output to the user client device 132. Alternatively or additionally, at least an advisor client device 140 may be operated by an informed advisor, defined for the purposes of this disclosure as any person besides the user who has access to information useable to aid user in interaction with vibrant constitutional network system. An informed advisor may include, without limitation, a medical professional such as a doctor, nurse, nurse practitioner, functional medicine practitioner, any professional with a career in medicine, nutrition, genetics, fitness, life sciences, insurance, and/or any other applicable industry that may contribute information and data to system 100 regarding medical needs. An informed advisor may include a spiritual or philosophical advisor, such as a religious leader, pastor, imam, rabbi, or the like. An informed advisor may include a physical fitness advisor, such as without limitation a personal trainer, instructor in yoga or martial arts, sports coach, or the like.

Figure 24:
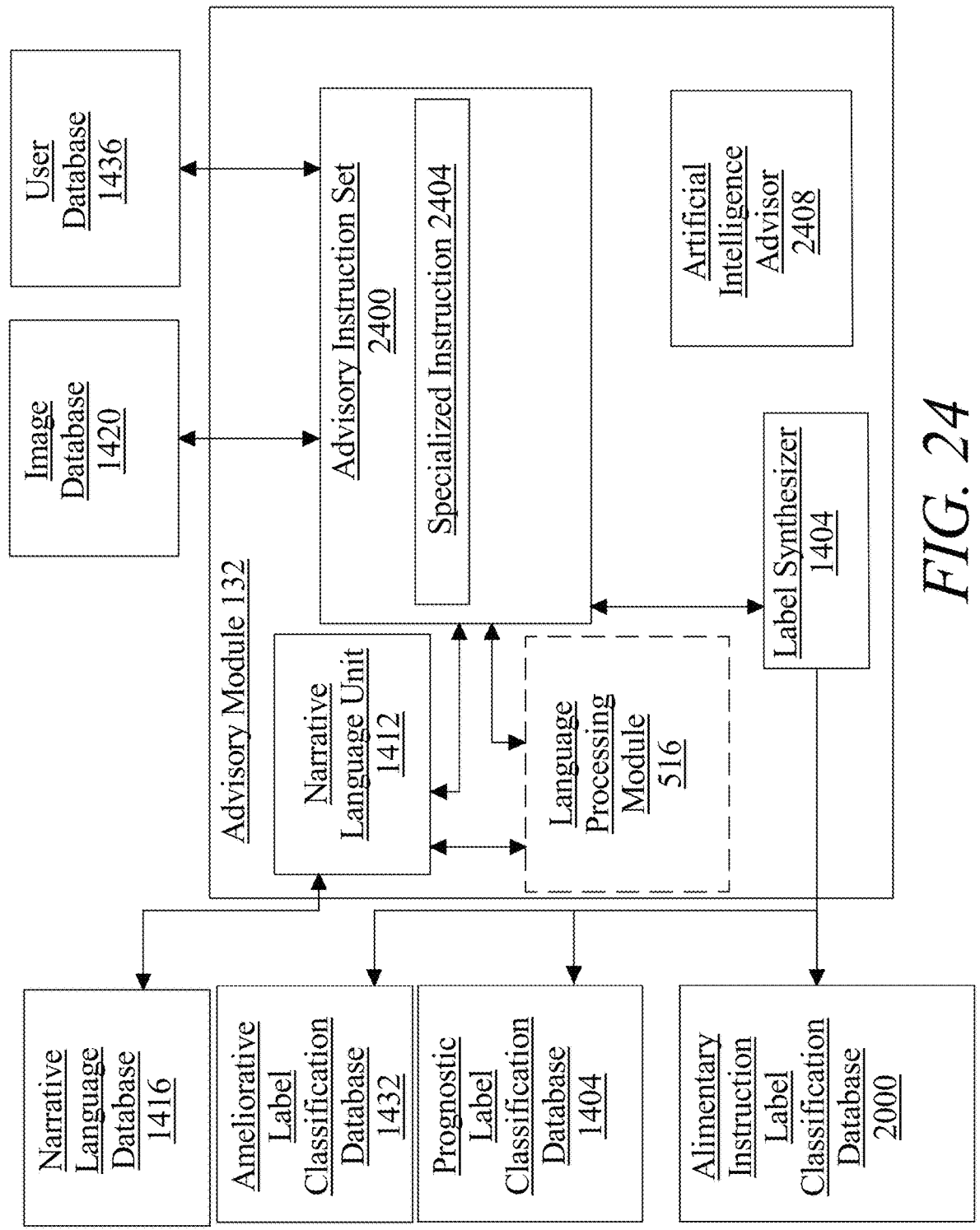
FIG. 24 is a block diagram illustrating an exemplary embodiment of an advisory module and associated system elements.

Referring now to FIG. 24, an exemplary embodiment of an advisory module 132 is illustrated. Advisory module 132 may be configured to generate an Advisory instruction set 2400 as a function of the diagnostic output. Advisory instruction set 2400 may contain any element suitable for inclusion in comprehensive instruction set 206; advisory module 132; Advisory instruction set 2400 and/or any element thereof may be generated using any process suitable for generation of comprehensive instruction set 206. Advisory instruction set 2400 may include one or more specialized instructions 2304; specialized instructions, as used herein, are instructions the contents of which are selected for display to a particular informed advisor. Selection of instructions for a particular informed advisor may be obtained, without limitation, from information concerning the particular informed advisor, which may be retrieved from a user database 1436 or the like. As a non-limiting example, where an informed advisor is a doctor, specialized instruction 2304 may include data from biological extraction as described above; specialized instruction may include one or more medical records of user, which may, as a non-limiting example, be downloaded or otherwise received from an external database containing medical records and/or a database (not shown) operating on at least a server 104. As a further non-limiting example medical data relevant to fitness, such as orthopedic reports, may be provided to an informed advisor whose role is as a fitness instructor, coach, or the like. Information provided to informed advisors may be extracted or received from any database described herein, including without limitation biological extraction database 600.

In an embodiment, and continuing to refer to FIG. 24, advisory module 132 may be configured to receive at least an advisory input from the advisor client device 140. At least an advisory input may include any information provided by an informed advisor via advisor client device 140. Advisory input may include medical information and/or advice. Advisory input may include user data, including user habits, preferences, religious affiliations, constitutional restrictions, or the like. Advisory input may include spiritual and/or religious advice. Advisory input may include user-specific diagnostic information. Advisory input may be provided to user client device 132; alternatively or additionally, advisory input may be fed back into system 100, including without limitation insertion into user database 1436, inclusion in or use to update diagnostic engine 108, for instance by augmenting machine-learning models and/or modifying machine-learning outputs via a lazy-learning protocol or the like as described above.

With continued reference to FIG. 24, advisory module 132 may include an artificial intelligence advisor 2408 configured to perform a user textual conversation with the user client device 132. Artificial intelligence advisor 2408 may provide output to advisor client device 140 and/or user client device 132. Artificial intelligence advisor 2408 may receive inputs from advisor client device 140 and/or user client device 132. Inputs and/or outputs may be exchanged using messaging performances and/or protocols, including without limitation any instant messaging protocols. Persons skilled in the art, up reviewing the entirety of this disclosure, will be aware of a multiplicity of communication protocols that may be employed to exchange text messages as described herein. Text messages may be provided in textual form and/or as audio files using, without limitation, speech-to-text and/or text-to-speech algorithms.

Referring again to FIG. 1, system 100 includes an alimentary instruction set generator module 120 operating on at least a server 104. Alimentary instruction set generator module 120 may include any hardware or software module suitable for use as a plan generator module 112. Alimentary instruction set generator module may interact with plan generator module 112. For instance, and without limitation, alimentary instruction set generator module 120 may be configured to generate, based on comprehensive instruction set 206, an alimentary instruction set associated with the user. In one embodiment, the alimentary instruction set generator module 120 is configured to generate one or more sets of instructions associated with the alimentary instruction set based on comprehensive instruction set 206. The one or more sets of instructions are configured to be performed on a physical performance device associated with physical performance entity 304. Physical performance device may comprise at least a descriptor configured to assist in the generation of a physical performance instruction set provided by at least a server 104.

Figure 25:
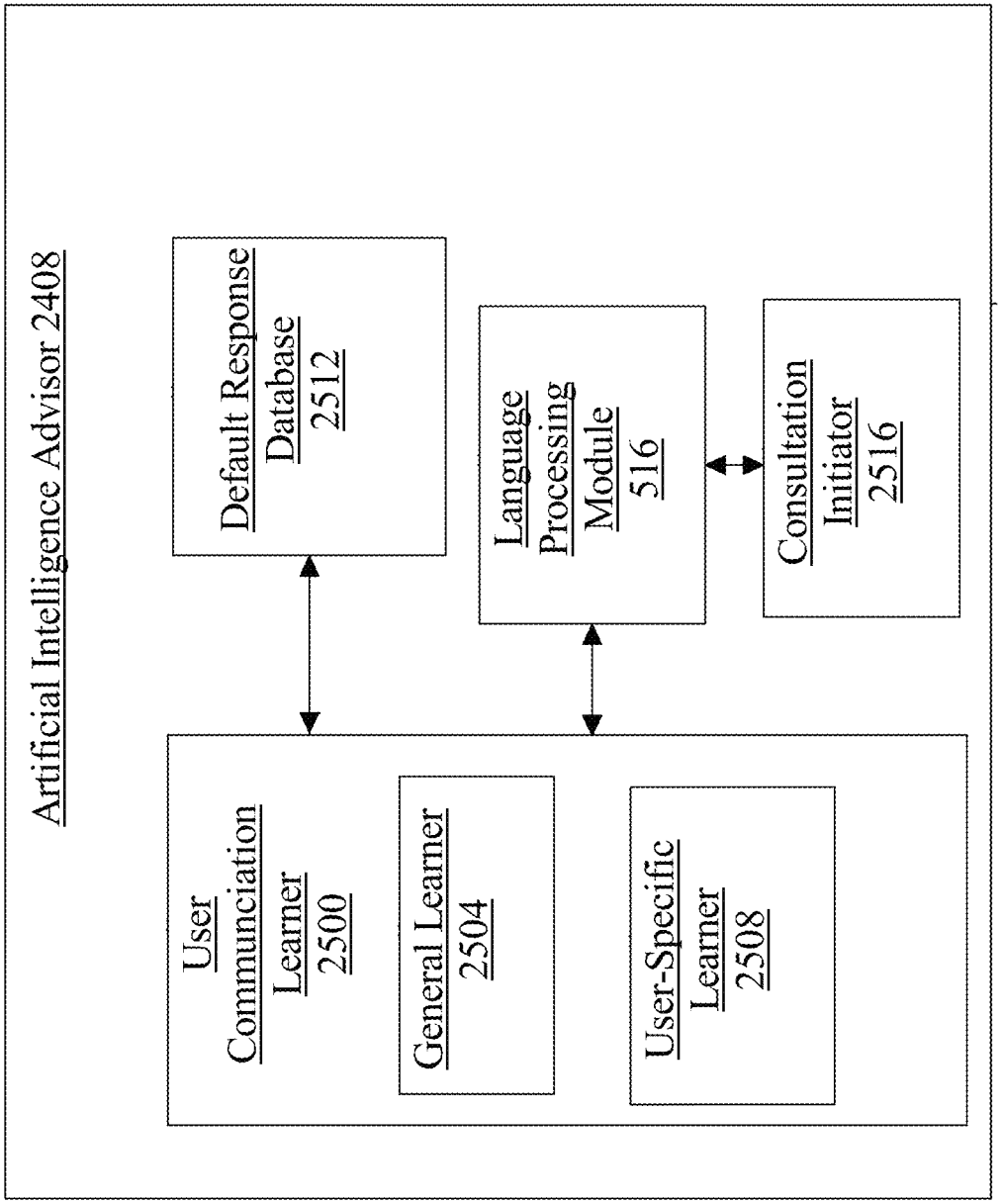
FIG. 25 is a block diagram illustrating an exemplary embodiment of an artificial intelligence advisor and associated system elements.

Referring now to FIG. 25, an exemplary embodiment of an artificial intelligence advisor 2408 is illustrated. Artificial intelligence advisor 2408 may include a user communication learner 2500. User communication learner 2500 may be any form of machine-learning learner as described above, implementing any form of language processing and/or machine learning. In an embodiment, User communication learner 2500 may include a general learner 2504; general learner 2504 may be a learner that derives relationships between user inputs and correct outputs using a training set that includes, without limitation, a corpus of previous conversations. Corpus of previous conversations may be logged by at least a server 104 as conversations take place; user feedback, and/or one or more functions indicating degree of success of a conversation may be used to differentiate between positive input-output pairs to use for training and negative input-output pairs not to use for training. Outputs may include textual strings and/or outputs from any databases, modules, and/or learners as described in this disclosure, including without limitation prognostic labels, prognostic descriptors, alimentary instruction set labels, alimentary instruction set descriptors, user information, or the like; for instance, general learner 2504 may determine that some inputs optimally map to textual response outputs, while other inputs map to outputs created by retrieval of module and/or database outputs, such as retrieval of prognostic descriptors, alimentary instruction set descriptors, or the like. User communication learner may include a user-specific learner 2508, which may generate one or more modules that learn input-output pairs pertaining to communication with a particular user; a user specific learner 2508 may initially use input-output pairs established by general learner 2504 and may modify such pairs to match optimal conversation with the particular user by iteratively minimizing an error function.

Still referring to FIG. 25, general learner 2504 and/or user-specific learner 2508 may initialize, prior to training, using one or more record retrieved from a default response database 2412. Default response database 2512 may link inputs to outputs according to initial relationships entered by users, including without limitation experts as described above, and/or as created by a previous instance or version of general learner 2504 and/or user-specific learner 2508. Default response database 2512 may periodically be updated with information from newly generated instances of general learner 2504 and/or user-specific learner 2508. Inputs received by artificial intelligence advisor 2408 may be mapped to canonical and/or representative inputs by synonym detection as performed, for instance, by a language processing module 516; language processing module 516 may be involved in textual analysis and/or generation of text at any other point in machine-learning and/or communication processes undergone by artificial intelligence advisor 2408.

Figure 26:
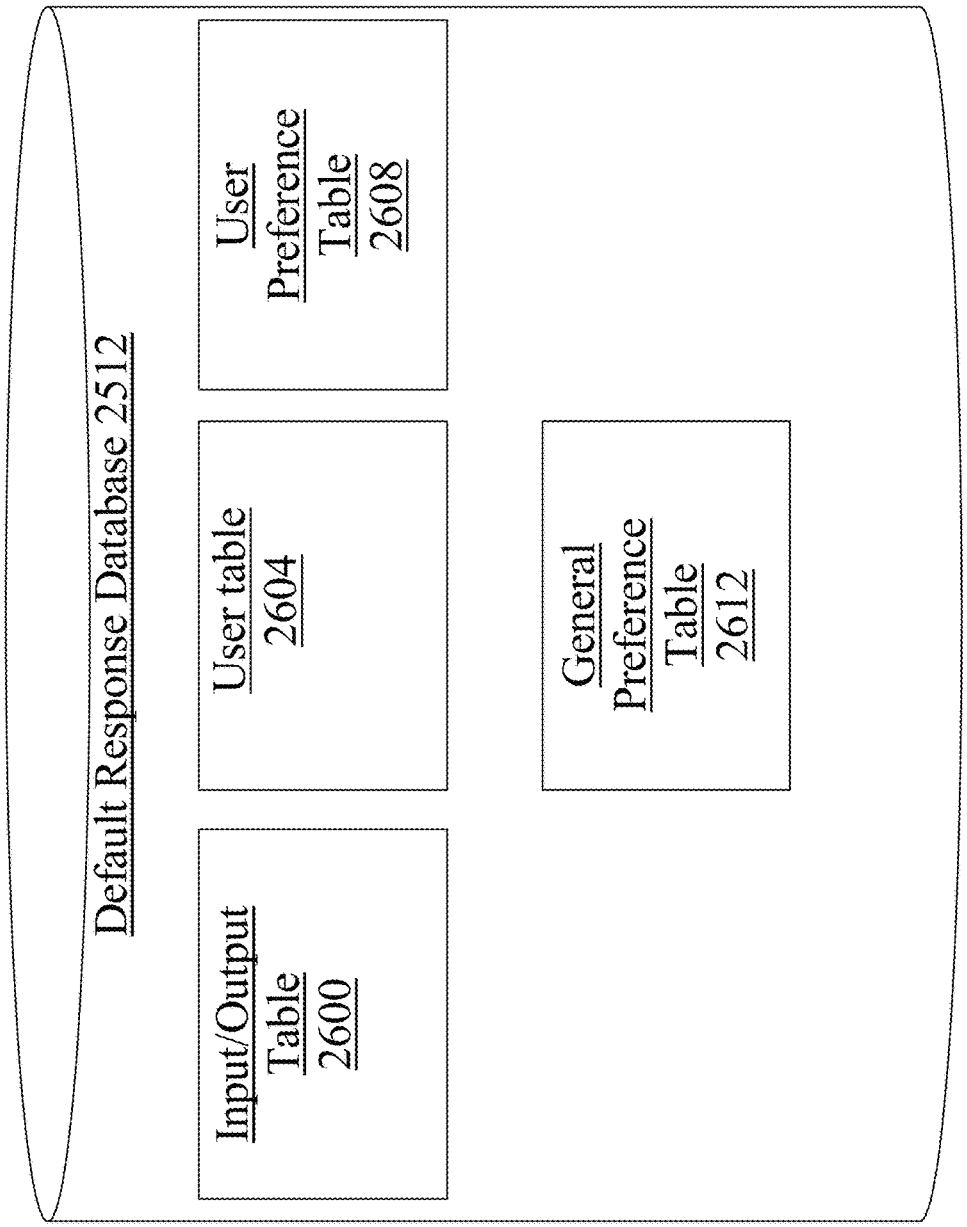
FIG. 26 is a block diagram illustrating an exemplary embodiment of a default response database.

Referring now to FIG. 26, an exemplary embodiment of a default response database 2512 is illustrated. Default response database 2512 may be implemented as any database and/or datastore suitable for use as biological extraction database 600 as described above. One or more database tables in default response database 2512 may include, without limitation, an input/output table 2600, which may link default inputs to default outputs. Default response database 2512 may include a user table 2604, which may, for instance, map users and/or a user client device 132 to particular user-specific learners and/or past conversations. Default response database 2512 may include a user preference table 2608 listing preferred modes of address, turns of phrase, or other user-specific communication preferences. Default response database 2512 may include a general preference table 2612, which may track, for instance, output-input pairings associated with greater degrees of user satisfaction.

Referring again to FIG. 25, artificial intelligence advisor may include a consultation initiator 2516 configured to detect a consultation event in a user textual conversation and initiate a consultation with an informed advisor as a function of the consultation event. A consultation event, as used herein, is a situation where an informed advisor is needed to address a user's situation or concerns, such as when a user should be consulting with a nutritionist or dietician seeking to assist user 202 with support pertaining to diet, lifestyle, and wellness, or with an advisor who can lend emotional support when particularly distraught. Detection may be performed, without limitation, by matching an input and/or set of inputs to an output that constitutes an action of initiating a consultation; such a pairing of an input and/or input set may be learned using a machine learning process, for instance via general learner and/or user specific learner 2508. In the latter case, information concerning a particular user's physical or emotional needs or condition may be a part of the training set used to generate the input/input set to consultation event pairing; for instance, a user with a history of heart disease may trigger consultation events upon any inputs describing shortness of breath, chest discomfort, arrhythmia, or the like. Initiation of consultation may include transmitting a message to an advisor client device 140 associated with an appropriate informed advisor, such as without limitation transmission of information regarding a potential medical emergency to a doctor able to assist in treating the emergency. Initiation of consultation may alternatively or additionally include providing an output to the user informing the user that a consultation with an informed advisor, who may be specified by name or role, is advisable.

Figure 27A:
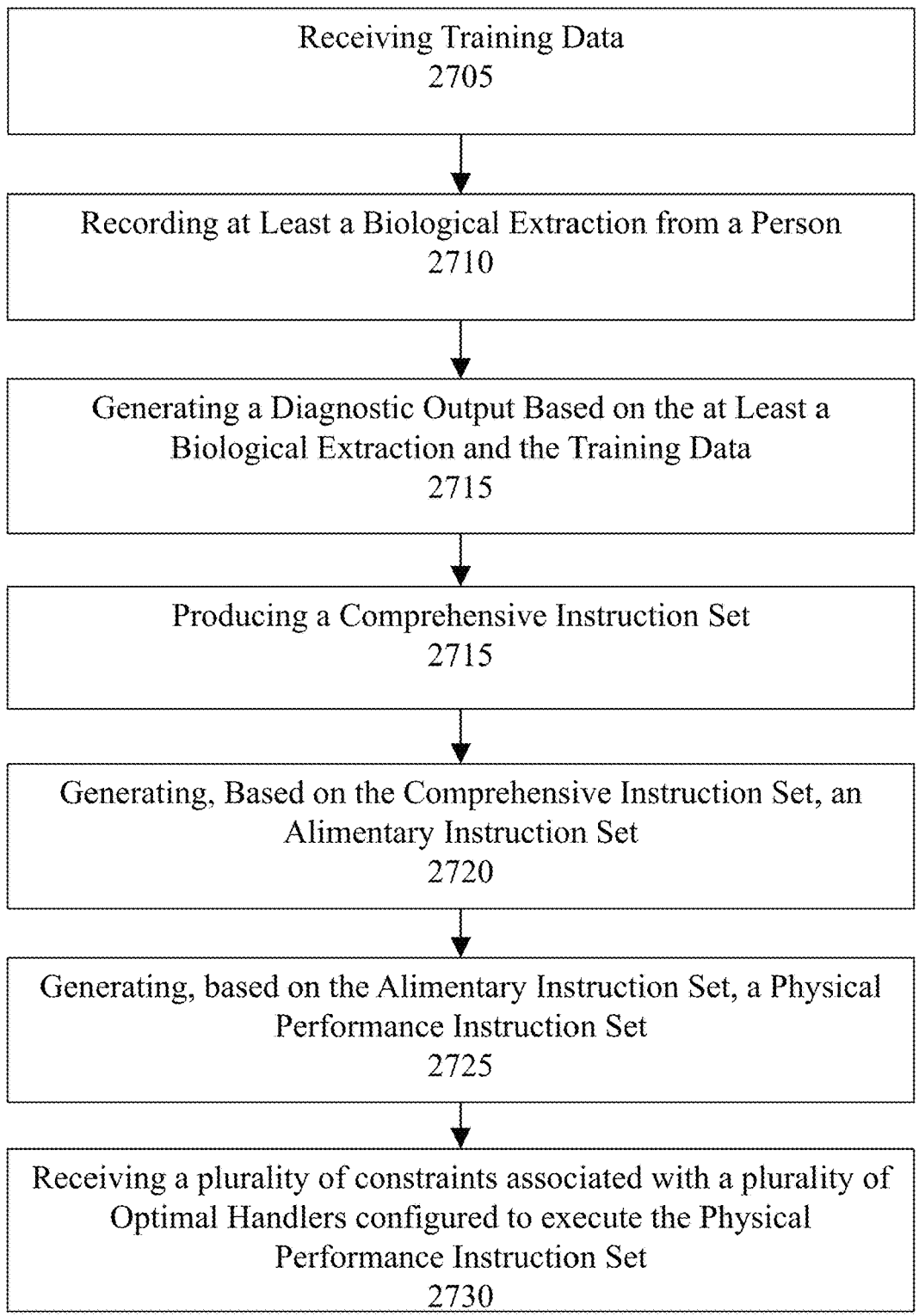
FIG. 27A-B are flow diagrams illustrating an exemplary method of implementing a generated alimentary instruction set.
Figure 27B:

Referring now to FIG. 27A-B, an exemplary embodiment of a method 2700 of implementing a generated alimentary instruction set 208 is illustrated. At step 2705, training data is received, wherein receiving the training data further comprises: receiving first training set 500 including a plurality of first data entries, each first data entry of the plurality of first data entries including at least a biological extraction datum and at least a correlated first prognostic label; and receiving second training set 520 including a plurality of second data entries, each second data entry of the plurality of second data entries including at least a second prognostic label and at least a correlated alimentary process label; this may be performed, without limitation, as described above in reference to FIGS. 1-26. At step 2710, at least a biological extraction from user 202 is recorded and a diagnostic output is generated based on the at least a biological extraction and the training data, wherein generating further comprises performing at least a machine-learning algorithm as a function of the training data and the at least a biological extraction; this may be performed, without limitation, as described above in reference to FIGS. 1-26. At step 2715, a comprehensive instruction set 206 is produced; this may be performed, without limitation, as described above in reference to FIGS. 1-26. At step 2720 alimentary instruction set 208 is generated based on comprehensive instruction set 206; this may be performed, without limitation, as described above in reference to FIGS. 1-26. At step 2727, a physical performance instruction set is generated based on alimentary instruction set 208; this may be performed, without limitation, as described above in reference to FIGS. 1-26. At 2730, the plurality of constraints associated with the plurality of optimal handlers is received; this may be performed, without limitation, as described above in reference to FIGS. 1-26. Generating comprehensive instruction set 206, alimentary instruction set 208, or the physical performance instruction set may include, as a further example, receiving at least an element of user data and filtering the diagnostic output using the at least an element of user data. At step 2735, an optimal handler is selected as a function of the plurality of constraints; this may be performed, without limitation, as described above in reference to FIGS. 1-26. At step 2740, a subset of data associated with user 202 is transmitted to the optimal handler; this may be performed, without limitation, as described above in reference to FIGS. 1-26.

Figure 28:
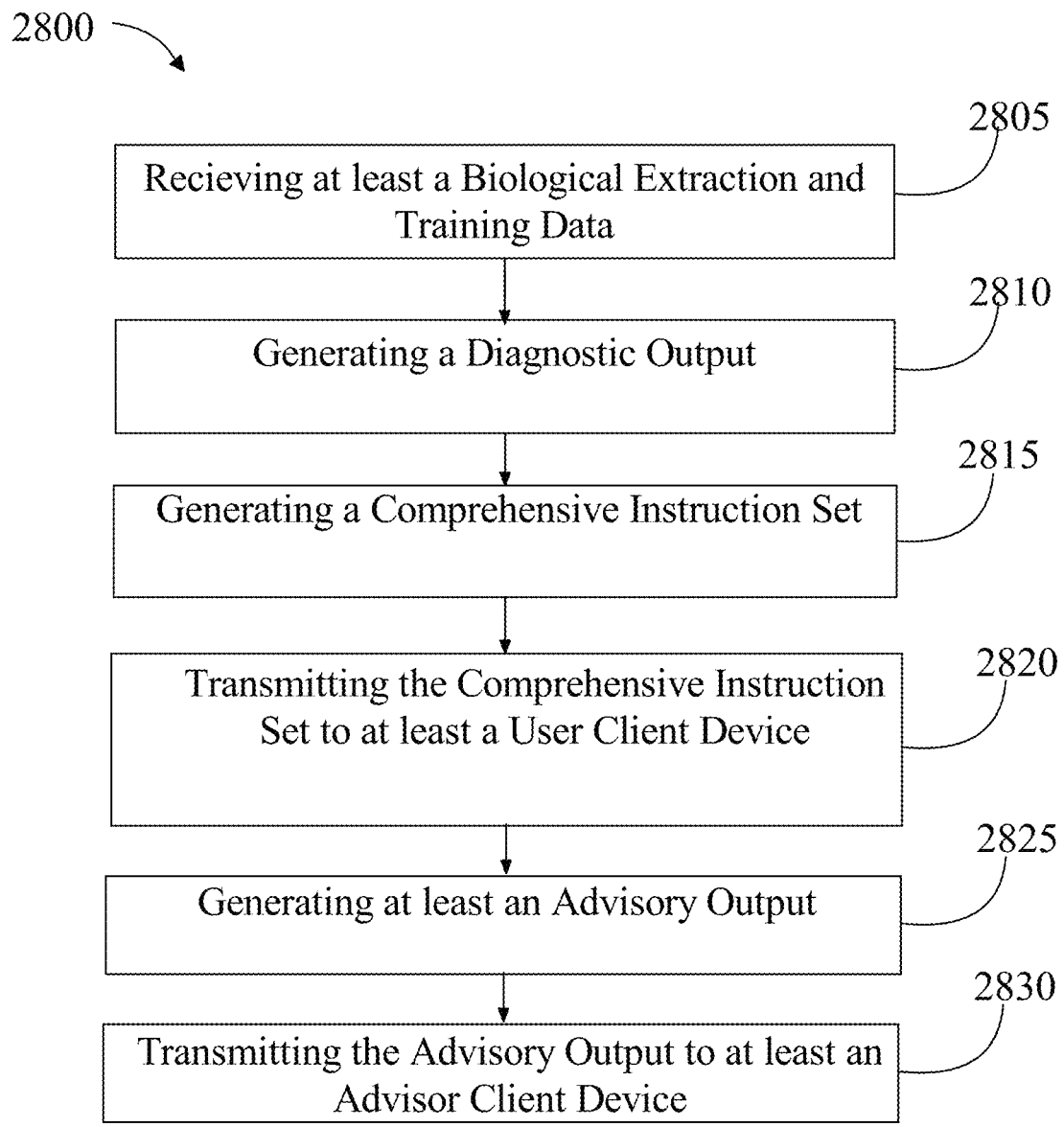
FIG. 28 is a flow diagram illustrating an exemplary method of implementing an alimentary instruction set based on vibrant constitutional guidance using artificial intelligence.

Referring now to FIG. 28, a method 2800 for implementing an alimentary instruction set based on vibrant constitutional guidance using artificial intelligence is shown. Method 2800 includes a step 2805 of receiving, at a diagnostic engine operating on the at least a server, at least a biological extraction from a user and training data. This may be performed, without limitation, as described above in reference to FIGS. 1-27. In some embodiments, the server may be part of a vibrant constitutional network system. In some embodiments, the server may include an alimentary instruction set generation module operating on the at least a server. In some embodiments, step 2805 may include receiving a first training set including a plurality of first data entries and a second training set including a plurality of second data entries. This may be performed, without limitation, as described above in reference to FIGS. 1-27.

With continued reference to FIG. 28, method 2800 includes a step 2810 of generating, at the diagnostic engine, a diagnostic output as a function of the at least a biological extraction and the training data. This may be performed, without limitation, as described above in reference to FIGS. 1-27. In some embodiments, step 2810 may include performing at least a machine-learning algorithm as a function of the training data and the at least a biological extraction. This may be performed, without limitation, as described above in reference to FIGS. 1-27.

With continued reference to FIG. 28, method 2800 includes a step 2815 of generating, at a plan generation module operating on the at least a server, a comprehensive instruction set associated with the user based on the diagnostic output. This may be performed, without limitation, as described above in reference to FIGS. 1-27.

With continued reference to FIG. 28, method 2800 includes a step 2820 of transmitting, at a client-interface module operating on the at least a server, the comprehensive instruction set to at least a user client device associated with the user. This may be performed, without limitation, as described above in reference to FIGS. 1-27.

With continued reference to FIG. 28, method 2800 includes a step 2825 of generating, at an advisory module executing on the at least a server, at least an advisory output as a function of the comprehensive instruction set. This may be performed, without limitation, as described above in reference to FIGS. 1-27.

With continued reference to FIG. 28, method 2800 includes a step 2830 of transmitting, at the advisory module, the advisory output to at least an advisor client device. This may be performed, without limitation, as described above in reference to FIGS. 1-27.

With continued reference to FIG. 28, method 2800, in some embodiments, may include a step of presenting, at a graphical user interface, a physical performance entity profile to the user. This may be performed, without limitation, as described above in reference to FIGS. 1-27. In some embodiments, method 2800 may include a step of generating, at the alimentary instruction set generator, based on the comprehensive instruction set, an alimentary instruction set associated with the user. This may be performed, without limitation, as described above in reference to FIGS. 1-27. In some embodiments, method 2800 may include a step of generating at a physical performance instruction set generator module, based on the alimentary instruction set, a physical performance instruction set. This may be performed, without limitation, as described above in reference to FIGS. 1-27. In some embodiments, generating the physical performance instruction set may include receiving a plurality of constraints associated with a plurality of optimal handlers configured to execute the physical performance instruction set. This may be performed, without limitation, as described above in reference to FIGS. 1-27. In some embodiments, generating the physical performance instruction set may include selecting at least an optimal handler from the plurality of optimal handlers as a function of the plurality of constraints. This may be performed, without limitation, as described above in reference to FIGS. 1-27. In some embodiments, generating the physical performance instruction set may include transmitting a subset of data associated with the user to the at least an optimal handler. This may be performed, without limitation, as described above in reference to FIGS. 1-27. In some embodiments, method 2800 may include a step of performing, at an artificial intelligence advisor or the advisory module, a user textual conversation with the user client device. This may be performed, without limitation, as described above in reference to FIGS. 1-27.

Systems and methods described herein may provide improvements to the processing, storage, and utility of data collected along with a centralized vibrant constitutional advice network configured to develop alimentary plans for users, and execute processes and performances based on components of the alimentary plans. By using a rule-based model or a machine-learned model to generate feature values of data contained within the collected data, one or more analyses are performed on the feature values, and outputs of training data are generated and included in an optimized set of data. The optimized set of data is used to generate the alimentary plans, and the vibrant constitutional advice network is able to provide users with not only a method of acquiring detailed information regarding nourishment of a user, but more importantly the ability to make decisions that support vibrant constitution and longevity influenced by the plurality of information based on the collected data. Furthermore, the systems and methods provide an unconventional use of the plurality of collected data via automatic execution of processes and performances by the vibrant constitutional advice network based on the generated alimentary plans. Thus, the systems and methods described herein improve the functioning of computing systems by optimizing big data processing and improving the utility of the processed big data via its unconventional application.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 29:
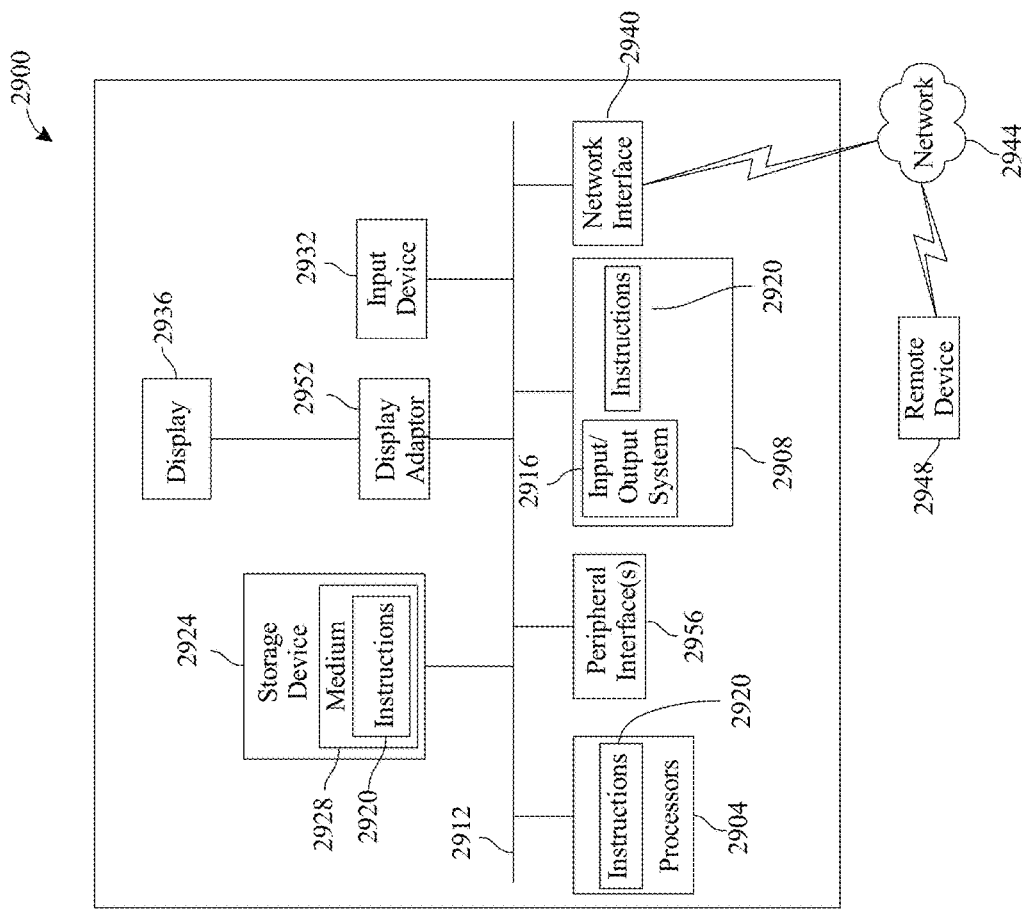
FIG. 29 is a block diagram of a computing system that can be used to implement any one or more of the methodologies disclosed herein and any one or more portions thereof.

FIG. 29 shows a diagrammatic representation of one embodiment of a computing device in the exemplary form of a computer system 2900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2900 includes a processor 2904 and a memory 2908 that communicate with each other, and with other components, via a bus 2912. Bus 2912 may include any of several types of bus structures including, but not limited to, a memory bus, a memory controller, a peripheral bus, a local bus, and any combinations thereof, using any of a variety of bus architectures.

Processor 2904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 2904 may be organized according to Von Neumann and/or Harvard architecture as a non-limiting example. Processor 2904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 2908 may include various components (e.g., machine-readable media) including, but not limited to, a random-access memory component, a read only component, and any combinations thereof. In one example, a basic input/output system 2916 (BIOS), including basic routines that help to transfer information between elements within computer system 2900, such as during start-up, may be stored in memory 2908. Memory 2908 may also include (e.g., stored on one or more machine-readable media) instructions (e.g., software) 2920 embodying any one or more of the aspects and/or methodologies of the present disclosure. In another example, memory 2908 may further include any number of program modules including, but not limited to, an operating system, one or more application programs, other program modules, program data, and any combinations thereof.

Computer system 2900 may also include a storage device 2924. Examples of a storage device (e.g., storage device 2924) include, but are not limited to, a hard disk drive, a magnetic disk drive, an optical disc drive in combination with an optical medium, a solid-state memory device, and any combinations thereof. Storage device 2924 may be connected to bus 2912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2924 (or one or more components thereof) may be removably interfaced with computer system 2900 (e.g., via an external port connector (not shown)). Particularly, storage device 2924 and an associated machine-readable medium 2928 may provide nonvolatile and/or volatile storage of machine-readable instructions, data structures, program modules, and/or other data for computer system 2900. In one example, software 2920 may reside, completely or partially, within machine-readable medium 2928. In another example, software 2920 may reside, completely or partially, within processor 2904.

Computer system 2900 may also include an input device 2932. In one example, a user of computer system 2900 may enter commands and/or other information into computer system 2900 via input device 2932. Examples of an input device 2932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2932 may be interfaced to bus 2912 via any of a variety of interfaces (not shown) including, but not limited to, a serial interface, a parallel interface, a game port, a USB interface, a FIREWIRE interface, a direct interface to bus 2912, and any combinations thereof. Input device 2932 may include a touch screen interface that may be a part of or separate from display 2936, discussed further below. Input device 2932 may be utilized as a user selection device for selecting one or more graphical representations in a graphical interface as described above.

A user may also input commands and/or other information to computer system 2900 via storage device 2924 (e.g., a removable disk drive, a flash drive, etc.) and/or network interface device 2940. A network interface device, such as network interface device 2940, may be utilized for connecting computer system 2900 to one or more of a variety of networks, such as network 2944, and one or more remote devices 2948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 2944, may employ a wired and/or a wireless mode of communication. In general, any network topology may be used. Information (e.g., data, software 2920, etc.) may be communicated to and/or from computer system 2900 via network interface device 2940.

Computer system 2900 may further include a video display adapter 2952 for communicating a displayable image to a display device, such as display device 2936. Examples of a display device include, but are not limited to, a liquid crystal display (LCD), a cathode ray tube (CRT), a plasma display, a light emitting diode (LED) display, and any combinations thereof. Display adapter 2952 and display device 2936 may be utilized in combination with processor 2904 to provide graphical representations of aspects of the present disclosure. In addition to a display device, computer system 2900 may include one or more other peripheral output devices including, but not limited to, an audio speaker, a printer, and any combinations thereof. Such peripheral output devices may be connected to bus 2912 via a peripheral interface 2956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for implementing an alimentary instruction set based on vibrant constitutional guidance using artificial intelligence, the system comprising at least a server configured to:

receive, at a diagnostic engine operating on the at least a server, at least a biological extraction from a user and training data;

generate, at the diagnostic engine, a diagnostic output as a function of the at least a biological extraction and the training data;

generate, at a plan generation module operating on the at least a server, a comprehensive instruction set associated with the user based on the diagnostic output;

generate, at an alimentary instruction set generation module operating on the at least a server, an alimentary instruction set associated with the user based on the comprehensive instruction set, wherein generating the alimentary instruction set comprises:

identifying a plurality of alimentary components associated with the user;

identifying at least one negative effect associated with at least one instruction of the comprehensive instruction set; and determining an alimentary instruction that alleviates the at least one negative effect as a function of the at least one negative effect using a machine-learning process;

generate, at a physical performance instruction set generator module operating on the at least a server, a physical performance instruction set based on the alimentary instruction set including the alimentary instruction that alleviates the at least one negative effect, wherein generating the physical performance instruction set comprises:

identifying one or more alimentary components of the plurality of alimentary components to be physically transported to the user;

receive, at a physical performance entity network on the at least a server, the physical performance instruction set, the alimentary instruction set and a plurality of information pertaining to the user;

receive, at the at least a server, a plurality of constraints from one or more physical performance entities and preferences of the user, wherein the at least a server automatically selects one or more optimal handlers to execute the physical performance instruction set as a function of the plurality of constraints and the preferences of the user;

transmit, by the at least a server, a subset of data associated with the user to the physical performance entity network associated with the one or more selected optimal handlers;

continuously update, by the at least a server, the physical performance instruction set as a function of an updated alimentary instruction set, wherein the updated alimentary instruction set is updated by a vibrant constitutional network as a function of an updated comprehensive instruction set based on an updated diagnostic output and the alimentary instruction that alleviates the at least one negative effect;

transmit, at a client-interface module operating on the at least a server, the updated comprehensive instruction set to at least a user client device associated with the user;

generate, at an advisory module executing on the at least a server, at least an advisory output as a function of the updated comprehensive instruction set; and transmit, at the advisory module, the advisory output to at least an advisor client device.

2. The system of claim 1, wherein the system further includes the vibrant constitutional network.

3. The system of claim 1, wherein the system further includes a graphical user interface configured to present a physical performance entity profile to the user.

4. The system of claim 1, wherein the advisory module includes an artificial intelligence advisor configured to perform a user textual conversation with the user client device.

5. The system of claim 1, wherein receiving training data at the diagnostic engine includes receiving a first training set including a plurality of first data entries and a second training set including a plurality of second data entries.

6. The system of claim 1, wherein generating the diagnostic output further comprises performing at least a machine-learning algorithm as a function of the training data and the at least a biological extraction.

7. A method for implementing an alimentary instruction set based on vibrant constitutional guidance using artificial intelligence, the method performed by at least a server and comprising:

receiving, at a diagnostic engine operating on the at least a server, at least a biological extraction from a user and training data;

generating, at the diagnostic engine, a diagnostic output as a function of the at least a biological extraction and the training data;

generating, at a plan generation module operating on the at least a server, a comprehensive instruction set associated with the user based on the diagnostic output;

generating, at an alimentary instruction set generation module operating on the at least a server, an alimentary instruction set associated with the user based on the comprehensive instruction set, wherein generating the alimentary instruction set comprises:
identifying a plurality of alimentary components associated with the user;
identifying at least one negative effect associated with at least one instruction of the comprehensive instruction set; and
determining an alimentary instruction that alleviates the at least one negative effect as a function of the at least one negative effect using a machine-learning process;

generating, at a physical performance instruction set generator module operating on the at least a server, a physical performance instruction set based on the alimentary instruction set including the alimentary instruction that alleviates the at least one negative effect, wherein generating the physical performance instruction set comprises:
identifying one or more alimentary components of the plurality of alimentary components to be physically transported to the user;

receiving, at a physical performance entity network on the at least a server, the physical performance instruction set, the alimentary instruction set and a plurality of information pertaining to the user;

receiving, at the at least a server, a plurality of constraints from one or more physical performance entities and preferences of the user, wherein the at least a server automatedly selects one or more optimal handlers to execute the physical performance instruction set as a function of the plurality of constraints and the preferences of the user;

transmitting, by the at least a server, a subset of data associated with the user to the physical performance entity network associated with the one or more selected optimal handlers;

continuously updating, by the at least a server, the physical performance instruction set as a function of an updated alimentary instruction set, wherein the updated alimentary instruction set is updated by a vibrant constitutional network as a function of an updated comprehensive instruction set based on an updated diagnostic output and the alimentary instruction that alleviates the at least one negative effect;

transmitting, at a client-interface module operating on the at least a server, the updated comprehensive instruction set to at least a user client device associated with the user;

generating, at an advisory module executing on the at least a server, at least an advisory output as a function of the updated comprehensive instruction set; and transmitting, at the advisory module, the advisory output to at least an advisor client device.

8. The method of claim 7, wherein the server is part of the vibrant constitutional network system.

9. The method of claim 7, further comprising presenting, at a graphical user interface, a physical performance entity profile to the user.

10. The method of claim 7, further comprising performing, at an artificial intelligence advisor or the advisory module, a user textual conversation with the user client device.

11. The method of claim 7, wherein receiving training data at the diagnostic engine includes receiving a first training set including a plurality of first data entries and a second training set including a plurality of second data entries.

12. The method of claim 7, wherein generating the diagnostic output further comprises performing at least a machine-learning algorithm as a function of the training data and the at least a biological extraction.

13. The system of claim 1, wherein the system further comprises a wearable device comprising at least a sensor communicatively connected to the at least a server, wherein the at least a sensor is configured to record the at least a biological extraction of the user and transmit the at least a biological extraction to the diagnostic engine, and wherein recording the at least a biological extraction of the user comprises capturing mobility data of the user.

14. The method of claim 7, wherein the method further comprises:
    recording, by at least a sensor of a wearable device, the at least a biological extraction of the user, wherein:
        recording the at least a biological extraction of the user comprises capturing mobility data of the user; and
    transmitting, by the at least a sensor communicatively connected to the at least a server, the at least a biological extraction to the diagnostic engine.

* * * * *